US012630530B2

(12) United States Patent
Lu et al.

(10) Patent No.: US 12,630,530 B2
(45) Date of Patent: May 19, 2026

(54) FGFR INHIBITOR COMPOUND AND USE THEREOF

(71) Applicant: HENAN MEDINNO PHARMACEUTICAL TECHNOLOGY CO., LTD., Zhengzhou (CN)

(72) Inventors: Liang Lu, Zhengzhou (CN); Saisai Zhao, Zhengzhou (CN); Jixuan Zhang, Zhengzhou (CN); Hai Huang, Zhengzhou (CN); Longzheng Zhang, Zhengzhou (CN)

(73) Assignee: HENAN MEDINNO PHARMACEUTICAL TECHNOLOGY CO., LTD. (CN)

( * ) Notice: Subject to any disclaimer, the term of this patent is extended or adjusted under 35 U.S.C. 154(b) by 716 days.

(21) Appl. No.: 18/167,227

(22) Filed: Feb. 10, 2023

(65) Prior Publication Data

US 2023/0192656 A1 Jun. 22, 2023

Related U.S. Application Data

(63) Continuation of application No. PCT/CN2021/111774, filed on Aug. 10, 2021.

(30) Foreign Application Priority Data

Aug. 11, 2020 (CN) ......................... 202010800657.1

(51) Int. Cl.
*C07D 401/14* (2006.01)
*C07D 401/12* (2006.01)
*C07D 405/14* (2006.01)

(52) U.S. Cl.
CPC ......... *C07D 401/14* (2013.01); *C07D 401/12* (2013.01); *C07D 405/14* (2013.01); *C07B 2200/05* (2013.01)

(58) Field of Classification Search
CPC .. C07D 401/14; C07D 401/12; C07D 405/14; C07B 2200/05
USPC ..................................................... 514/210.21
See application file for complete search history.

(56) References Cited

U.S. PATENT DOCUMENTS 10,519,133 B2 * 12/2019 Chen .................... C07D 403/14

FOREIGN PATENT DOCUMENTS

| | | | |
|---|---|---|---|
| CN | 1556702 | A | 12/2004 |
| CN | 101622244 | A | 1/2010 |
| CN | 102421769 | A | 4/2012 |
| CN | 103193773 | A | 7/2013 |
| CN | 103534239 | A | 1/2014 |
| CN | 106279119 | A | 1/2017 |
| JP | 2012526126 | A | 10/2012 |
| JP | 2018531218 | A | 10/2018 |
| WO | 2017024968 | A1 | 2/2017 |
| WO | 2019109995 | A1 | 6/2019 |
| WO | 2021138391 | A1 | 7/2021 |

OTHER PUBLICATIONS

The Extended European Search Report for the European Patent Application No. 21855524.1, issued on Dec. 14, 2023.
The First Office Action issued by the European Patent Office dated Jan. 26, 2024 for the European Patent Application No. 21855524.1.
The First Office Action issued by the Japanese Patent Office dated Feb. 6, 2024 for the Japanese Patent Application No. 2023-507336. (English translation included).
China National Intellectual Property Administration; First Office Action issued in App No. 202110911922.8 dated Oct. 11, 2024.
International Search Report and Written Opinion of PCT/CN2021/111774, dated Nov. 10, 2021.
Casadei et al. "Targeted therapies for advanced bladder cancer: new strategies with FGFR inhibitors." Therapeutic advances in medical oncology, 11, 2019.
Dai et al. "Fibroblast growth factor receptors (FGFRs): structures and small molecule inhibitors." Cells 8(6), 614, Jun. 2019.
Lau et al. "Mechanisms of acquired resistance to fibroblast growth factor receptor targeted therapy." Cancer Drug Resistance 2(3), 568, 2019.
Tan et al. "Development of covalent inhibitors that can overcome resistance to first-generation FGFR kinase inhibitors." Proceedings of the National Academy of Sciences 111(45), E4869-E4877, Oct. 2014.

(Continued)

*Primary Examiner* — Kortney L. Klinkel
*Assistant Examiner* — Grace Ching Hsu
(74) *Attorney, Agent, or Firm* — MASCHOFF BRENNAN

(57) ABSTRACT

The present disclosure relates to FGFR inhibitor compounds and its use. Specifically, the present disclosure discloses a compound represented by formula (I), isotopically labeled compound thereof, or optical isomer thereof, geometric isomer thereof, a tautomer thereof or a mixture of various isomers, or a pharmaceutically acceptable salt thereof, or a prodrug thereof, or a metabolite thereof. The present disclosure also relates to use of the above compound in medicine.

(I)

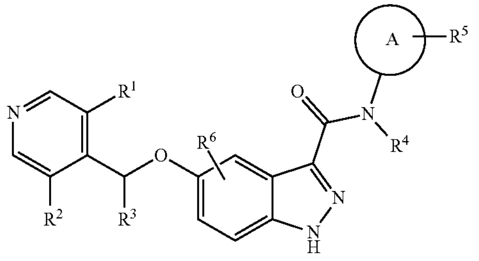

6 Claims, No Drawings

(56) References Cited

OTHER PUBLICATIONS

Wu et al. "LY2874455 potently inhibits FGFR gatekeeper mutants and overcomes mutation-based resistance." Chemical Communications 54, 2089-12092, 2018.
Fumarola et al. "Expanding the arsenal of FGFR inhibitors: a novel chloroacetamide derivative as a new irreversible agent with anti-proliferative activity against FGFR1-amplified lung cancer cell lines." Frontiers in Oncology, 9(179), Mar. 2019.
Stahl et al. "Handbook of pharmaceutical salts: properties, selection and use." Chemistry International, 24(3), 2002.

* cited by examiner

FGFR INHIBITOR COMPOUND AND USE THEREOF

CROSS REFERENCE TO RELATED APPLICATION

This application is a continuation of International application No. PCT/CN2021/111774, filed on Aug. 10, 2021, which claims priority to Chinese Patent Application No. 202010800657.1, filed on Aug. 11, 2020, both of which are incorporated herein by reference in their entireties.

TECHNICAL FIELD

The present disclosure provides a class of novel compounds with pharmacological activity, which can be used to inhibit fibroblast growth factor receptor, FGFR. The present disclosure also relates to a composition comprising the compound, and use of the compound and the composition in the preparation of a medicament for the treatment of FGFR-related diseases or disorders.

BACKGROUND

The fibroblast growth factor receptor (FGFR) family is a class of transmembrane receptor tyrosine kinases (RTK) and includes four members: FGFR1, FGFR2, FGFR3 and FGFR4. FGFRs can be activated by the binding of natural ligands. Activated FGFRs can then activate a variety of downstream signaling pathways including Ras-MAPK, AKT-PI3K and phospholipase C, which are involved in a variety of important physiological processes, such as proliferation, differentiation, cell migration and survival, among others.

Aberrant constitutive activation of FGFRs is found in a variety of tumors. Several inhibitors of FGFRs have been developed for the treatment of various cancers. Preclinical and early clinical trials have demonstrated that multiple FGFR inhibitors are effective in reducing tumor size.

However, one of the major obstacles to the use of FGFR inhibitors in clinical cancer therapy is the acquired resistance against them. This resistance can be acquired through mutations or activation of back-complementary signaling pathways in FGFRs, wherein the mutations on residues known as gatekeepers (referred to as gatekeeper mutations) is one of the most common pathways of resistance acquisition.

Drug resistance due to gatekeeper mutations in FGFRs has been reported in both preclinical and clinical trials. For example, the V561M mutation in FGFR1 leads to strong resistance to FIIN-1; the V564F mutation in FGFR2 leads to strong resistance to BGJ398; and the V555M mutation in FGFR3 leads to resistance to AZ8010, PD173074 and AZD4547.

The development of FGFR inhibitors that still have inhibitory activity against FGFRs carrying gatekeeper mutations is expected to address the acquired resistance caused by gatekeeper mutations. Recent studies have reported several inhibitors that are effective against FGFR gatekeeper mutations, such as FIIN2.

There remains a need for FGFR inhibitors that are more effective, for example, FGFR inhibitors having higher inhibition rates, targeting a wider variety of FGFR and FGFR mutations, or having higher selectivity for certain FGFRs and FGFR mutations, among others.

SUMMARY

In a first aspect, the present disclosure provides a compound of Formula (I) as a FGFR inhibitor, that is capable of inhibiting both wild and mutant FGFRs (I)

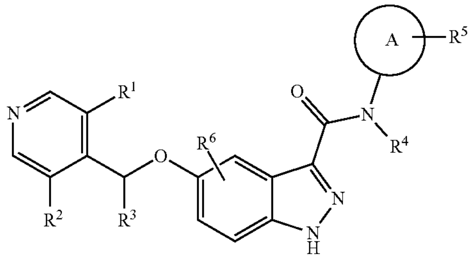

or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof, wherein A is selected from $C_{5-8}$ aryl, $C_{7-11}$ bicycloaryl, 5-7 membered heteroaryl, 7-11 membered bicycloheteroaryl, $C_{3-8}$ cycloalkyl, and 4-8 membered heterocycloalkyl; and $R^1$ and $R^2$ are each independently selected from H, halogen, —CN, —$NO_2$, $C_{1-3}$ alkyl, $C_{1-3}$ haloalkyl, $C_{1-3}$ alkoxy, $C_{3-6}$ cycloalkyl, and 4-6 membered heterocycloalkyl; and $R^3$ and $R^4$ are each independently selected from H, $C_{1-3}$ alkyl, $C_{1-3}$ haloalkyl, $C_{1-3}$ alkoxy, $C_3$. 6 cycloalkyl, and 4-6 membered heterocycloalkyl; and 0, 1, 2, 3, 4, 5, 6, 7, or 8 $R^5$(s) are present in formula (I), and each $R^5$ is independently selected from H, halogen, —OH, —$NO_2$, —CN, —$SF_5$, —SH, —S—$C_{1-4}$ alkyl, $C_{1-6}$ alkyl, $C_{1-6}$ haloalkyl, $C_{1-6}$ alkoxy, $C_{1-6}$ haloalkoxy, $C_{2-8}$ alkenyl, $C_{2-8}$ alkynyl, $C_{3-7}$ cycloalkyl, 3-10 membered heterocycloalkyl, $C_{6-12}$ bicycloalkyl, 6-12 membered bicycloheteroalkyl, $C_{8-15}$ tricycloalkyl, 8-15 membered tricycloheteroalkyl, $C_{5-8}$ aryl, 5-7 membered heteroaryl, $C_{7-11}$ bicycloaryl, 7-11 membered bicycloheteroaryl, —$C_{1-4}$ alkyl-($C_{3-7}$ cycloalkyl), —$C_{1-4}$ alkyl-(3-10 membered heterocycloalkyl), —$C_{1-4}$ alkyl-($C_{6-12}$ bicycloalkyl), —$C_{1-4}$ alkyl-(6-12 membered bicycloheteroalkyl), —$C_{1-4}$ alkyl-($C_{8-15}$-tricycloalkyl), —$C_{1-4}$ alkyl-(8-15 membered tricycloheteroalkyl), —N($R^7$)($R^8$), —N($R^7$)(C(═O)$R^8$), —N($R^7$)(C(═O)—O$R^8$), —N($R^7$)(C(═O)—N($R^8$)($R^9$)), —C(═O)—N($R^7$)($R^8$), —C(═O)—$R^7$, —C(═O)—O$R^7$, —OC(═O)$R^7$, —N($R^7$)(S(═O)$_2R^8$), —S(═O)$_2$—N($R^7$)($R^8$), —S$R^7$, and —O$R^7$, wherein the —S—$C_{1-4}$ alkyl, $C_{1-6}$ alkyl, $C_{1-6}$ alkoxy, $C_{1-6}$ haloalkoxy, $C_{2-8}$ alkenyl, $C_{2-8}$ alkynyl, $C_{3-7}$ cycloalkyl, 3-10 membered heterocycloalkyl, $C_{6-12}$ bicycloalkyl, 6-12 membered bicycloheteroalkyl, $C_{8-15}$ tricycloalkyl, 8-15 membered tricycloheteroalkyl, $C_{5-8}$ aryl, 5-7 membered heteroaryl, $C_{7-11}$ bicycloaryl, 7-11 membered bicycloheteroaryl, —$C_{1-4}$ alkyl-($C_{3-7}$ cycloalkyl), —$C_{1-4}$ alkyl-(3-10 membered heterocycloalkyl), —$C_{1-4}$ alkyl-($C_{6-12}$ bicycloalkyl), —$C_{1-4}$ alkyl-(6-12 membered bicycloheteroalkyl), —$C_{1-4}$ alkyl-($C_{8-15}$ tricycloalkyl), and —$C_{1-4}$ alkyl-(8-15 membered tricycloheteroalkyl) are each optionally substituted with 0, 1, 2, 3 or 4 $R^{5a}$;

$R^{5a}$ is independently selected from H, halogen, —OH, —$NO_2$, —CN, —$SF_5$, —SH, —S—$C_{1-4}$ alkyl, $C_{1-6}$ alkyl, $C_{1-6}$ haloalkyl, $C_{1-6}$ alkoxy, $C_{1-6}$ haloalkoxy, $C_{2-8}$ alkenyl, $C_{2-8}$ alkynyl, $C_{3-7}$ cycloalkyl, 3-10 membered heterocycloalkyl, $C_{6-12}$ bicycloalkyl, 6-12 membered bicycloheteroalkyl, $C_{8-15}$ tricycloalkyl, 8-15 membered tricycloheteroalkyl, $C_{5-8}$ aryl, 5-7 membered heteroaryl, $C_{7-11}$ bicycloaryl, 7-11 membered bicycloheteroaryl, —$C_{1-4}$ alkyl-($C_{3-7}$ cycloalkyl), —$C_{1-4}$ alkyl-(3-10 membered heterocycloalkyl), —$C_{1-4}$ alkyl-($C_{6-12}$ bicycloalkyl), —$C_{1-4}$ alkyl-(6-12 membered bicycloheteroalkyl), —N($R^7$)($R^8$), —N($R^7$)(C(═O)$R^8$), —N($R^7$)(C(═O)—O$R^8$), —N($R^7$)(C(═O)—N($R^8$)($R^9$)), —C(═O)—N($R^7$)($R^8$), —C(═O)—$R^7$, —C(═O)—O$R^7$, —OC(═O)$R^7$, —N($R^7$)(S(═O)$_2$ $R^8$), —S(═O)$_2$—N($R^7$)($R^8$), —S$R^7$, and —O$R^7$, wherein the —S—$C_{1-4}$ alkyl, $C_{1-6}$ alkyl, $C_{1-6}$ haloalkyl, $C_{1-6}$ alkoxy, $C_{1-6}$ haloalkoxy, $C_{2-8}$ alkenyl, $C_{2-8}$ alkynyl, $C_{3-7}$ cycloalkyl, 3-10 membered heterocycloalkyl, $C_{6-12}$ bicycloalkyl, 6-12 membered bicycloheteroalkyl, $C_{8-15}$ tricycloalkyl, 8-15 membered tricycloheteroalkyl, $C_{5-8}$ aryl, 5-7 membered heteroaryl, $C_{7-11}$ bicycloaryl, 7-11 membered bicycloheteroaryl, —$C_{1-4}$ alkyl-($C_{3-7}$ cycloalkyl), —$C_{1-4}$ alkyl-(3-10 membered heterocycloalkyl), —$C_{1-4}$ alkyl-($C_{6-12}$ bicycloalkyl) and —$C_{1-4}$ alkyl-(6-12 membered bicycloheteroalkyl) are each optionally substituted with 0, 1, 2, 3 or 4 $R^{5b}$;

$R^{5b}$ is independently selected from H, halogen, —OH, —CN, —$NO_2$, —$SF_5$, —SH, —S—$C_{1-4}$ alkyl, oxo, $C_{1-6}$ alkyl, $C_{1-6}$ haloalkyl, $C_{1-6}$ alkoxy, $C_{1-6}$ haloalkoxy, $C_{3-7}$ cycloalkyl, 3-10 membered heterocycloalkyl, $C_{6-10}$ aryl, 5-10 membered heteroaryl, —$C_{1-4}$ alkyl-($C_{3-7}$ cycloalkyl), —$C_{1-4}$ alkyl-(3-10 membered heterocycloalkyl), —N($R^7$)($R^8$), —N($R^7$)(C(═O)$R^8$), —N($R^7$)(C(═O)—O$R^8$), —N($R^7$)(C(═O)—N($R^8$)($R^9$)), —C(═O)—N($R^7$)($R^8$), —C(═O)—$R^7$, —C(═O)—O$R^7$, —OC(═O)$R^7$, —N($R^7$)(S(═O)$_2$ $R^8$), and —S(═O)$_2$—N($R^7$)($R^8$), wherein the —S—$C_{1-4}$ alkyl, $C_{1-6}$ alkyl, $C_{1-6}$ haloalkyl, $C_{1-6}$ alkoxy, $C_{1-6}$ haloalkoxy, $C_{3-7}$ cycloalkyl, 3-10 membered heterocycloalkyl, $C_{6-10}$ aryl, 5-10 membered heteroaryl, —$C_{1-4}$ alkyl-($C_{3-7}$ cycloalkyl), and —$C_{1-4}$ alkyl-(3-10 membered heterocycloalkyl) are each optionally substituted with 0, 1, 2, 3 or 4 substitutes each independently selected from a group consisting of halogen, —OH, —$NH_2$, —NH($CH_3$), —N($CH_3$)$_2$, —CN, —$NO_2$, —$SF_5$, —SH, —S—$C_{1-4}$ alkyl, oxo, $C_{1-4}$ alkyl, $C_{2-6}$ alkenyl, $C_{2-6}$ alkynyl, $C_{3-7}$ cycloalkyl, $C_{1-4}$ hydroxyalkyl, —S—$C_{1-4}$ alkyl, —C(═O)H, —C(═O)—$C_{1-4}$ alkyl, —C(═O)—O—$C_{1-4}$ alkyl, —C(═O)—$NH_2$, —C(═O)—N($C_{1-4}$ alkyl)$_2$, $C_{1-4}$ haloalkyl, $C_{1-4}$ alkoxy and $C_{1-4}$ haloalkoxy; and 0, 1, 2, or 3 $R^6$(s) are present in formula (I), and each $R^6$ is independently selected from H, halogen, —CN, —$NO_2$, $C_{1-3}$ alkyl, $C_{1-3}$ haloalkyl, $C_{1-3}$ alkoxy, $C_{3-6}$ cycloalkyl, and 4-6 membered heterocycloalkyl, and $R^7$, $R^8$, and $R^9$, at each occurrence, are each are each independently selected from a group consisting of: H, $C_{1-6}$ alkyl, $C_{1-4}$ haloalkyl, $C_{3-7}$ cycloalkyl, 3-10 membered heterocycloalkyl, $C_{6-10}$ aryl, 5-10 membered heteroaryl, ($C_{3-7}$ cycloalkyl)-$C_{1-4}$ alkyl-, (3-10 membered heterocycloalkyl)-$C_{1-4}$ alkyl-, ($C_{6-10}$ aryl)-$C_{1-4}$ alkyl- and (5-10 membered heteroaryl)-$C_{1-4}$ alkyl-, wherein each substituent listed in the group is optionally substituted with 0, 1, 2, 3, or 4 substituents each independently selected from a group consisting of: halogen, —OH, —$NH_2$, —NH($CH_3$), —N($CH_3$)$_2$, —CN, —$NO_2$, —$SF_5$, —SH, —S—$C_{1-4}$ alkyl, oxo, $C_{1-4}$ alkyl, $C_{2-6}$ alkenyl, $C_{2-6}$ alkynyl, $C_{3-7}$ cycloalkyl, $C_{1-4}$ hydroxyalkyl, —S—$C_{1-4}$ alkyl, —C(═O)H, —C(═O)—$C_{1-4}$ alkyl, —C(═O)—O—$C_{1-4}$ alkyl, —C(═O)—$NH_2$, —C(═O)—N($C_{1-4}$ alkyl)$_2$, $C_{1-4}$ haloalkyl, $C_{1-4}$ alkoxy and $C_{1-4}$ haloalkoxy;

or $R^7$, $R^8$, and the atoms attached thereto together form a 3-14-membered ring;

or $R^8$, $R^9$, and the atoms attached thereto together form a 3-14-membered ring.

Unless otherwise indicated, the term "a compound as shown by Formula (I)", "a compound of Formula (I)", "a compound of Formula (II)", "a compound of Formula (III)", "a compound of Formula (IV)", "a compound of Formula (V)" or "a compound according to the present application" also encompasses any optical isomer, geometric isomer, tautomer or a mixture of various isomers of the compound.

The term "optical isomer" refers that when a compound has one or more chiral centers, each chiral center may have an R configuration or an S configuration, and the various isomers thus constituted are known as an optical isomer. Optical isomers comprise all diastereomers, enantiomers, meso forms, racemates or mixtures thereof. For example, optical isomers can be separated by a chiral chromatography or by chiral synthesis.

The term "geometric isomer" refers that when a double bond is present in a compound, the compound may exist as a cis isomer, a trans isomer, an E isomer, or a Z isomer. A geometric isomer comprises a cis isomer, trans isomer, E isomer, Z isomer, or a mixture thereof.

The term "tautomer" refers to an isomer that is formed by rapid movement of an atom at two positions in a single molecule. It will be understood by those skilled in the art that tautomers can be mutually transformed, and in a certain state, may coexist by reaching an equilibrium state.

Unless otherwise indicated, reference to "a compound as shown by Formula (I)", "a compound of Formula (I)", "a compound of Formula (II)", "a compound of Formula (III)", "a compound of Formula (IV)", "a compound of Formula (V)" or "a compound according to the present application" herein also encompasses isotopically-labeled compounds obtained by replacing any atom of the compound with its isotopic atom.

Examples of isotopes suitable for inclusion in the compounds of the invention include isotopes of hydrogen, such as $^2H$ (D) and $^3H$ (T), of carbon, such as $^{11}C$, $^{13}C$ and $^{14}C$, of chlorine, such as $^{36}Cl$, of fluorine, such as $^{18}F$, of iodine, such as $^{123}I$ and $^{125}I$, of nitrogen, such as $^{13}N$ and $^{15}N$, of oxygen, such as $^{15}O$, $^{17}O$ and $^{18}O$, and of sulphur, such as $^{35}S$.

The isotopically-labelled compounds, for example, those incorporating a radioactive isotope, are useful in drug and/or substrate tissue distribution studies. The radioactive isotopes deuterium, i.e. $^2H$, and carbon-14, i.e. $^{14}C$, are particularly useful for this purpose in view of their ease of incorporation and ready means of detection.

Substitution with heavier isotopes such as deuterium, i.e. D, may afford certain therapeutic advantages resulting from greater metabolic stability, for example, increased in vivo half-life or reduced dosage requirements, and hence may be preferred in some circumstances. Thus, in some embodiments, the compounds according to the present application are isotopically labeled compounds, wherein H is optionally replaced by D at each occurrence.

Substitution with positron emitting isotopes, such as $^{11}C$, $^{18}F$, $^{15}O$ and $^{13}N$, can be useful in Positron Emission Topography (PET) studies for examining substrate receptor occupancy.

The isotopically-labeled compounds can generally be prepared by conventional techniques known to those skilled in the art or using an appropriate isotopically-labeled reagents in place of the non-labeled reagent previously employed.

The compounds according to the present application may exist in the form of a pharmaceutically acceptable salt.

The pharmaceutically acceptable salt include acid addition salts and base addition salts thereof. Suitable acid addition salts are formed from acids that form non-toxic salts. Examples include but are not limited to: acetate, adipate, aspartate, benzoate, benzenesulfonate, bicarbonate/carbonate, bisulfate/sulfate, borate, camphor sulfonate, citrate, cyclohexamine sulfonate, ethanedisulfonate, formate, fumarate, glucoheptonate, gluconate, glucuronate, hexafluorophosphate, 2-(4-hydroxybenzyl) benzoate, hydrochloride/chloride, hydrobromide/bromide, hydroiodide/iodide, 2-isethionate, lactate, malate, maleate, malonate, methanesulfonate, methyl sulfate, naphthalate, 2-naphthalenesulfonate, nicotinate, nitrate, orotate, oxalate, palmitate, phosphate/hydrogen phosphate/dihydrogen phosphate, pyroglutamate, glucarate, stearate, salicylate, tannate, tartrate, tosylate and trifluoroacetate. Suitable base addition salts are formed from bases that form non-toxic salts. Examples thereof include, but are not limited to: aluminum, arginine, calcium, choline, diethylamine, diethanolamine, glycine, lysine, magnesium, meglumine, ethanolamine, potassium, sodium, tromethamine, and zinc salts. It is also possible to form half salts of acids and bases, such as hemisulfate and hemicalcium salts. For a review of suitable salts, please refer to Handbook of Pharmaceutical Salts: Properties, Selection and Use by Stahl and Wermuth (Wiley-VCH, 2002). Methods for preparing pharmaceutically acceptable salts of the compounds described herein are known to those skilled in the art.

Moreover, the compounds according to the present application may exist in unsolvated form as well as solvated forms with pharmaceutically acceptable solvents such as water, ethanol and the like. The compounds may exist in one or more crystalline forms, or in an amorphous form. These forms are included within the scope of the invention.

The present application further comprises prodrug of the compounds according to the present application. The "prodrug" refers to a derivative that is converted into a compound according to the present disclosure by a reaction with enzymes, gastric acid, and the like in a living body under physiological conditions, for example, through oxidation, reduction, hydrolysis, and the like catalyzed by enzymes. Thus, some derivatives of the compounds according to the present application may have little or no pharmacological activity on their own, and can be converted into compounds according to the present application with the desired activity when administered to the body or on the body of a patient.

The present application further comprises metabolite of the compounds according to the present application. The "metabolite" refers to all molecules derived from any compound according to the present disclosure in a cell or organism, preferably a human.

As used herein, the term "substituted" means that one or more (preferably 1 to 5, more preferably 1 to 3) hydrogen atoms in a group are independently replaced by a corresponding number of substituents.

As used herein, the term "independently" means that when the number of substituents is more than one, these substituents may be the same or different.

As used herein, the term "optional" or "optionally" means that the event described therein may or may not occur. For example, an "optionally substituted" group means that the group may be unsubstituted or substituted.

The term "halogen" or "halo" refers to —F, —Cl, —Br, or —I.

As used herein, the term "alkyl" refers to saturated aliphatic hydrocarbons, including straight and branched chains. In some embodiments, the alkyl group has 1-8, or 1-6, or 1-3 carbon atoms. For example, the term "$C_{1-8}$ alkyl" refers to a straight or branched chain group of atoms having 1-8 carbon atoms. The term "$C_{1-8}$ alkyl" includes the terms "$C_{1-6}$ alkyl", "$C_{1-3}$ alkyl" and "$C_{1-4}$ alkyl" in its definition. Examples of alkyl groups include, but are not limited to, methyl, ethyl, propyl, isopropyl, butyl, isobutyl, sec-butyl, tert-butyl, pentyl, 2-pentyl, 3-pentyl, isopentyl, neopentyl, (R)-2-methylbutyl, (S)-2-methylbutyl, 3-methylbutyl, 2,3-dimethylpropyl, 2,3-dimethylbutyl, hexyl, and the like. The alkyl group may be optionally substituted with one or more (for example, 1 to 5) suitable substituent(s).

As used herein, the term "alkenyl" refers to an aliphatic hydrocarbon having at least one carbon-carbon double bond, including straight and branched chains having at least one carbon-carbon double bond. In some embodiments, alkenyl groups have 2-8 carbon atoms, 2-6 carbon atoms, 3-6 carbon atoms, or 2-4 carbon atoms. For example, the term "$C_{2-8}$ alkenyl" refers to a linear or branched unsaturated atomic group (having at least one carbon-carbon double bond) having 2-8 carbon atoms. The double bond may or may not be the point of attachment of another group. Alkenyl groups include, but are not limited to, vinyl, 1-propenyl, 2-propenyl, 2-methyl-2-propenyl, butenyl, pentenyl, 3-hexenyl, and the like. Alkenyl groups may be optionally substituted with one or more (for example, 1 to 5) suitable substituent(s). When the compound of formula (I) contains an alkenyl group, the alkenyl group may be present in the pure E form, the pure Z form, or any mixture thereof.

As used herein, the term "alkynyl" refers to an aliphatic hydrocarbon having at least one carbon-carbon triple bond, including straight and branched chains having at least one carbon-carbon triple bond. In some embodiments, an alkynyl group has 2-8 carbon atoms, 2-6 carbon atoms, 3-6 carbon atoms, or 2-4 carbon atoms. For example, the term "$C_{2-8}$ alkynyl" refers to a linear or branched unsaturated atomic group (having at least one carbon-carbon triple bond) having 2-8 carbon atoms. The triple bond may or may not be the point of attachment of another group. Alkynyl groups include, but are not limited to, ethynyl, 1-propynyl, 2-propynyl, 2-methyl-2-propynyl, butynyl, pentynyl, 3-hexynyl, and the like. The alkynyl group may be optionally substituted with one or more (for example, 1 to 5) suitable substituent(s).

As used herein, the term "$C_{3-8}$ cycloalkyl" refers to a cycloalkyl group having 3-8 ring-forming carbon atoms. The term "$C_{3-7}$ cycloalkyl" refers to a cycloalkyl group having 3-7 ring-forming carbon atoms. The term "$C_{3-6}$ cycloalkyl" refers to a cycloalkyl group having 3-6 ring-forming carbon atoms. The cycloalkyl may be a monocyclic ring. The definition of cycloalkyl also includes unsaturated non-aromatic cycloalkyl groups. Examples of cycloalkyl are, for example, cyclopropyl, cyclobutyl, cyclopentyl, cyclohexyl, cyclohexenyl, cycloheptyl, cyclooctyl, cyclohexadienyl, cyclopentenyl, cycloheptenyl and cyclooctenyl. The cycloalkyl may be optionally substituted with one or more suitable substituent(s).

As used herein, the term "$C_{6-12}$ bicycloalkyl" is an alkyl group containing two rings with 6-12 ring-forming carbon atoms. The bicycloalkyl may be fused or may include a bridging for the bicyclic system.

As used herein, the term "$C_{8-15}$ membered tricycloalkyl" is an alkyl group containing three rings with 8-15 ring-forming carbon atoms. The tricycloalkyl group may be fused or bridged.

As used herein, the term "n-membered heterocycloalkyl" refers to a cycloalkyl group having m ring-forming carbon atoms and (n-m) ring-forming heteroatoms, the heteroatoms being selected from O, S and N. For example, the term "4-8-membered heterocycloalkyl" refers to a heterocycloalkyl substituent containing a total of 4 to 8 ring atoms, of which at least one is a heteroatom; the term "4-6-membered heterocycloalkyl" refers to a heterocycloalkyl substituent containing a total of 4 to 8 ring atoms, of which at least one is a heteroatom; and the term "3-10-membered heterocycloalkyl" refers to a heterocycloalkyl substituent containing a total of 3 to 10 ring atoms, of which at least one is a heteroatom. The term "n-membered bicycloheteroalkyl" refers to a bicycloheteroalkyl group having m ring-forming carbon atoms and (n-m) ring-forming heteroatoms, the heteroatoms being selected from O, S and N. Examples of heterocycloalkyl includes, but not limited to, azetidinyl, thietidinyl, dihydrofuranyl, dihydrothiophenyl, tetrahydrothienyl, tetrahydrofuranyl, tetrahydrotriazinyl, tetrahydropyrazolyl, tetrahydrooxazinyl, tetrahydropyrimidinyl, octahydrobenzofuranyl, octahydrobenzimidazolyl, octahydrobenzothiazolyl, imidazolidinyl, pyrrolidinyl, piperidinyl, piperazinyl, oxazolidinyl, thiazolidinyl, pyrazolidinyl, thiomorpholinyl, tetrahydropyrimidinyl tetrahydrothiopyranyl, tetrahydrothiazinyl, tetrahydrothiadiazinyl, tetrahydrooxazolyl, morpholinyl, oxetanyl, tetrahydrodiazinyl, oxazinyl, oxathiadiazinyl, quinuclidinyl, benzodipyranyl (chromanyl), isobenzodipyranyl (isochromanyl), dihydrobenzodioxinyl, benzodioxolyl, benzoxazinyl, dihydroindolyl, dihydrobenzofuranyl, tetrahydroquinolinyl, isochromanyl, dihydro-1H-isoindolyl, 2-azabicyclo[2.2.1]heptanoyl, 3-azabicyclo[3.1.0]hexyl, 3-azabicyclo[4.1.0]heptyl, oxacycloheptyl, thiacycloheptyl, azacycloheptyl, and the like. The heterocycloalkyl may be optionally substituted with one or more suitable substituent(s).

As used herein, the term "$C_{5-8}$ aryl" refers to an aryl group having an aromatic ring containing 5-8 carbon atoms, for example phenyl.

As used herein, the term "n-membered heteroaryl" refers to a heteroaryl group having m aromatic ring-forming carbon atoms and (n-m) aromatic ring-forming heteroatoms, the heteroatoms being selected from O, S and N. For example, 5-7 membered heteroaryl includes but not limited to furanyl, thienyl, pyrrolyl, thiazolyl, pyrazolyl, imidazolyl, pyridinyl, pyranyl, pyridazinyl, pyrimidinyl, pyrazinyl. The heteroaryl may be optionally substituted with one or more suitable substituent(s).

As used herein, the term "$C_{7-11}$ bicycloaryl" refers to a bicycloaryl group having 7-11 carbon atoms, such as naphthalene, indene and the like. The bicycloaryl may be optionally substituted with one or more suitable substituent(s).

As used herein, the term "n-membered bicycloheteroaryl" refers to a bicycloheteroaryl group having m carbon atoms forming an aromatic bicyclic ring and (n-m) heteroatoms forming an aromatic bicyclic ring, and the heteroatoms are selected from O, S and N. For example, 7-11 membered bicycloheteroaryl includes, but not limited to, quinolinyl, isoquinolinyl, indolyl, purinyl, benzothiazolyl. The bicycloheteroaryl may be optionally substituted with one or more suitable substituent(s).

As used herein, the term "11-15 membered tricyclyl" includes but not limited to acridine and the like. The 11-15 membered tricyclyl may be optionally substituted with one or more suitable substituent(s).

As used herein, the term "haloalkyl" refers to an alkyl group having one or more halogen substituent(s)(up to perhaloalkyl, that is, each hydrogen atom of the alkyl is replaced by a halogen atom). For example, the term "$C_{1-6}$ haloalkyl" refers to a $C_{1-6}$ alkyl group with one or more halogen substituent(s)(up to perhaloalkyl, that is, each hydrogen atom of the alkyl group is replaced by a halogen atom). As another example, the term "$C_{1-4}$ haloalkyl" refers to a $C_{1-4}$ alkyl group with one or more halogen substituent (s)(up to perhaloalkyl, that is, each hydrogen atom of the alkyl group is replaced by a halogen atom); the term "$C_{1-3}$ haloalkyl" refers to a $C_{1-3}$ alkyl group with one or more halogen substituent(s)(up to perhaloalkyl, that is, each hydrogen atom of the alkyl group is replaced by a halogen atom); and the term "$C_{1-2}$ haloalkyl" refers to a $C_{1-2}$ alkyl group (i.e. methyl or ethyl) with one or more halogen substituent(s)(up to perhaloalkyl, that is, each hydrogen atom of the alkyl group is replaced by a halogen atom). As another example, the term "$C_1$ haloalkyl" refers to a methyl group with 1, 2, or 3 halogen substituent(s). Examples of haloalkyl groups include: $CF_3$, $C_2F_5$, $CHF_2$, $CH_2F$, $CH_2CF_3$, $CH_2Cl$, and the like.

As used herein, the term "alkoxy" refers to alkyl with a single bond attached to an oxygen atom. The point of attachment of the alkoxy group to a molecule is through the oxygen atom. Alkoxy can be described as alkyl-O—. The term "$C_{1-6}$ alkoxy" refers to a linear or branched alkoxy group containing 1 to 6 carbon atoms. The term "$C_{1-6}$ alkoxy" includes the term "$C_{1-3}$ alkoxy" in its definition. Alkoxy includes, but not limited to, methoxy, ethoxy, propoxy, isopropoxy, butoxy, hexoxy, and the like. The alkoxy group may be optionally substituted with one or more suitable substituent(s).

As used herein, the term "3-14-membered ring" refers to a saturated or unsaturated ring system with 3-14 ring-forming atoms.

Herein, a numerical range relating to the number of substituents, the number of carbon atoms, or the number of ring members represents an enumeration of all integers in the range, and the range is only a simplified representation thereof. For example: "4 to 6-membered ring" means a 4, 5 or 6-membered ring; "5 to 7-membered ring" means a 5, 6 or 7-membered ring; "7 to 11-membered ring" means a 7, 8, 9, 10 or 11-membered ring; "4 to 8-membered ring" means a 4, 5, 6, 7 or 8-membered ring; "3 to 10-membered ring" means a 3, 4, 5, 6, 7, 8, 9 or 10-membered ring; "$C_{1-3}$" means 1 ($C_1$), 2 ($C_2$), or 3 ($C_3$) carbon atoms; "$C_{3-6}$" means 3 ($C_3$), 4 ($C_4$), 5 ($C_5$), or 6 ($C_6$) carbon atoms; "$C_{3-8}$" means 3 ($C_3$), 4 ($C_4$), 5 ($C_5$), 6 ($C_6$), 7 ($C_7$), or 8 ($C_8$) carbon atoms; "$C_{5-7}$" means 5 ($C_5$), 6 ($C_6$), or 7 ($C_7$) carbon atoms; "$C_{7-11}$" means 7 ($C_7$), 8 ($C_8$), 9 ($C_9$), 10 ($C_{10}$), or 11 ($C_{11}$) carbon atoms. Thus, a numerical range associated with the number of substituents, the number of carbon atoms, or the number of ring members also encompasses any one of its subranges, and each subrange is also considered to be disclosed herein.

In formula (I) as described above, $R^3$ is selected from H, $C_{1-3}$ alkyl, $C_{1-3}$ haloalkyl, $C_{1-3}$ alkoxy, $C_{3-6}$ cycloalkyl, and 4-6 membered heterocycloalkyl.

In some preferred embodiments, $R^3$ is H.

In some embodiments, $R^3$ is $C_{1-3}$ alkyl or $C_{1-3}$ haloalkyl, e.g., $R^3$ is selected from methyl, ethyl, propyl, isopropyl optionally substituted with one or more halogen atoms (e.g., fluorine, chlorine, bromine, iodine). In some preferred embodiments, $R^3$ is methyl.

In some embodiments, $R^3$ is a $C_{1-3}$ alkoxy, e.g., $R^3$ is selected from methoxy, ethoxy, propoxy, isopropoxy.

In some embodiments, $R^3$ is $C_{3-6}$ cycloalkyl, e.g., $R^3$ is selected from cyclopropyl, cyclobutyl, cyclopentyl, cyclohexyl, and cyclohexenyl.

In some embodiments, $R^3$ is a 4-6 membered heterocycloalkyl, e.g., $R^3$ is selected from oxetanyl, thietanyl, azetidinyl, tetrahydrofuranyl, tetrahydrothienyl, pyrrolidinyl, tetrahydropyranyl, tetrahydrothiopyranyl, piperidinyl, morpholinyl, and piperazinyl.

It should be understood that any of the above embodiments of $R^3$ may be combined with any of the embodiments of $R^1$, $R^2$, A, $R^4$, $R^5$, $R^6$, $R^7$, and $R^8$ as described above and below.

In formula (I) as described above, $R^1$ is selected from H, halogen, —CN, —$NO_2$, $C_{1-3}$ alkyl, $C_{1-3}$ haloalkyl, $C_{1-3}$ alkoxy, $C_{3-6}$ cycloalkyl, and 4-6 membered heterocycloalkyl.

In some embodiments, $R^1$ is H.

In some embodiments, $R^1$ is halogen, e.g., $R^1$ is selected from F, Cl, Br, and I.

In some embodiments, $R^1$ is —CN.

In some embodiments, $R^1$ is —$NO_2$.

In some embodiments, $R^1$ is $C_{1-3}$ alkyl or $C_{1-3}$ haloalkyl, e.g., $R^1$ is selected from methyl, ethyl, propyl, and isopropyl optionally substituted with one or more halogen atoms (e.g., fluorine, chlorine, bromine, iodine).

In some embodiments, $R^1$ is $C_{1-3}$ alkoxy, e.g., $R^1$ is selected from methoxy, ethoxy, propoxy, and isopropoxy.

In some embodiments, $R^1$ is $C_{3-6}$ cycloalkyl, e.g., $R^1$ is selected from cyclopropyl, cyclobutyl, cyclopentyl, cyclohexyl, and cyclohexenyl.

In some embodiments, $R^1$ is 4-6 membered heterocycloalkyl, e.g., $R^1$ is selected from oxetanyl, thietanyl, azetidinyl, tetrahydrofuranyl, tetrahydrothienyl, pyrrolidinyl, tetrahydropyranyl, tetrahydrothiopyranyl, piperidinyl, morpholinyl, and piperazinyl.

It should be understood that any of the above embodiments of $R^1$ may be combined with any of the embodiments of $R^2$, $R^3$, A, $R^4$, $R^5$, $R^6$, $R^7$, and $R^8$ as described above and below.

In formula (I) as described above, $R^2$ is selected from H, halogen, —CN, —$NO_2$, $C_{1-3}$ alkyl, $C_{1-3}$ haloalkyl, $C_{1-3}$ alkoxy, $C_{3-6}$ cycloalkyl, and 4-6 membered heterocycloalkyl.

In some embodiments, $R^2$ is H.

In some embodiments, $R^2$ is halogen, e.g., $R^2$ is selected from F, Cl, Br, and I.

In some embodiments, $R^2$ is —CN.

In some embodiments, $R^2$ is —$NO_2$.

In some embodiments, $R^2$ is $C_{1-3}$ alkyl or $C_{1-3}$ haloalkyl, e.g., $R^2$ is selected from methyl, ethyl, propyl, and isopropyl optionally substituted with one or more halogen atoms (e.g., fluorine, chlorine, bromine, iodine).

In some embodiments, $R^2$ is a $C_{1-3}$ alkoxy, e.g., $R^2$ is selected from methoxy, ethoxy, propoxy, and isopropoxy.

In some embodiments, $R^2$ is $C_{3-6}$ cycloalkyl, e.g., $R^2$ is selected from cyclopropyl, cyclobutyl, cyclopentyl, cyclohexyl, and cyclohexenyl.

In some embodiments, $R^2$ is 4-6 membered heterocycloalkyl, e.g., $R^2$ is selected from oxetanyl, thietanyl, azetidinyl, tetrahydrofuranyl, tetrahydrothienyl, pyrrolidinyl, tetrahydropyranyl, tetrahydrothiopyranyl, piperidinyl, morpholinyl, and piperazinyl.

It should be understood that any of the above embodiments of $R^2$ may be combined with any of the embodiments of $R^1$, $R^3$, A, $R^4$, $R^5$, $R^6$, $R^7$, and $R^8$ as described above and below.

In some embodiments, $R^1$ and $R^2$ may be the same. For example, both $R^1$ and $R^2$ are halogen, such as Cl; further, for example, both $R^1$ and $R^2$ are methyl. In a preferred embodiment, both $R^1$ and $R^2$ are Cl.

In other embodiments, $R^1$ and $R^2$ may be different.

In formula (I) as described above, $R^4$ is selected from H, $C_{1-3}$ alkyl, $C_{1-3}$ haloalkyl, $C_{1-3}$ alkoxy, $C_{3-6}$ cycloalkyl, and 4-6 membered heterocycloalkyl.

In some preferred embodiments, $R^4$ is H.

In some embodiments, $R^4$ is $C_{1-3}$ alkyl or $C_{1-3}$ haloalkyl, e.g., $R^4$ is selected from methyl, ethyl, propyl, and isopropyl optionally substituted with one or more halogen atoms (e.g., fluorine, chlorine, bromine, iodine).

In some embodiments, $R^4$ is $C_{1-3}$ alkoxy, e.g., $R^4$ is selected from methoxy, ethoxy, propoxy, and isopropoxy.

In some embodiments, $R^4$ is $C_{3-6}$ cycloalkyl, e.g., $R^4$ is selected from cyclopropyl, cyclobutyl, cyclopentyl, cyclohexyl, and cyclohexenyl.

In some embodiments, $R^4$ is 4-6 membered heterocycloalkyl, e.g., $R^4$ is selected from oxetanyl, thietanyl, azetidinyl, tetrahydrofuranyl, tetrahydrothienyl, pyrrolidinyl, tetrahydropyranyl, tetrahydrothiopyranyl, piperidinyl, morpholinyl, and piperazinyl.

It should be understood that any of the above embodiments of $R^4$ may be combined with any of the embodiments of $R^1$, $R^2$, A, $R^3$, $R^5$, $R^6$, $R^7$, and $R^8$ as described above and below.

There may be 0, 1, 2, or 3 $R^6$(s) present in formula (I) as described above. In the presence of a plurality of $R^6$, each $R^6$ is each independently selected from H, halogen, —CN, —$NO_2$, $C_{1-3}$ alkyl, $C_{1-3}$ haloalkyl, $C_{1-3}$ alkoxy, $C_{3-6}$ cycloalkyl, and 4-6 membered heterocycloalkyl.

In some preferred embodiments, $R^6$ is H.

In some embodiments, $R^6$ is halogen, e.g., $R^6$ is selected from F, Cl, Br, and I.

In some embodiments, $R^6$ is —CN.

In some embodiments, $R^6$ is —$NO_2$.

In some embodiments, $R^6$ is $C_{1-3}$ alkyl or $C_{1-3}$ haloalkyl, e.g., $R^6$ is selected from methyl, ethyl, propyl, and isopropyl optionally substituted with one or more halogen atoms (e.g., fluorine, chlorine, bromine, iodine).

In some embodiments, $R^6$ is $C_{1-3}$ alkoxy, e.g., $R^6$ is selected from methoxy, ethoxy, propoxy, and isopropoxy.

In some embodiments, $R^6$ is $C_{3-6}$ cycloalkyl, e.g., $R^6$ is selected from cyclopropyl, cyclobutyl, cyclopentyl, cyclohexyl, and cyclohexenyl.

In some embodiments, $R^6$ is 4-6 membered heterocycloalkyl, e.g., $R^6$ is selected from oxetanyl, thietanyl, azetidinyl, tetrahydrofuranyl, tetrahydrothienyl, pyrrolidinyl, tetrahydropyranyl, tetrahydrothiopyranyl, piperidinyl, morpholinyl, and piperazinyl.

In some preferred embodiments, one $R^6$ is present.

It should be understood that any of the above embodiments of $R^6$ may be combined with any of the embodiments of $R^1$, $R^2$, A, $R^3$, $R^4$, $R^5$, $R^7$, and $R^8$ as described above and below.

In formula (I) as described above, A is selected from $C_{5-8}$ aryl, $C_{7-11}$ bicycloaryl, 5-7 membered heteroaryl, 7-11 membered bicycloheteroaryl, $C_{3-8}$ cycloalkyl, and 4-8 membered heterocycloalkyl.

In some embodiments, A is $C_{5-8}$ aryl, e.g., A is phenyl.

In some embodiments, A is $C_{7-11}$ bicycloaryl, e.g., A is selected from naphthyl, and indenyl.

In some embodiments, A is 5-7 membered heteroaryl, e.g., A is selected from furanopyridazinyl, thienyl, pyrrolyl, thiazolyl, pyrazolyl, imidazolyl, pyridinyl, pyranyl, pyridazinyl, pyrimidinyl, and pyrazinyl.

In some embodiments, A is 7-11-membered bicycloheteroaryl, e.g., A is selected from quinolinyl, isoquinolinyl, and benzothiazolyl.

In some embodiments, A is $C_{3-8}$ cycloalkyl, e.g., A is selected from cyclopropyl, cyclobutyl, cyclopentyl, cyclohexyl, cycloheptyl, cyclooctyl, cyclohexenyl, cyclohexadienyl, cyclopentenyl, cycloheptyl, and cyclooctenyl.

In some embodiments, A is 4-8-membered heterocycloalkyl, e.g., A is selected from oxetanyl, thietanyl, azetidinyl, tetrahydrofuranyl, tetrahydrothienyl, pyrrolidinyl, tetrahydropyranyl, tetrahydrothiopyranyl, piperidinyl, morpholinyl, and piperazinyl.

In some preferred embodiments, A is phenyl.

In some preferred embodiments, A is pyridinyl.

In some preferred embodiments, A is pyridazinyl.

In some preferred embodiments, A is pyrazolyl.

It should be understood by those skilled in the art that the various substituents or groups enumerated for A in the present application should be understood in their broad sense (i.e. covering the monovalent form, the divalent form, the trivalent form and the like of said substituents or groups) to satisfy the valence bonding rules of compounds. For example, A is a monovalent group when $R^5$ is not present (the number of $R^5$ is 0) or when the number of $R^5$ is 1 and $R^5$=H; A is a divalent group when the number of $R^5$ is 1 and $R^5$ is not H; and A is a trivalent group when the number of $R^5$ is 2 and neither of $R^5$ is H. For example, "phenyl", as enumerated above for A, may in different cases denote monovalent phenyl or divalent phenyl or trivalent phenyl; and the same applies to other substituents or groups.

It should be understood that any of the above embodiments of A may be combined with any of the embodiments of $R^1$, $R^2$, $R^3$, $R^4$, $R^5$, $R^6$, $R^7$, and $R^8$ as described above and below.

In formula (I) as described above, 0, 1, 2, 3, 4, 5, 6, 7, 8 or more $R^5$(s) may be present. In the presence of a plurality of $R^5$, each $R^5$ is independently selected from H, halogen, —OH, —$NO_2$, —CN, —$SF_5$, —SH, —S—$C_{1-4}$ alkyl, $C_{1-6}$ alkyl, $C_{1-6}$ haloalkyl, $C_{1-6}$ alkoxy, $C_{1-6}$ haloalkoxy, $C_{2-8}$ alkenyl, $C_{2-8}$ alkynyl, $C_{3-7}$ cycloalkyl, 3-10 membered heterocycloalkyl, $C_{6-12}$ bicycloalkyl, 6-12 membered bicycloheteroalkyl, $C_{8-15}$ tricycloalkyl, 8-15 membered tricycloheteroalkyl, $C_{5-8}$ aryl, 5-7 membered heteroaryl, $C_{7-11}$ bicycloaryl, 7-11 membered bicycloheteroaryl, —$C_{1-4}$ alkyl-($C_{3-7}$ cycloalkyl), —$C_{1-4}$ alkyl-(3-10 membered heterocycloalkyl), —$C_{1-4}$ alkyl-($C_{6-12}$ bicycloalkyl), —$C_{1-4}$ alkyl-(6-12 membered bicycloheteroalkyl), —$C_{1-4}$ alkyl-($C_{8-15}$ tricycloalkyl), —$C_{1-4}$ alkyl-(8-15 membered tricycloheteroalkyl), —$N(R^7)(R^8)$, —$N(R^7)(C(=O)R^8)$, —$N(R^7)(C(=O)—OR^8)$, —$N(R^7)(C(=O)—N(R^8)(R^9))$, —C(=O)—$N(R^7)(R^8)$, —C(=O)—$R^7$, —C(=O)—$OR^7$, —OC(=O)$R^7$, —$N(R^7)(S(=O)_2R^8)$, —$S(=O)_2$—$N(R^7)(R^8)$, —$SR^7$, and —$OR^7$, wherein the —S—$C_{1-4}$ alkyl, $C_{1-6}$ alkyl, $C_{1-6}$ alkoxy, $C_{1-6}$ haloalkoxy, $C_{2-8}$ alkenyl, $C_{2-8}$ alkynyl, $C_{3-7}$ cycloalkyl, 3-10 membered heterocycloalkyl, $C_{6-12}$ bicycloalkyl, 6-12 membered bicycloheteroalkyl, $C_{8-15}$ tricycloalkyl, 8-15 membered tricycloheteroalkyl, $C_{5-8}$ aryl, 5-7 membered heteroaryl, $C_{7-11}$ bicycloaryl, 7-11 membered bicycloheteroaryl, —$C_{1-4}$ alkyl-($C_{3-7}$ cycloalkyl), —$C_{1-4}$ alkyl-(3-10 membered heterocycloalkyl), —$C_{1-4}$ alkyl-($C_{6-12}$ bicycloalkyl), —$C_{1-4}$ alkyl-(6-12 membered bicycloheteroalkyl), —$C_{1-4}$ alkyl-($C_{8-15}$ tricycloalkyl), and —$C_{1-4}$ alkyl-(8-15 membered tricycloheteroalkyl) are each optionally substituted with 0, 1, 2, 3 or 4 $R^{5a}$.

$R^{5a}$ is independently selected from H, halogen, —OH, —$NO_2$, —CN, —$SF_5$, —SH, —S—$C_{1-4}$ alkyl, $C_{1-6}$ alkyl, $C_{1-6}$ haloalkyl, $C_{1-6}$ alkoxy, $C_{1-6}$ haloalkoxy, $C_{2-8}$ alkenyl, $C_{2-8}$ alkynyl, $C_{3-7}$ cycloalkyl, 3-10 membered heterocycloalkyl, $C_{6-12}$ bicycloalkyl, 6-12 membered bicycloheteroalkyl, $C_{8-15}$ tricycloalkyl, 8-15 membered tricycloheteroalkyl, $C_{5-8}$ aryl, 5-7 membered heteroaryl, $C_{7-11}$ bicycloaryl, 7-11 membered bicycloheteroaryl, —$C_{1-4}$ alkyl-($C_{3-7}$ cycloalkyl), —$C_{1-4}$ alkyl-(3-10 membered heterocycloalkyl), —$C_{1-4}$ alkyl-($C_{6-12}$ bicycloalkyl), —$C_{1-4}$ alkyl-(6-12 membered bicycloheteroalkyl), —$N(R^7)(R^8)$, —$N(R^7)(C(=O)R^8)$, —$N(R^7)(C(=O)—OR^8)$, —$N(R^7)(C(=O)—N(R^8)(R^9))$, —C(=O)—$N(R^7)(R^8)$, —C(=O)—$R^7$, —C(=O)—$OR^7$, —OC(=O)$R^7$, —$N(R^7)(S(=O)_2R^8)$, —$S(=O)_2$—$N(R^7)(R^8)$, —$SR^7$, and —$OR^7$, wherein the —S—$C_{1-4}$ alkyl, $C_{1-6}$ alkyl, $C_{1-6}$ haloalkyl, $C_{1-6}$ alkoxy, $C_{1-6}$ haloalkoxy, $C_{2-8}$ alkenyl, $C_{2-8}$ alkynyl, $C_{3-7}$ cycloalkyl, 3-10 membered heterocycloalkyl, $C_{6-12}$ bicycloalkyl, 6-12 membered bicycloheteroalkyl, $C_{8-15}$ tricycloalkyl, 8-15 membered tricycloheteroalkyl, $C_{5-8}$ aryl, 5-7 membered heteroaryl, $C_{7-11}$ bicycloaryl, 7-11 membered bicycloheteroaryl, —$C_{1-4}$ alkyl-($C_{3-7}$ cycloalkyl), —$C_{1-4}$ alkyl-(3-10 membered heterocycloalkyl), —$C_{1-4}$ alkyl-($C_{6-12}$ bicycloalkyl) and —$C_{1-4}$ alkyl-(6-12 membered bicycloheteroalkyl) are each optionally substituted with 0, 1, 2, 3 or 4 $R^{5b}$;

$R^{5b}$ is independently selected from H, halogen, —OH, —CN, —$NO_2$, —$SF_5$, —SH, —S—$C_{1-4}$ alkyl, oxo, $C_{1-6}$ alkyl, $C_{1-6}$ haloalkyl, $C_{1-6}$ alkoxy, $C_{1-6}$ haloalkoxy, $C_{3-7}$ cycloalkyl, 3-10 membered heterocycloalkyl, $C_{6-10}$ aryl, 5-10 membered heteroaryl, —$C_{1-4}$ alkyl-($C_{3-7}$ cycloalkyl), —$C_{1-4}$ alkyl-(3-10 membered heterocycloalkyl), —$N(R^7)(R^8)$, —$N(R^7)(C(=O)R^8)$, —$N(R^7)(C(=O)—OR^8)$, —$N(R^7)(C(=O)—N(R^8)(R^9))$, —C(=O)—$N(R^7)(R^8)$, —C(=O)—$R^7$, —C(=O)—$OR^7$, —OC(=O)$R^7$, —$N(R^7)(S(=O)_2R^8)$, and —$S(=O)_2$—$N(R^7)(R^8)$, wherein the —S—$C_{1-4}$ alkyl, $C_{1-6}$ alkyl, $C_{1-6}$ haloalkyl, $C_{1-6}$ alkoxy, $C_{1-6}$ haloalkoxy, $C_{3-7}$ cycloalkyl, 3-10 membered heterocycloalkyl, $C_{6-10}$ aryl, 5-10 membered heteroaryl, —$C_{1-4}$ alkyl-($C_{3-7}$ cycloalkyl), and —$C_{1-4}$ alkyl-(3-10 membered heterocycloalkyl) are each optionally substituted with 0, 1, 2, 3 or 4 substitutes each independently selected from a group consisting of halogen, —OH, —$NH_2$, —$NH(CH_3)$, —$N(CH_3)_2$, —CN, —$NO_2$, —$SF_5$, —SH, —S—$C_{1-4}$ alkyl, oxo, $C_{1-4}$ alkyl, $C_{2-6}$ alkenyl, $C_{2-6}$ alkynyl, $C_{3-7}$ cycloalkyl, $C_{1-4}$ hydroxyalkyl, —S—$C_{1-4}$ alkyl, —C(=O)H, —C(=O)—$C_{1-4}$ alkyl, —C(=O)—O—$C_{1-4}$ alkyl, —C(=O)—$NH_2$, —C(=O)—N($C_{1-4}$ alkyl)$_2$, $C_{1-4}$ haloalkyl, $C_{1-4}$ alkoxy and $C_{1-4}$ haloalkoxy; and $R^7$, $R^8$, and $R^9$, at each occurrence, are each are each independently selected from a group consisting of: H, $C_{1-6}$ alkyl, $C_{1-4}$ haloalkyl, $C_{3-7}$ cycloalkyl, 3-10 membered heterocycloalkyl, $C_{6-10}$ aryl, 5-10 membered heteroaryl, ($C_{3-7}$ cycloalkyl)-$C_{1-4}$ alkyl-, (3-10 membered heterocycloalkyl)-$C_{1-4}$ alkyl-, ($C_{6-10}$ aryl)-$C_{1-4}$ alkyl- and (5-10 membered heteroaryl)-$C_{1-4}$ alkyl-, wherein each substituent listed in the group is optionally substituted with 0, 1, 2, 3, or 4 substituents each independently selected from a group consisting of: halogen, —OH, —$NH_2$, —$NH(CH_3)$, —$N(CH_3)_2$, —CN, —$NO_2$, —$SF_5$, —SH, —S—$C_{1-4}$ alkyl, oxo, $C_{1-4}$ alkyl, $C_{2-6}$ alkenyl, $C_{2-6}$ alkynyl, $C_{3-7}$ cycloalkyl, $C_{1-4}$ hydroxyalkyl, —S—$C_{1-4}$ alkyl, —C(═O)H, —C(═O)—$C_{1-4}$ alkyl, —C(═O)—O—$C_{1-4}$ alkyl, —C(═O)—$NH_2$, —C(═O)—N($C_{1-4}$ alkyl)$_2$, $C_{1-4}$ haloalkyl, $C_{1-4}$ alkoxy and $C_{1-4}$ haloalkoxy;

or $R^7$, $R^8$, and the atoms attached thereto together form a 3-14-membered ring;

or $R^8$, $R^9$, and the atoms attached thereto together form a 3-14-membered ring.

In some embodiments, each $R^5$ is independently selected from H, halogen, —OH, —$NO_2$, —CN, —$SF_5$, —SH, —S—$C_{1-4}$ alkyl, $C_{1-6}$ alkyl, $C_{1-6}$ alkoxy, $C_{1-6}$ haloalkoxy, $C_{2-8}$ alkenyl, $C_{2-8}$ alkynyl, $C_{3-7}$ cycloalkyl, 3-10 membered heterocycloalkyl, —$C_{1-4}$ alkyl-($C_{3-7}$ cycloalkyl), —$C_{1-4}$ alkyl-(3-10 membered heterocycloalkyl), $C_{5-7}$ aryl, 5-7 membered heteroaryl, $C_{7-11}$ bicycloaryl, 7-11 membered bicycloheteroaryl, —$N(R^7)(R^8)$, —$N(R^7)(C(═O)R^8)$, —C(═O)—$N(R^7)(R^8)$, —C(═O)—$R^7$, —C(═O)—$OR^7$, —OC(═O)$R^7$, —$N(R^7)(S(═O)_2R^8)$, —S(═O)$_2$—N($R^7$)($R^8$), —$SR^7$, and —$OR^7$, wherein the —S—$C_{1-4}$ alkyl, $C_{1-6}$ alkyl, $C_{1-6}$ alkoxy, $C_{1-6}$ haloalkoxy, $C_{2-8}$ alkenyl, $C_{2-8}$ alkynyl, $C_{3-7}$ cycloalkyl, 3-10 membered heterocycloalkyl, —$C_{1-4}$ alkyl-($C_{3-7}$ cycloalkyl), —$C_{1-4}$ alkyl-(3-10 membered heterocycloalkyl), $C_{5-7}$ aryl, 5-7 membered heteroaryl, $C_{7-11}$ bicycloaryl, 7-11 membered bicycloheteroaryl are each optionally substituted with 0, 1, 2, 3 or 4 substitutes each independently selected from a group consisting of halogen, —CN, —OH, $C_{1-4}$ alkyl, $C_{1-4}$ alkoxy, $C_{1-4}$ haloalkyl, $C_{1-4}$ haloalkoxy, $C_{3-6}$ cycloalkyl, —$N(R^7)(R^8)$, —$N(R^7)(C(═O)R^8)$, —C(═O)—$N(R^7)(R^8)$, —C(═O)—$R^7$, —C(═O)—$OR^7$, —OC(═O)$R^7$, —$N(R^7)(S(═O)_2R^8)$, —S(═O)$_2$—N($R^7$)($R^8$), —$SR^7$ and —$OR^7$; in which $R^7$ and $R^8$, at each occurrence, are each are each independently selected from a group consisting of: H, $C_{1-6}$ alkyl, $C_{1-4}$ haloalkyl, $C_{3-7}$ cycloalkyl, 3-10 membered heterocycloalkyl, $C_{6-10}$ aryl, 5-10 membered heteroaryl, ($C_{3-7}$ cycloalkyl)-$C_{1-4}$ alkyl-, (3-10 membered heterocycloalkyl)-$C_{1-4}$ alkyl-, ($C_{6-10}$ aryl)-$C_{1-4}$ alkyl- and (5-10 membered heteroaryl)-$C_{1-4}$ alkyl-, wherein each substituent listed in the group is optionally substituted with 0, 1, 2, 3, or 4 substituents each independently selected from a group consisting of: halogen, —OH, —$NH_2$, —$NH(CH_3)$, —$N(CH_3)_2$, —CN, —$NO_2$, —$SF_5$, —SH, —S—$C_{1-4}$ alkyl, oxo, $C_{1-4}$ alkyl, $C_{2-6}$ alkenyl, $C_{2-6}$ alkynyl, $C_{3-7}$ cycloalkyl, $C_{1-4}$ hydroxyalkyl, —S—$C_{1-4}$ alkyl, —C(═O)H, —C(═O)—$C_{1-4}$ alkyl, —C(═O)—O—$C_{1-4}$ alkyl, —C(═O)—$NH_2$, —C(═O)—N($C_{1-4}$ alkyl)$_2$, $C_{1-4}$ haloalkyl, $C_{1-4}$ alkoxy and $C_{1-4}$ haloalkoxy; or $R^7$, $R^8$, and the atoms attached thereto together form a 3-14-membered ring.

In some embodiments, $R^5$ is 3-10 membered heterocycloalkyl. For example, $R^5$ may be selected from azetidinyl, thietidinyl, dihydrofuranyl, dihydrothienyl, tetrahydrothienyl, tetrahydrofuranyl, tetrahydrotriazinyl, tetrahydropyrazolyl, tetrahydrooxazinyl, tetrahydropyrimidinyl, octahydrobenzofuranyl, octahydrobenzimidazolyl, octahydrobenzothiazolyl, imidazolidinyl, pyrrolidinyl, piperidinyl, piperazinyl, oxazolidinyl, thiazolidinyl, pyrazolidinyl, thiomorpholinyl, tetrahydropyranyl, tetrahydrothiopyranyl, tetrahydrothiazinyl, tetrahydrothiadiazinyl, tetrahydrooxazolyl, morpholinyl, oxetanyl, tetrahydrodiazinyl, oxazinyl, oxathiadiazinyl, quinuclidinyl, benzodipyranyl, isobenzodipyranyl, dihydrobenzodioxinyl, benzodioxopentenyl, benzoxazinyl, dihydro indolyl, dihydrobenzofuranyl, tetrahydroquinolinyl, isochromanyl, dihydro-1H-isoindolyl, oxepanyl, thiepanyl, and azepanyl. The above 3-10-membered heterocycloalkyl may optionally be substituted with 1, 2, 3, 4 or more substituents each independently selected from a group consisting of: halogen, —CN, —OH, $C_{1-4}$ alkyl, $C_{1-4}$ alkoxy, $C_{1-4}$ haloalkyl, $C_{1-4}$ haloalkoxy, $C_{3-6}$ cycloalkyl, —$N(R^7)(R^8)$, —$N(R^7)(C(═O)R^8)$, —C(═O)—$N(R^7)(R^8)$, —C(═O)—$R^7$, —C(═O)—$OR^7$, —OC(═O)$R^7$, —$N(R^7)(S(═O)_2R^8)$, —S(═O)$_2$—N($R^7$)($R^8$), —$SR^7$ and —$OR^7$, wherein $R^7$ and $R^8$ are as defined above.

In some embodiments, $R^5$ is $C_{1-6}$ alkyl. For example $R^5$ is selected from methyl, ethyl, propyl, isopropyl, butyl, isobutyl, sec-butyl, tert-butyl, pentyl, 2-pentyl, 3-pentyl, isopentyl, neopentyl, (R)-2-methylbutyl, (S)-2-methylbutyl, 3-methylbutyl, 2,3-dimethylpropyl, 2,3-dimethylbutyl, and hexyl. The $C_{1-6}$ alkyl may optionally be substituted with 1, 2, 3, 4 or more substituents each independently selected from a group consisting of: halogen, —CN, —OH, $C_{1-4}$ alkyl, $C_{1-4}$ alkoxy, $C_{1-4}$ haloalkyl, $C_{1-4}$ haloalkoxy, $C_{3-6}$ cycloalkyl, —$N(R^7)(R^8)$, —$N(R^7)(C(═O)R^8)$, —C(═O)—$N(R^7)(R^8)$, —C(═O)—$R^7$, —C(═O)—$OR^7$, —OC(═O)$R^7$, —$N(R^7)(S(═O)_2R^8)$, —S(═O)$_2$—N($R^7$)($R^8$), —$SR^7$ and —$OR^7$, wherein $R^7$ and $R^8$ are as defined above.

In some embodiments, $R^5$ is $C_{3-7}$ cycloalkyl. For example $R^5$ is selected from cyclopropyl, cyclobutyl, cyclopentyl, cyclohexyl, cyclohexenyl, cycloheptyl, cyclohexadienyl, cyclopentenyl, and cycloheptenyl. The $C_{3-7}$ cycloalkyl may optionally be substituted with 1, 2, 3, 4 or more substituents each independently selected from a group consisting of: halogen, —CN, —OH, $C_{1-4}$ alkyl, $C_{1-4}$ alkoxy, $C_{1-4}$ haloalkyl, $C_{1-4}$ haloalkoxy, $C_{3-6}$ cycloalkyl, —$N(R^7)(R^8)$, —$N(R^7)(C(═O)R^8)$, —C(═O)—$N(R^7)(R^8)$, —C(═O)—$R^7$, —C(═O)—$OR^7$, —OC(═O)$R^7$, —$N(R^7)(S(═O)_2R^1)$, —S(═O)$_2$—N($R^7$)($R^8$), —$SR^7$ and —$OR^7$, wherein $R^7$ and $R^8$ are as defined above.

In some preferred embodiments, $R^5$ is selected from piperazinyl, morpholinyl, pyrrolidinyl, piperidinyl, and azetidinyl. The piperazinyl, morpholinyl, pyrrolidinyl, piperidinyl, and azetidinyl may optionally be substituted with 0, 1, or 2 substituents each independently selected from a group consisting of: methyl, ethyl, cyclopentyl, cyclopropyl, —CN, and —OH. For example, in some preferred embodiments, $R^5$ is selected from 3,5-dimethylpiperazinyl, morpholinyl, 3-hydroxypyrrolidinyl, 4-methylpiperazinyl, 4-ethylpiperazinyl, 4-hydroxypiperidinyl, 1-methylpiperidinyl, 1-ethylpiperidin-4-yl, and 1-methylazetidin-3-yl.

In some preferred embodiments, $R^5$ is selected from methyl, ethyl, propyl, isopropyl, and cyclobutyl groups. The methyl, ethyl, propyl, isopropyl or cyclobutyl group may optionally be substituted with 0, 1 or 2 substituents each independently selected from a group consisting of: methyl, ethyl, cyclopentyl, cyclopropyl, —CN, —OH, morpholinyl, piperidinyl, and these substituents may further optionally be substituted with 0, 1 or 2 substituents each independently selected from a group consisting of: methyl, ethyl, cyclopentyl, cyclopropyl, —CN, and —OH. For example, in some preferred embodiments, $R^5$ is selected from (1-hydroxycyclopropyl)ethyl, 3-hydroxycyclobutyl, 2-cyanoethyl, 2-hydroxyethyl, 2-cyano-1-cyclopentyl ethyl, 1-cyanopropane, 2-morpholinoethyl, ethyl, and (1-methylpiperidin-4-yl)methyl.

In some preferred embodiments, $R^5$ is selected from halogen, such as F.

In some preferred embodiments, one $R^5$ is present.

In some preferred embodiments, two $R^5$(s) are present. In some preferred embodiments, two $R^5$(s) are present, wherein one $R^5$ is selected from piperazinyl, morpholinyl, pyrrolidinyl, piperidinyl and azetidinyl, the piperazinyl, morpholinyl, pyrrolidinyl, piperidinyl and azetidinyl being optionally substituted with 0, 1 or 2 substituents each independently selected from a group consisting of: methyl, ethyl, cyclopentyl, cyclopropyl, —CN, and —OH; and wherein the other $R^5$ is selected from halogen. In some preferred embodiments, two $R^5$(s) are present, wherein one $R^5$ is selected from methyl, ethyl, propyl, isopropyl, and cyclobutyl groups, in which said methyl, ethyl, propyl, isopropyl or cyclobutyl groups may optionally be substituted with 0, 1 or 2 substituents each independently selected from a group consisting of: methyl, ethyl, cyclopentyl, cyclopropyl, —CN, —OH, morpholinyl, and piperidinyl, and these substituents are further optionally substituted with 0, 1 or 2 substituents each independently selected from a group consisting of: methyl, ethyl, cyclopentyl, cyclopropyl, —CN, and —OH; and wherein the other $R^5$ is selected from halogen.

It should be understood that any of the above embodiments of $R^5$ may be combined with any of the embodiments of $R^1$, $R^2$, $R^3$, $R^4$, A, $R^6$, $R^7$, and $R^8$ as described above and below.

In some embodiments, the compound described in the present application is a compound selected from formula (II), formula (III), formula (IV) and formula (V), or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof, (II)

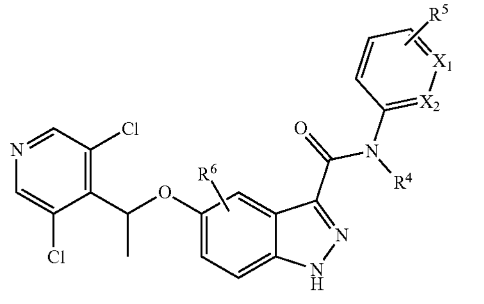

(III)

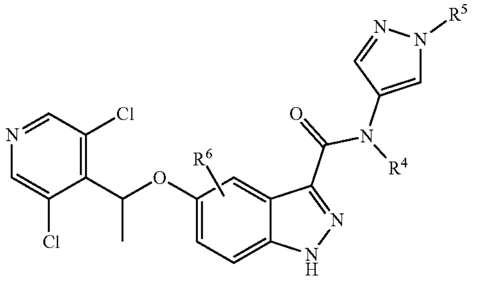

-continued (IV)

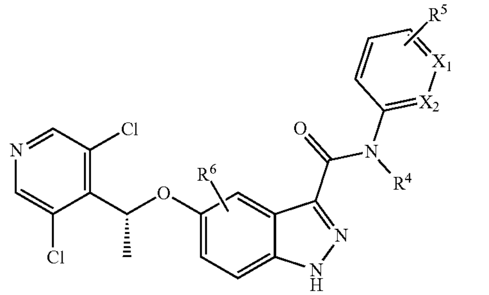

(V)

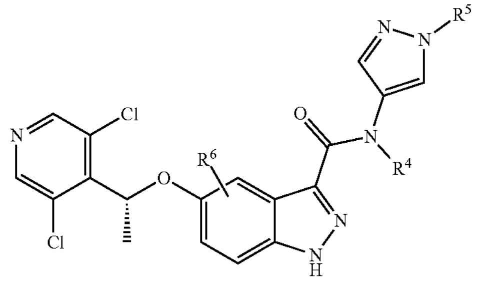

wherein $R_4$ is selected from H, $C_{1-3}$ alkyl, $C_{1-3}$ haloalkyl, $C_{1-3}$ alkoxy, $C_{3-6}$ cycloalkyl and 4-6 membered heterocycloalkyl; and 0, 1, 2, 3, 4, 5, 6, 7, or 8 $R^5$(s) are present, and each $R^5$ is independently selected from H, halogen, —OH, —$NO_2$, —CN, —$SF_5$, —SH, —S—$C_{1-4}$ alkyl, $C_{1-6}$ alkyl, $C_{1-6}$ haloalkyl, $C_{1-6}$ alkoxy, $C_{1-6}$ haloalkoxy, $C_{2-8}$ alkenyl, $C_{2-8}$ alkynyl, $C_{3-7}$ cycloalkyl, 3-10 membered heterocycloalkyl, $C_{6-12}$ bicycloalkyl, 6-12 membered bicycloheteroalkyl, $C_{8-15}$ tricycloalkyl, 8-15 membered tricycloheteroalkyl, $C_{5-8}$ aryl, 5-7 membered heteroaryl, $C_{7-11}$ bicycloaryl, 7-11 membered bicycloheteroaryl, —$C_{1-4}$ alkyl-($C_{3-7}$ cycloalkyl), —$C_{1-4}$ alkyl-(3-10 membered heterocycloalkyl), —$C_{1-4}$ alkyl-($C_{6-12}$ bicycloalkyl), —$C_{1-4}$ alkyl-(6-12 membered bicycloheteroalkyl), —$C_{1-4}$ alkyl-($C_{8-15}$-tricycloalkyl), —$C_{1-4}$ alkyl-(8-15 membered tricycloheteroalkyl), —N($R^7$)($R^8$), —N($R^7$)(C(═O)$R^8$), —N($R^7$)(C(═O)—O$R^8$), —N($R^7$)(C(═O)—N($R^8$)($R^9$)), —C(═O)—N($R^7$)($R^8$), —C(═O)—$R^7$, —C(═O)—O$R^7$, —OC(═O)$R^7$, —N($R^7$)(S(═O)$_2R^8$), —S(═O)$_2$—N($R^7$)($R^8$), —S$R^7$, and —O$R^7$, wherein the —S—$C_{1-4}$ alkyl, $C_{1-6}$ alkyl, $C_{1-6}$ alkoxy, $C_{1-6}$ haloalkoxy, $C_{2-8}$ alkenyl, $C_{2-8}$ alkynyl, $C_{3-7}$ cycloalkyl, 3-10 membered heterocycloalkyl, $C_{6-12}$ bicycloalkyl, 6-12 membered bicycloheteroalkyl, $C_{8-15}$ tricycloalkyl, 8-15 membered tricycloheteroalkyl, $C_{5-8}$ aryl, 5-7 membered heteroaryl, $C_{7-11}$ bicycloaryl, 7-11 membered bicycloheteroaryl, —$C_{1-4}$ alkyl-($C_{3-7}$ cycloalkyl), —$C_{1-4}$ alkyl-(3-10 membered heterocycloalkyl), —$C_{1-4}$ alkyl-($C_6$-12 bicycloalkyl), —$C_{1-4}$ alkyl-(6-12 membered bicycloheteroalkyl), —$C_{1-4}$ alkyl-($C_{8-15}$ tricycloalkyl), and —$C_{1-4}$ alkyl-(8-15 membered tricycloheteroalkyl) are each optionally substituted with 0, 1, 2, 3 or 4 $R^{5a}$.

$R^{5a}$ is independently selected from H, halogen, —OH, —$NO_2$, —CN, —$SF_5$, —SH, —S—$C_{1-4}$ alkyl, $C_{1-6}$ alkyl, $C_{1-6}$ haloalkyl, $C_{1-6}$ alkoxy, $C_{1-6}$ haloalkoxy, $C_{2-8}$ alkenyl, $C_{2-8}$ alkynyl, $C_{3-7}$ cycloalkyl, 3-10 membered heterocycloalkyl, $C_{6-12}$ bicycloalkyl, 6-12 membered bicycloheteroalkyl, $C_{8-15}$ tricycloalkyl, 8-15 membered tricycloheteroalkyl, $C_{5-8}$ aryl, 5-7 membered heteroaryl, $C_{7-11}$ bicycloaryl, 7-11 membered bicycloheteroaryl, —$C_{1-4}$ alkyl-($C_{3-7}$ cycloalkyl), —$C_{1-4}$ alkyl-(3-10 membered heterocycloalkyl), —$C_{1-4}$ alkyl-($C_{6-12}$ bicycloalkyl), —$C_{1-4}$ alkyl-(6-12 membered bicycloheteroalkyl), —N($R^7$)($R^8$), —N($R^7$)(C(═O)$R^8$), —N($R^7$)(C(═O)—O$R^8$), —N($R^7$)(C(═O)—N($R^8$)($R^9$)), —C(═O)—N($R^7$)($R^8$), —C(═O)—$R^7$, —C(═O)—O$R^7$, —OC(═O)$R^7$, —N($R^7$)(S(═O)$_2$ $R^8$), —S(═O)$_2$—N($R^7$)($R^8$), —S$R^7$, and —O$R^7$, wherein the —S—$C_{1-4}$ alkyl, $C_{1-6}$ alkyl, $C_{1-6}$ haloalkyl, $C_{1-6}$ alkoxy, $C_{1-6}$ haloalkoxy, $C_{2-8}$ alkenyl, $C_{2-8}$ alkynyl, $C_{3-7}$ cycloalkyl, 3-10 membered heterocycloalkyl, $C_{6-12}$ bicycloalkyl, 6-12 membered bicycloheteroalkyl, $C_{8-15}$ tricycloalkyl, 8-15 membered tricycloheteroalkyl, $C_{5-8}$ aryl, 5-7 membered heteroaryl, $C_{7-11}$ bicycloaryl, 7-11 membered bicycloheteroaryl, —$C_{1-4}$ alkyl-($C_{3-7}$ cycloalkyl), —$C_{1-4}$ alkyl-(3-10 membered heterocycloalkyl), —$C_{1-4}$ alkyl-($C_{6-12}$ bicycloalkyl) and —$C_{1-4}$ alkyl-(6-12 membered bicycloheteroalkyl) are each optionally substituted with 0, 1, 2, 3 or 4 $R^{5b}$;

$R^{5b}$ is independently selected from H, halogen, —OH, —CN, —$NO_2$, —$SF_5$, —SH, —S—$C_{1-4}$ alkyl, oxo, $C_{1-6}$ alkyl, $C_{1-6}$ haloalkyl, $C_{1-6}$ alkoxy, $C_{1-6}$ haloalkoxy, $C_{3-7}$ cycloalkyl, 3-10 membered heterocycloalkyl, $C_{6-10}$ aryl, 5-10 membered heteroaryl, —$C_{1-4}$ alkyl-($C_{3-7}$ cycloalkyl), —$C_{1-4}$ alkyl-(3-10 membered heterocycloalkyl), —N($R^7$)($R^8$), —N($R^7$)(C(═O)$R^8$), —N($R^7$)(C(═O)—O$R^8$), —N($R^7$)(C(═O)—N($R^8$)($R^9$)), —C(═O)—N($R^7$)($R^8$), —C(═O)—$R^7$, —C(═O)—O$R^7$, —OC(═O)$R^7$, —N($R^7$)(S(═O)$_2$ $R^8$), and —S(═O)$_2$—N($R^7$)($R^8$), wherein the —S—$C_{1-4}$ alkyl, $C_{1-6}$ alkyl, $C_{1-6}$ haloalkyl, $C_{1-6}$ alkoxy, $C_{1-6}$ haloalkoxy, $C_{3-7}$ cycloalkyl, 3-10 membered heterocycloalkyl, $C_{6-10}$ aryl, 5-10 membered heteroaryl, —$C_{1-4}$ alkyl-($C_{3-7}$ cycloalkyl), and —$C_{1-4}$ alkyl-(3-10 membered heterocycloalkyl) are each optionally substituted with 0, 1, 2, 3 or 4 substitutes each independently selected from a group consisting of halogen, —OH, —$NH_2$, —NH($CH_3$), —N($CH_3$)$_2$, —CN, —$NO_2$, —$SF_5$, —SH, —S—$C_{1-4}$ alkyl, oxo, $C_{1-4}$ alkyl, $C_{2-6}$ alkenyl, $C_{2-6}$ alkynyl, $C_{3-7}$ cycloalkyl, $C_{1-4}$ hydroxyalkyl, —S—$C_{1-4}$ alkyl, —C(═O)H, —C(═O)—$C_{1-4}$ alkyl, —C(═O)—O—$C_{1-4}$ alkyl, —C(═O)—$NH_2$, —C(═O)—N($C_{1-4}$ alkyl)$_2$, $C_{1-4}$ haloalkyl, $C_{1-4}$ alkoxy and $C_{1-4}$ haloalkoxy; and 0, 1, 2, or 3 $R^6$(s) are present, and each $R^6$ is independently selected from H, halogen, —CN, —$NO_2$, $C_{1-3}$ alkyl, $C_{1-3}$ haloalkyl, $C_{1-3}$ alkoxy, $C_{3-6}$ cycloalkyl, and 4-6 membered heterocycloalkyl, and $R^7$, $R^8$, and $R^9$, at each occurrence, are each are each independently selected from a group consisting of: H, $C_{1-6}$ alkyl, $C_{1-4}$ haloalkyl, $C_{3-7}$ cycloalkyl, 3-10 membered heterocycloalkyl, $C_{6-10}$ aryl, 5-10 membered heteroaryl, ($C_{3-7}$ cycloalkyl)-$C_{1-4}$ alkyl-, (3-10 membered heterocycloalkyl)-$C_{1-4}$ alkyl-, ($C_{6-10}$ aryl)-$C_{1-4}$ alkyl- and (5-10 membered heteroaryl)-$C_{1-4}$ alkyl-, wherein each substituent listed in the group is optionally substituted with 0, 1, 2, 3, or 4 substituents each independently selected from a group consisting of: halogen, —OH, —$NH_2$, —NH($CH_3$), —N($CH_3$)$_2$, —CN, —$NO_2$, —$SF_5$, —SH, —S—$C_{1-4}$ alkyl, oxo, $C_{1-4}$ alkyl, $C_{2-6}$ alkenyl, $C_{2-6}$ alkynyl, $C_{3-7}$ cycloalkyl, $C_{1-4}$ hydroxyalkyl, —S—$C_{1-4}$ alkyl, —C(═O)H, —C(═O)—$C_{1-4}$ alkyl, —C(═O)—O—$C_{1-4}$ alkyl, —C(═O)—$NH_2$, —C(═O)—N($C_{1-4}$ alkyl)$_2$, $C_{1-4}$ haloalkyl, $C_{1-4}$ alkoxy and $C_{1-4}$ haloalkoxy;

or $R^7$, $R^8$, and the atoms attached thereto together form a 3-14-membered ring;

or $R^8$, $R^9$, and the atoms attached thereto together form a 3-14-membered ring.

$X_1$ and $X_2$ are each independently selected from —CH, N and C in the case of being directly connected with $R^5$.

The embodiments and preference for $R^4$, $R^5$ and $R^6$ given above for formula (I) are equally applicable to formula (II), formula (III), formula (IV) and formula (V).

In some embodiments, in formula (I) as described above, $R^1$ and $R^2$ are both Cl; $R^3$ is methyl; $R^4$ is H; $R^6$ is H; A is phenyl; one $R^5$ is present and is selected from methyl, azetidinyl, piperazinyl, morpholinyl, pyrrolidinyl, piperidinyl, ethyl, propyl, isopropyl, cyclobutyl groups, in which said azetidinyl, piperazinyl, morpholinyl, pyrrolidinyl, piperidinyl, ethyl, propyl, isopropyl, and cyclobutyl groups may optionally be substituted with 0, 1 or 2 substituents each independently selected from a group consisting of: methyl, ethyl, cyclopentyl, cyclopropyl, —CN, —OH, morpholinyl, piperidinyl, and these substituents may further optionally be substituted with 0, 1 or 2 substituents each independently selected from a group consisting of: methyl, ethyl, cyclopentyl, cyclopropyl, —CN, and —OH.

In some embodiments, in formula (I) as described above, $R^1$ and $R^2$ are both Cl; $R^3$ is methyl; $R^4$ is H; $R^6$ is H; A is pyridine; one $R^5$ is present and is selected from methyl, azetidinyl, piperazinyl, morpholinyl, pyrrolidinyl, piperidinyl, ethyl, propyl, isopropyl, cyclobutyl groups, in which said azetidinyl, piperazinyl, morpholinyl, pyrrolidinyl, piperidinyl, ethyl, propyl, isopropyl, and cyclobutyl group may optionally be substituted with 0, 1 or 2 substituents each independently selected from a group consisting of: methyl, ethyl, cyclopentyl, cyclopropyl, —CN, —OH, morpholinyl, and piperidinyl, and these substituents may further optionally be substituted with 0, 1 or 2 substituents each independently selected from a group consisting of: methyl, ethyl, cyclopentyl, cyclopropyl, —CN, and —OH.

In some embodiments, in formula (I) as described above, $R^1$ and $R^2$ are both Cl; $R^3$ is methyl; $R^4$ is H; $R^6$ is H; A is pyridazine; and one $R^5$ is present and is selected from methyl, azetidinyl, piperazinyl, morpholinyl, pyrrolidinyl, piperidinyl, ethyl, propyl, isopropyl, and cyclobutyl groups, in which said azetidinyl, piperazinyl, morpholinyl, pyrrolidinyl, piperidinyl, ethyl, propyl, isopropyl, and cyclobutyl group may optionally be substituted with 0, 1 or 2 substituents each independently selected from a group consisting of: methyl, ethyl, cyclopentyl, cyclopropyl, —CN, —OH, morpholinyl, and piperidinyl, and these substituents may further optionally be substituted with 0, 1 or 2 substituents each independently selected from a group consisting of: methyl, ethyl, cyclopentyl, cyclopropyl, —CN, and —OH.

In some embodiments, in formula (I) as described above, $R^1$ and $R^2$ are both Cl; $R^3$ is methyl; $R^4$ is H; $R^6$ is H; A is pyrazole; and one $R^5$ is present and is selected from methyl, azetidinyl, piperazinyl, morpholinyl, pyrrolidinyl, piperidinyl, ethyl, propyl, isopropyl, cyclobutyl groups, in which said azetidinyl, piperazinyl, morpholinyl, pyrrolidinyl, piperidinyl, ethyl, propyl, isopropyl, and cyclobutyl group may optionally be substituted with 0, 1 or 2 substituents each independently selected from a group consisting of: methyl, ethyl, cyclopentyl, cyclopropyl, —CN, —OH, morpholinyl, and piperidinyl, and these substituents may further optionally be substituted with 0, 1 or 2 substituents each independently selected from a group consisting of: methyl, ethyl, cyclopentyl, cyclopropyl, —CN, and —OH.

In some embodiments, in formula (I) as described above, both $R^1$ and $R^2$ are Cl; $R^3$ is methyl; $R^4$ is H; $R^6$ is H; A is benzene; and two $R^5$(s) are present in which one $R^5$ is selected from methyl, azetidinyl, piperazinyl, morpholinyl, pyrrolidinyl, piperidinyl, ethyl, propyl, isopropyl, and cyclobutyl groups, in which said azetidinyl, piperazinyl, morpholinyl, pyrrolidinyl, piperidinyl, ethyl, propyl, isopropyl, and cyclobutyl group may optionally be substituted with 0, 1 or 2 substituents each independently selected from a group consisting of: methyl, ethyl, cyclopentyl, cyclopropyl, —CN, —OH, morpholinyl, and piperidinyl, and these substituents may further optionally be substituted with 0, 1 or 2 substituents each independently selected from a group consisting of: methyl, ethyl, cyclopentyl, cyclopropyl, —CN, and —OH; and the other $R^5$ is selected from halogen.

In some embodiments, in formula (I) as described above, $R^1$ and $R^2$ are both Cl; $R^3$ is methyl; $R^4$ is H; $R^6$ is H; A is pyridine; and two $R^5$(s) are present in which one $R^5$ is selected from methyl, azetidinyl, piperazinyl, morpholinyl, pyrrolidinyl, piperidinyl, ethyl, propyl, isopropyl, and cyclobutyl groups, in which said azetidinyl, piperazinyl, morpholinyl, pyrrolidinyl, piperidinyl, ethyl, propyl, isopropyl, and cyclobutyl group may optionally be substituted with 0, 1 or 2 substituents each independently selected from a group consisting of: methyl, ethyl, cyclopentyl, cyclopropyl, —CN, —OH, morpholinyl, and piperidinyl, and these substituents may further optionally be substituted with 0, 1 or 2 substituents each independently selected from a group consisting of: methyl, ethyl, cyclopentyl, cyclopropyl, —CN, and —OH; and the other $R^5$ is selected from halogen.

In some embodiments, in formula (I) as described above, both $R^1$ and $R^2$ are Cl; $R^3$ is methyl; $R^4$ is H; $R^6$ is H; A is pyridazine; and two $R^5$(s) are present in which one $R^5$ is selected from methyl, azetidinyl, piperazinyl, morpholinyl, pyrrolidinyl, piperidinyl, ethyl, propyl, isopropyl, and cyclobutyl groups, in which said azetidinyl, piperazinyl, morpholinyl, pyrrolidinyl, piperidinyl, ethyl, propyl, isopropyl, and cyclobutyl group may optionally be substituted with 0, 1 or 2 substituents each independently selected from a group consisting of: methyl, ethyl, cyclopentyl, cyclopropyl, —CN, —OH, morpholinyl, and piperidinyl, and these substituents may further optionally be substituted with 0, 1 or 2 substituents each independently selected from a group consisting of: methyl, ethyl, cyclopentyl, cyclopropyl, —CN, and —OH; and the other $R^5$ is selected from halogen.

In some embodiments, in formula (I) as described above, both $R^1$ and $R^2$ are Cl; $R^3$ is methyl; $R^4$ is H; $R^6$ is H; A is pyrazole; and two $R^5$(s) are present in which one $R^5$ is selected from methyl, azetidinyl, piperazinyl, morpholinyl, pyrrolidinyl, piperidinyl, ethyl, propyl, isopropyl, and cyclobutyl groups, in which said azetidinyl, piperazinyl, morpholinyl, pyrrolidinyl, piperidinyl, ethyl, propyl, isopropyl, and cyclobutyl group may optionally be substituted with 0, 1 or 2 substituents each independently selected from a group consisting of: methyl, ethyl, cyclopentyl, cyclopropyl, —CN, —OH, morpholinyl, and piperidinyl, and these substituents may further optionally be substituted with 0, 1 or 2 substituents each independently selected from a group consisting of: methyl, ethyl, cyclopentyl, cyclopropyl, —CN, and —OH; and the other $R^5$ is selected from halogen.

In some embodiments, the compounds according to the present application are selected from:

5-(1-(3,5-dichloropyridin-4-yl)ethoxy)-N-(4-((3S,5R)-3,5-dimethylpiperazin-1-yl)phenyl)-1H-indazole-3-carboxamide, 5-(1-(3,5-dichloropyridin-4-yl)ethoxy)-N-(1-(2-hydroxyethyl)-1H-pyrazol-4-yl)-1H-indazole-3-carboxamide, 5-(1-(3,5-dichloropyridin-4-yl)ethoxy)-N-(4-((R)-3-hydroxypyrrolidin-1-yl)phenyl)-1H-indazole-3-carboxamide, 5-(1-(3,5-dichloropyridin-4-yl)ethoxy)-N-(6-morpholinopyridin-3-yl)-1H-indazole-3-carboxamide, N-(1-(1-cyanopropan-2-yl)-1H-pyrazol-4-yl)-5-(1-(3,5-dichloropyridin-4-yl)ethoxy)-1H-indazole-3-carboxamide, 5-((R)-1-(3,5-dichloropyridin-4-yl)ethoxy)-N-(4-((3S,5R)-3,5-dimethylpiperazin-1-yl)phenyl)-1H-indazole-3-carboxamide, (R)-5-(1-(3,5-dichloropyridin-4-yl)ethoxy)-N-(1-(2-hydroxyethyl)-1H-pyrazol-4-yl)-1H-indazole-3-carboxamide, 5-(1-(3,5-dichloropyridin-4-yl)ethoxy)-N-(6-((3S,5R)-3,5-dimethylpiperazin-1-yl) pyridin-3-yl)-1H-indazole-3-carboxamide, 5-(1-(3,5-dichloropyridin-4-yl)ethoxy)-N-(4-(4-methylpiperazin-1-yl)phenyl)-1H-indazole-3-carboxamide, 5-(1-(3,5-dichloropyridin-4-yl)ethoxy)-N-(4-(4-ethylpiperazin-1-yl)phenyl)-1H-indazole-3-carboxamide, N-(1-(2-cyanoethyl)-1H-pyrazol-4-yl)-5-(1-(3,5-dichloropyridin-4-yl)ethoxy)-1H-indazole-3-carboxamide, 5-(1-(3,5-dichloropyridin-4-yl)ethoxy)-N-(1-(3-hydroxycyclobutyl)-1H-pyrazol-4-yl)-1H-indazole-3-carboxamide, 5-(1-(3,5-dichloropyridin-4-yl)ethoxy)-N-(4-(4-hydroxypiperidin-1-yl)phenyl)-1H-indazole-3-carboxamide, 5-(1-(3,5-dichloropyridin-4-yl)ethoxy)-N-(1-(1-methylpiperidin-4-yl)-1H-pyrazol-4-yl)-1H-indazole-3-carboxamide, 5-(1-(3,5-dichloropyridin-4-yl)ethoxy)-N-(1-(2-(1-hydroxycyclopropyl)ethyl)-1H-pyrazol-4-yl)-1H-indazole-3-carboxamide, 5-(1-(3,5-dichloropyridin-4-yl)ethoxy)-N-(5-((3S,5R)-3,5-dimethylpiperazin-1-yl) pyridin-2-yl)-1H-indazole-3-carboxamide, 5-(1-(3,5-dichloropyridin-4-yl)ethoxy)-N-(4-((3S, 5R)-3,5-dimethylpiperazin-1-yl)-3-fluorophenyl)-1H-indazole-3-carboxamide, 5-(1-(3,5-dichloropyridin-4-yl)ethoxy)-N-(4-(1-ethylpiperidin-4-yl)phenyl)-1H-indazole-3-carboxamide, 5-(1-(3,5-dichloropyridin-4-yl)ethoxy)-N-(1-(2-morpholinoethyl)-1H-pyrazol-4-yl)-1H-indazole-3-carboxamide, 5-(1-(3,5-dichloropyridin-4-yl)ethoxy)-N-(1-ethyl-1H-pyrazol-4-yl)-1H-indazole-3-carboxamide, 5-(1-(3,5-dichloropyridin-4-yl)ethoxy)-N-(1-(1-methylazetidin-3-yl)-1H-pyrazol-4-yl)-1H-indazole-3-carboxamide, 5-(1-(3,5-dichloropyridin-4-yl)ethoxy)-N-(1-(((1-methylpiperidin-4-yl)methyl)-1H-pyrazol-4-yl)-1H-indazole-3-carboxamide, 5-(1-(3,5-dichloropyridin-4-yl)ethoxy)-N-(1-(2-oxo-2-(pyrrolidin-1-yl)ethyl)-1H-pyrazol-4-yl)-1H-indazole-3-carboxamide, 5-(1-(3,5-dichloropyridin-4-yl)ethoxy)-N-(1-(2-(dimethylamino)-2-oxoethyl)-1H-pyrazol-4-yl)-1H-indazole-3-carboxamide, 5-(1-(3,5-dichloropyridin-4-yl)ethoxy)-N-(1-(2-(pyrrolidin-1-yl)ethyl)-1H-pyrazol-4-yl)-1H-indazole-3-carboxamide, 5-(1-(3,5-dichloropyridin-4-yl)ethoxy)-N-(1-isopropyl-1H-pyrazol-4-yl)-1H-indazole-3-carboxamide, N-(1-cyclobutyl-1H-pyrazol-4-yl)-5-(1-(3,5-dichloropyridin-4-yl)ethoxy)-1H-indazole-3-carboxamide, 5-(1-(3,5-dichloropyridin-4-yl)ethoxy)-N-(1-(2,2,2-trifluoroethyl)-1H-pyrazol-4-yl)-1H-indazole-3-carboxamide, 5-(1-(3,5-dichloropyridin-4-yl)ethoxy)-N-(1-(3-hydroxypropyl)-1H-pyrazol-4-yl)-1H-indazole-3-carboxamide, 5-(1-(3,5-dichloropyridin-4-yl)ethoxy)-N-(4-(morpholinomethyl)phenyl)-1H-indazole-3-carboxamide,
(R)-5-(1-(3,5-dichloropyridin-4-yl)ethoxy)-N-(1-(1-ethylazetidin-3-yl)-1H-pyrazol-4-yl)-1H-indazole-3-carboxamide,
5-((R)-1-(3,5-dichloropyridin-4-yl)ethoxy)-N-(1-((S)-2-hydroxypropyl)-1H-pyrazol-4-yl)-1H-indazole-3-carboxamide,
5-((R)-1-(3,5-dichloropyridin-4-yl)ethoxy)-N-(1-((R)-2-hydroxypropyl)-1H-pyrazol-4-yl)-1H-indazole-3-carboxamide,
(R)-5-(1-(3,5-dichloropyridin-4-yl)ethoxy)-N-(1-ethyl-1H-pyrazol-4-yl)-1H-indazole-3-carboxamide,
(R)-5-(1-(3,5-dichloropyridin-4-yl)ethoxy)-N-(1-(3-hydroxycyclobutyl)-1H-pyrazol-4-yl)-1H-indazole-3-carboxamide,
(R)-5-(1-(3,5-dichloropyridin-4-yl)ethoxy)-N-(1-(2-(dimethylamino)ethyl)-1H-pyrazol-4-yl)-1H-indazole-3-carboxamide,
(R)-5-(1-(3,5-dichloropyridin-4-yl)ethoxy)-N-(1-(2-morpholinoethyl)-1H-pyrazol-4-yl)-1H-indazole-3-carboxamide,
(R)-5-(1-(3,5-dichloropyridin-4-yl)ethoxy)-N-(1-(2-hydroxy-2-methylpropyl)-1H-pyrazol-4-yl)-1H-indazole-3-carboxamide,
(R)-5-(1-(3,5-dichloropyridin-4-yl)ethoxy)-N-(1-((1-ethylazetidin-3-yl)methyl)-1H-pyrazol-4-yl)-1H-indazole-3-carboxamide,
(R)-5-(1-(3,5-dichloropyridin-4-yl)ethoxy)-N-(1-((1-ethylpiperidin-4-yl)methyl)-1H-pyrazol-4-yl)-1H-indazole-3-carboxamide,
5-((R)-1-(3,5-dichloropyridin-4-yl)ethoxy)-N-(1-((1-methylpyrrolidin-3-yl)methyl)-1H-pyrazol-4-yl)-1H-indazole-3-carboxamide,
5-((R)-1-(3,5-dichloropyridin-4-yl)ethoxy)-N-(1-((1-methylpyrrolidin-2-yl)methyl)-1H-pyrazol-4-yl)-1H-indazole-3-carboxamide,
5-((R)-1-(3,5-dichloropyridin-4-yl)ethoxy)-N-(1-(1-methylpyrrolidin-3-yl)-1H-pyrazol-4-yl)-1H-indazole-3-carboxamide,
5-((R)-1-(3,5-dichloropyridin-4-yl)ethoxy)-N-(1-((1-methylpiperidin-3-yl)methyl)-1H-pyrazol-4-yl)-1H-indazole-3-carboxamide,
5-((R)-1-(3,5-dichloropyridin-4-yl)ethoxy)-N-(1-((1-methylpiperidin-2-yl)methyl)-1H-pyrazol-4-yl)-1H-indazole-3-carboxamide,
5-(1-(3,5-dichloropyridin-4-yl)propoxy)-N-(1-methyl-1H-pyrazol-4-yl)-1H-indazole-3-carboxamide,
(R)-5-(1-(3,5-dichloropyridin-4-yl)ethoxy)-N-(1-(tetrahydro-2H-pyran-4-yl)-1H-pyrazol-4-yl)-1H-indazole-3-carboxamide,
(R)-5-(1-(3,5-dichloropyridin-4-yl)ethoxy)-N-(1-(4-hydroxycyclohexyl)-1H-pyrazol-4-yl)-1H-indazole-3-carboxamide,
(R)-5-(1-(3,5-dichloropyridin-4-yl)ethoxy)-N-(1-(pyridin-3-ylmethyl)-1H-pyrazol-4-yl)-1H-indazole-3-carboxamide,
(R)-5-(1-(3,5-dichloropyridin-4-yl)ethoxy)-N-(1-(pyridin-4-ylmethyl)-1H-pyrazol-4-yl)-1H-indazole-3-carboxamide, and
(R)-5-(1-(3,5-dichloropyridin-4-yl)ethoxy)-N-(1-((1-methylazetidin-3-yl)methyl)-1H-pyrazol-4-yl)-1H-indazole-3-carboxamide.

The compounds according to the present application can be synthesized via conventional organic synthesis methods according to their specific structures by those skilled in the art.

Synthetic route (I)

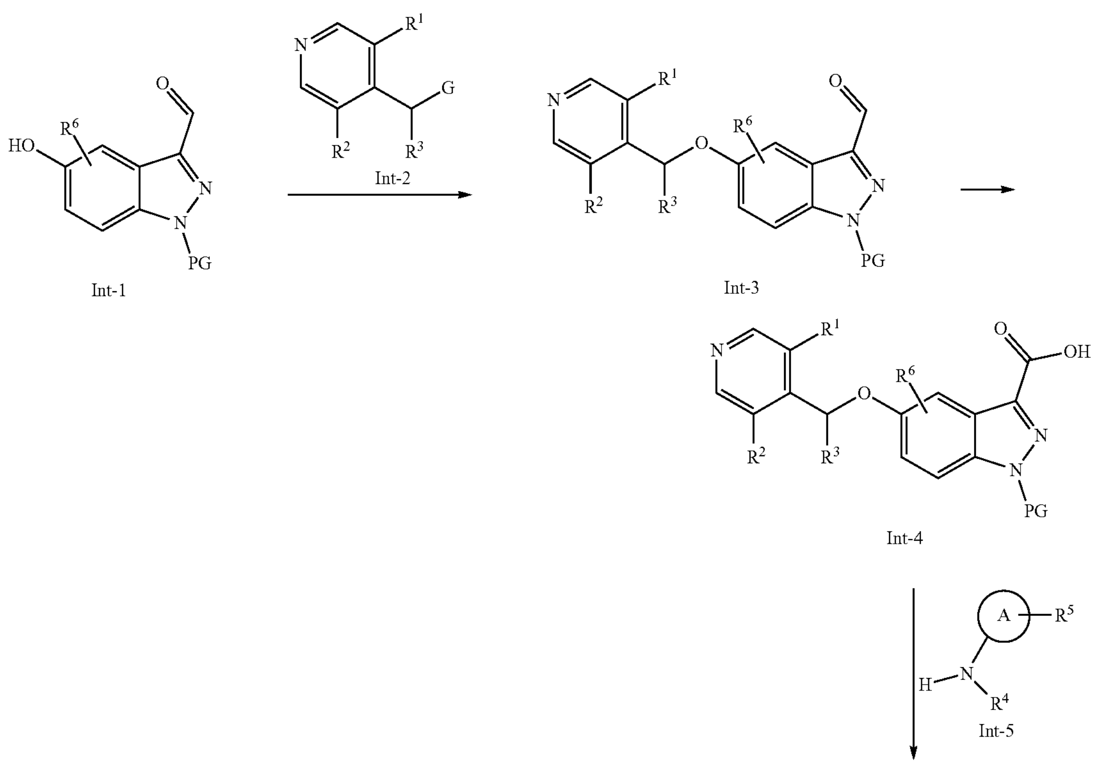

-continued

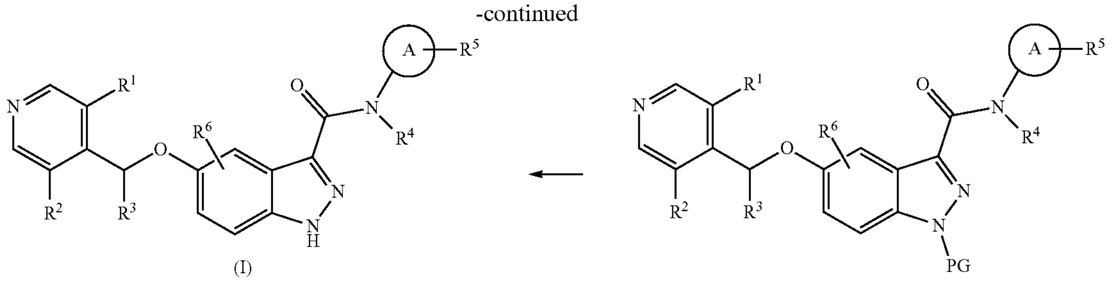

(I)

Int-6

For example, compounds of formula (I) can be prepared by the method shown in synthetic route (I) above. G in an intermediate Int-2 is selected from halogen, hydroxyl, methylsulfonyl (OMs), p-toluenesulfonyl (OTs), and the like. PG is an amino protecting group such as tetrahydropyran (THP), benzyl (Bn), p-methoxybenzyl (PMB), and the like. When G is halogen, OMs, or OTs, the SN2 coupling reaction between intermediates Int-1 and Int-2 under a basic condition can produce an intermediate Int-3. When G is OH, the intermediate Int-3 can be obtained by the Mitsunobu reaction between Int-1 and Int-2. In the presence of an oxidizing reagent (e.g., but not limited to KMnO4), the aldehyde group in the Int-3 is converted to a carboxylic acid to produce an intermediate Int-4. Under a typical amidogenic reaction condition (e.g., but not limited to in the presence of DIPEA/HATU), the reaction of Int-4 with Int-5 can produce an amide Int-6. Under a suitable deprotection condition, the Int-6 can be converted to the target compound of formula (I). In addition, a person skilled in the art can refer to the synthetic routes of specific compounds shown in examples of the present application and make appropriate adjustments to the raw materials and reaction conditions to obtain synthesis methods of other compounds.

The compounds according to the present application can inhibit activities of FGFR. For example, the compounds according to the present application can be used to selectively inhibit activities of FGFR1 and/or FGFR2 and/or FGFR3 and/or FGFR4 and/or their mutants (e.g., gatekeeper mutants such as FGFR1 V561M mutant, FGFR2 V564F mutant, FGFR3 V555M mutant, FGFR3 K650E mutant, etc.) in cells or in individuals or patients requiring inhibition of FGFR, which is achieved by administering an inhibitory amount of a compound according to the present application to the cells, individuals or patients.

In some embodiments, the compounds according to the present application have excellent inhibitory activity against FGFR1, FGFR2, FGFR3, and their gatekeeper mutants (e.g., the FGFR1 V561M mutant, the FGFR2 V564F mutant, and the FGFR3 V555M mutant of FGFR).

The term "gatekeeper mutation" as used herein has the meaning commonly known in the art, which is a mutation that prevents drug binding and can lead to the development of drug resistance. The gatekeeper mutants of FGFRs comprise, but not limited to, FGFR1 V561M, FGFR2 V564F, FGFR2 V564I, FGFR2 N550K, FGFR2 V565I, FGFR3 V555M, FGFR4 V550L, FGFR4 V550M, FGFR4 V555M, FGFR4 V555L and others.

In a second aspect, the present application provides a pharmaceutical composition comprising a compound according to the present application, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof, as described above, and one or more pharmaceutically acceptable carriers, adjuvants, or excipients.

The pharmaceutical compositions according to the present application can be prepared in a manner well known in the pharmaceutical field and can be administered by a variety of routes, depending on whether topical or systemic treatment is desired and depending on the site to be treated. Administration can be topical (including ophthalmic and to mucous membranes, including intranasal, vaginal, and rectal delivery), pulmonary (e.g., by inhalation or by blowing in a powder or aerosol, including through aerosol dispensers; intratracheal, intranasal, epidermal, and transdermal), ocular, transoral, or parenteral. Methods for ocular delivery may include topical administration (eye drops), subconjunctival, periocular or intravitreal injection or introduction via a balloon catheter or ophthalmic insert surgically placed in the conjunctival sac. Parenteral administration includes intravenous, intra-arterial, subcutaneous, intraperitoneal, or intramuscular injection or infusion; or intracranial (e.g., intrathecal or intracerebroventricular) administration. Parenteral administration can be in the form of a single push dose, or can be, for example, via a continuous perfusion pump. Pharmaceutical compositions and formulations for topical administration may include transdermal patches, ointments, lotions, creams, gels, drops, suppositories, sprays, liquids, and powders.

If a solid carrier is used, the dosage may be tableted, or placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the dosage may be in the form of a syrup, emulsion, paste, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. The medicament are prepared by conventional techniques appropriate to the desired preparation containing appropriate amounts of the active ingredient, that is, the compound according to the invention.

Medicament dosage suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil), and injectable organic esters such as ethyl oleate.

The medicament may also contain excipients such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well-known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylatedisostearyl alcohols, polyoxyethylene sorbitol and sorbitan esters, microcrystalline cellulose, meta-aluminum hydroxide, bentonite, agar-agar and tragacanth, or mixtures of these substances, and the like.

Dosage forms for topical administration of a compound of the invention include paste, powders, sprays, and inhalants. The active component is admixed under sterile conditions with a physiologically acceptable carrier and any preservatives, buffers, or propellants as may be required.

The amount of the compound according to the present application in the pharmaceutical composition and dosage form can be appropriately determined by those skilled in the art as needed. For example, the compound according to the present application can be present in the pharmaceutical composition or dosage form in a therapeutically effective amount.

In a third aspect, the present application provides use of the compounds according to the present application, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof, as described above, or the pharmaceutical composition as described above, in the preparation of drugs for the treatment of diseases or conditions associated with FGFR.

The present application also provides a method of treating diseases or conditions associated with FGFR, said method comprising administering to a patient in need thereof a therapeutically effective amount of a compound according to the present application, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof, as described above, or the pharmaceutical composition as described above. Said patient is preferably a mammal, more preferably a human patient. The route of administration may be oral, topical (including, but not limited to, topical application, spraying, and the like), parenteral (including subcutaneous, intramuscular, cortical and intravenous) administration, bronchial administration, or nasal administration, etc.

In some embodiments, said disease or condition associated with FGFR is a cancer. The compound according to the present application may be used, for example, to inhibit proliferation, metastasis, and the like of cancer cells.

Exemplary cancers include bladder cancer, breast cancer, cervical cancer, colorectal cancer, small bowel cancer, colon cancer, rectal cancer, anal cancer, endometrial cancer, head and neck cancer (e.g., cancers of larynx, laryngopharynx, nasopharynx, oropharynx, lips, and mouth), kidney cancer, liver cancer (e.g., hepatocellular carcinoma, bile duct cell carcinoma), lung cancer (e.g., adenocarcinoma, small cell lung cancer, and non-small cell lung cancer, small cell cancer and non-small cell cancer, bronchial cancer, bronchial adenoma, pleural pneumoblastoma), ovarian cancer, prostate cancer, testicular cancer, uterine cancer, esophageal cancer, gallbladder cancer, pancreatic cancer (e.g., exocrine pancreatic cancer), thyroid cancer, parathyroid cancer, skin cancer (e.g., squamous cell carcinoma, Kaposi's sarcoma, Merkel cell skin cancer), and brain cancer (e.g., stellate cell tumor, neural tube embryonal cell tumor, ventricular meningioma, neuroectodermal tumor, pineal gland tumor).

Additional exemplary cancers include hematopoietic malignancies such as leukemia or lymphoma, multiple myeloma, chronic lymphocytic lymphoma, adult T-cell leukemia, B-cell lymphoma, cutaneous T-cell lymphoma, acute myelogenous leukemia, Hodgkin or non-Hodgkin lymphoma, myeloproliferative neoplasms (e.g., true erythroblastosis, primary thrombocythemia, and primary myelofibrosis), Waldenstrom's macroglobulinemia, hairy cell lymphoma, chronic myelogenous lymphoma, acute lymphoblastic lymphoma, AIDS-related lymphoma, and Burkitt's lymphoma.

Additional exemplary cancers include eye tumors, glioblastoma, melanoma, rhabdomyosarcoma, lymphosarcoma, and osteosarcoma.

In some preferred embodiments, said diseases or conditions associated with FGFR are selected from hepatocellular carcinoma, breast cancer, bladder cancer, colorectal cancer, melanoma, mesothelioma, lung cancer, prostate cancer, membrane adenocarcinoma, testicular cancer, thyroid cancer, squamous cell carcinoma, glioblastoma, neuroblastoma, uterine cancer, and rhabdomyosarcoma.

In some other embodiments, said diseases or conditions associated with FGFR are selected from skeletal disorders and chondrocyte disorders, such skeletal disorders and chondrocyte disorders including, but not limited to, chondrodysplasia, hypochondrogenesis, dwarfism, lethal chondrodysplasia (TD)(clinical forms TD I and TD II), Apert syndrome, Crouzon syndrome, Jackson-Weiss syndrome, Beare-Stevenson cutis gyrate syndrome, Pfeiffer syndrome, and cranial suture closure premature syndrome.

In other embodiments, said diseases or conditions associated with FGFR are hypophosphatemic disorder, said hypophosphatemic disorder including, for example, X-linked hypophosphatemic rickets, autosomal recessive hypophosphatemic rickets, autosomal dominant hypophosphatemic rickets, and tumor-induced osteromalacia.

In some other embodiments, said diseases or conditions associated with FGFR are selected from fibrotic diseases. Exemplary fibrotic diseases include cirrhosis, glomerulonephritis, pulmonary fibrosis, systemic fibrosis, rheumatoid arthritis, and wound healing.

In some embodiments, said diseases or conditions associated with FGFR are diseases and conditions that are resistant to FGFR inhibitors that do not target gatekeeper mutatants of FGFR due to gatekeeper mutations in FGFR.

The present application is further described and illustrated below in connection with specific examples.

EXAMPLES

The following examples set forth herein are for illustrative purposes only, to exemplify aspects of the invention and the manner in which they are to be carried out, and are not intended to limit in any way the scope of protection as claimed.

Unless otherwise stated, all reactants were obtained from commercial sources. The instruments and equipment used in the synthesis experiments and product analysis are all conventional instruments and equipment normally used in organic synthesis.

Example 1: synthesis of 5-(1-(3,5-dichloropyridin-4-yl)ethoxy)-N-(4-((3S,5R)-3,5-dimethylpiperazin-1-yl)phenyl)-1H-indazole-3-carboxamide (1)

1

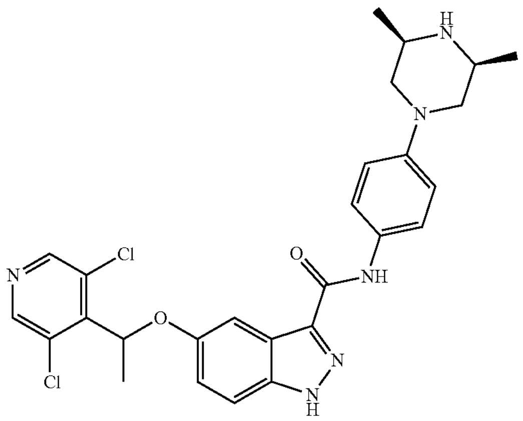

Synthetic Route of Compound 1:

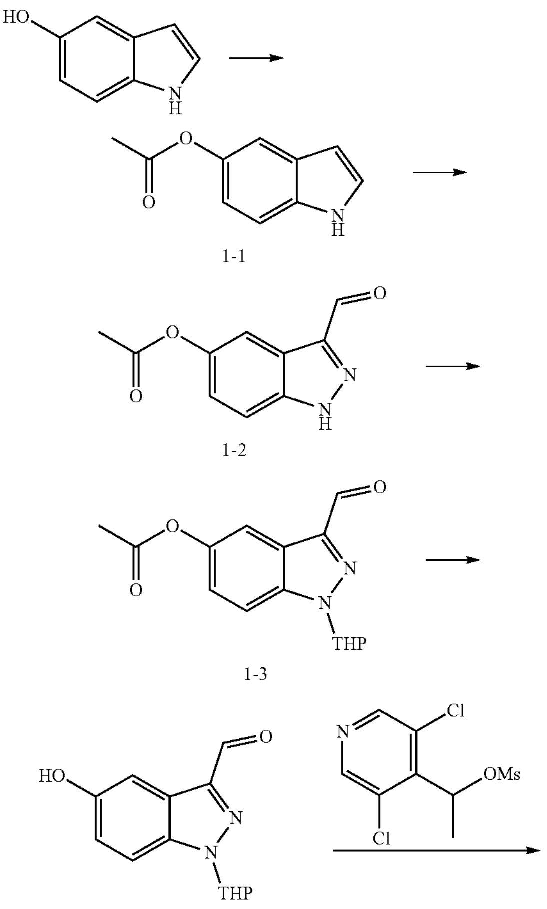

1-1

1-2

1-3

1-4

-continued

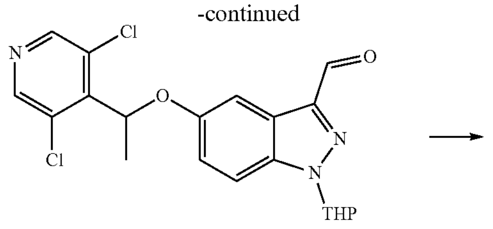

1-5

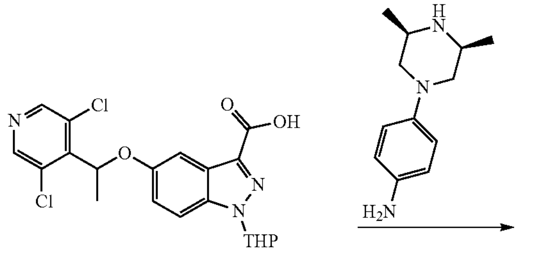

1-6

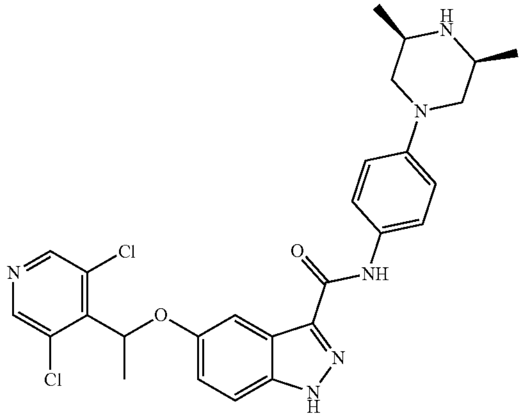

1

Synthesis Method:

Synthesis of Intermediate 1-1: 1H-indole-5-acetate 5-hydroxyindole (240.0 mg, 1.80 mmol) was dissolved in 20 ml of pyridine, to which acetic anhydride (202.4 mg, 1.98 mmol) was added dropwise and the resulting mixture was stirred for 16 h at room temperature. Water was added to the reaction solution, and the resulting mixture was extracted twice with ethyl acetate. The resulting organic phases were combined, washed with saturated salt water, dried with anhydrous sodium sulfate, and concentrated to afford 276.6 mg of the crude intermediate 111 with a yield of 87.4%.

Synthesis of Intermediate 1-2: 3-formyl-1H-indazole-5-acetate

Sodium nitrite (157.5 mg, 2.28 mmol) was dissolved in 10 ml of water, to which 10 ml of DMF was added, and 3M HCl (0.7 ml, 2.05 mmol) was added dropwise at 0 degree. The resulting mixture was stirred for 10 min. To the reaction solution, 1H-indole-5-acetate (50.0 mg, 0.29 mmol) in DMF (10 ml) was added and reacted for 3 h at room temperature. Water was added to the reaction solution, and the resulting mixture was extracted twice with ethyl acetate. The resulting organic phases were combined, washed with saturated salt water, dried with anhydrous sodium sulfate, concentrated and purified by silica gel column to give 37.6 mg of Intermediates 1-2 with a yield of 63.5%.

$^1$H NMR (400 MHz, $CDCl_3$) δ 10.25 (s, 1H), 8.01 (s, 1H), 7.49 (d, J=9.0 Hz, 1H), 7.21 (d, J=9.0 Hz, 1H), 2.36 (s, 3H).

Synthesis of Intermediate 1-3: 3-formyl-1-(tetrahydro-2H-pyran-2-yl)-1H-indazole-5-acetate 1-2 (190.0 mg, 0.93 mmol) was dissolved in 20 ml of DCM, to which p-toluenesulfonic acid (177.0 mg, 0.93 mmol) was added, and the mixture was stirred for 2 min. To the reaction solution, 3,4-dihydro-2H-pyran (117.4 mg, 1.40 mmol) in DCM (3 ml) was added and the reaction was carried out at room temperature for 1 h. Water was added to the reaction solution, and the resulting mixture was extracted twice with DCM. The resulting organic phases were combined, washed with saturated sodium bicarbonate solution and saturated salt water, dried over anhydrous sodium sulfate, concentrated and purified by silica gel column to give 160.2 mg of Intermediate 1-3 with a yield of 59.6%.

Synthesis of Intermediate 1-4: 5-hydroxy-1-(tetrahydro-2H-pyran-2-yl)-1H-indazole-3-carbaldehyde 1-3 (160.2 mg, 0.56 mmol) was dissolved in 20 ml of methanol, to which potassium carbonate (115.1 mg, 0.83 mmol) was added. The reaction was carried out at room temperature for 30 min. The reaction solution was filtered and the filtrate was concentrated to afford 130.5 mg of crude intermediate 1-4 with a yield of 95.1%.

Synthesis of Intermediate 1-5: 5-(1-(3,5-dichloropyridin-4-yl)ethoxy)-1-(tetrahydro-2H-pyran-2-yl)-1H-indazole-3-carbaldehyde 1-(3,5-dichloropyridin-4-yl)ethan-1-ol (93.6 mg, 0.49 mmol) and triethylamine (148.6 mg, 1.47 mmol) were dissolved in 20 ml DCM, to which methanesulfonyl chloride (57.3 mg, 0.50 mmol) was added dropwise at 0° C. The reaction was carried out for 1 h at room temperature. The reaction solution was quenched with water, and extracted twice with dichloromethane, and the organic phases were combined, washed with saturated saline, dried over anhydrous sodium sulfate and concentrated. 1-4 (100.0 mg, 0.41 mmol) and the concentrate were dissolved in 20 ml DMF, to which cesium carbonate (264.6 mg, 0.82 mmol) was added, and the reaction was carried out at 60 degrees for 16 hours. To the reaction solution water was added and the resulting mixture was extracted with ethyl acetate twice. The resulting organic phases were combined, washed with saturated saline, dried over anhydrous sodium sulfate, concentrated and purified by silica gel column to give 64.3 mg of Intermediate 1-5 with a yield of 37.5%.

$^1$H NMR (400 MHz, $CDCl_3$) δ 10.16 (s, 1H), 8.42 (s, 2H), 7.59-7.53 (m, 2H), 7.18-7.15 (m, 1H), 6.11 (q, J=6.7 Hz, 1H), 5.77-5.72 (m, 1H), 4.01-3.94 (m, 1H), 3.77-3.70 (m, 1H), 2.54-2.46 (m, 1H), 2.22-2.06 (m, 2H), 1.81 (d, J=6.7 Hz, 3H), 1.76-1.68 (m, 3H).

Synthesis of Intermediate 1-6: 5-(1-(3,5-dichloropyridin-4-yl)ethoxy)-1-(tetrahydro-2H-pyran-2-yl)-1H-indazole-3-carboxylic acid (24.0 mg, 0.06 mmol) was dissolved in 12 ml of acetonitrile and 4 ml of water, to which potassium permanganate (18.1 mg, 0.12 mmol) was added and the reaction was carried out for 16 h at room temperature. The reaction solution was filtered through diatomaceous earth, and the filtrate was adjusted to pH 3 with 3M hydrochloric acid, and extracted twice with dichloromethane. The resulting organic phases were combined, washed with saturated salt water, dried over anhydrous sodium sulfate, concentrated, and purified by silica gel column to give 16.3 mg of Intermediate 1-6 with a yield of 64.2%.

$^{1}$H NMR (400 MHz, $CDCl_3$) δ 8.46 (s, 2H), 7.60-7.57 (m, 1H), 7.50 (s, 1H), 7.16 (d, J=9.1 Hz, 1H), 6.11 (q, J=6.7 Hz, 1H), 5.77-5.72 (m, 1H), 4.01-3.98 (m, 1H), 3.74-3.71 (m, 1H), 2.54-2.46 (m, 1H), 2.07-2.04 (m, 2H), 1.82 (d, J=6.7 Hz, 3H), 1.76-1.66 (m, 3H).

Synthesis of compound 1: 5-(1-(3,5-dichloropyridin-4-yl)ethoxy)-N-(4-((3S,5R)-3,5-dimethylpiperazin-1-yl)phenyl)-1H-indazole-3-carboxamide 1-6 (20.0 mg, 0.05 mmol) and 4-((3S,5R)-3,5-dimethylpiperazin-1-yl)aniline (11.3 mg, 0.06 mmol) were dissolved in 10 ml DMF, to which HATU (20.9 mg, 0.06 mmol) and DIPEA (17.8 mg, 0.12 mmol) were added and it was allowed to react for 3 h at room temperature. Water was added to the reaction solution and the resulting mixture was extracted twice with ethyl acetate. The resulting organic phases were combined, washed with saturated salt water, dried over anhydrous sodium sulfate and concentrated. The concentrate was dissolved in 6 ml of methanol, to which 3 ml of concentrated hydrochloric acid was added, and it was allowed to react at 50 degrees for 1 h. The reaction solution was concentrated, and dissolved in 5 ml of methanol, to which 0.5 ml of ammonia was added, and the resulting mixture was concentrated, and purified by a preparative plate to afford 1.2 mg of the final product, with a yield of 50.8%.

$^{1}$H NMR (400 MHz, DMSO-$d_6$) δ 13.65 (s, 1H), 10.04 (s, 1H), 8.60 (s, 2H), 7.73-7.70 (m, 2H), 7.56 (d, J=9.0 Hz, 1H), 7.50 (s, 1H), 7.17-7.14 (m, 1H), 7.00 (d, J=8.8 Hz, 2H), 6.07 (q, J=6.6 Hz, 1H), 3.78 (d, J=12.7 Hz, 2H), 3.31 (s, 2H), 2.67-2.58 (m, 2H), 1.75 (d, J=6.6 Hz, 3H), 1.27-1.23 (m, 6H).

Example 2: Synthesis of 5-(1-(3,5-dichloropyridin-4-yl)ethoxy)-N-(1-(2-hydroxyethyl)-1H-pyrazol-4-yl)-1H-indazole-3-carboxamide (2)

2

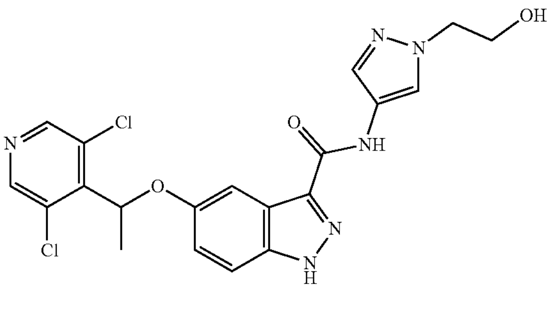

Synthesis Method:
Synthetic Route of Compound 2:

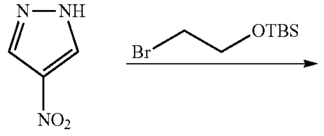

-continued

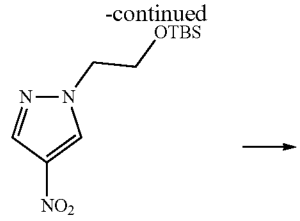

2-1

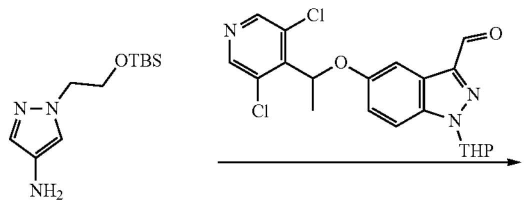

2-2

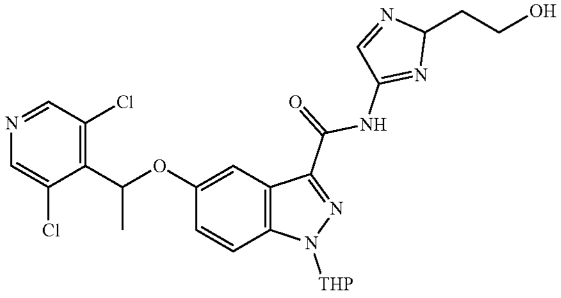

2

Synthesis of Intermediate 2-1: 1-(2-((tert-butyldimethylsilyl)oxy)ethyl)-4-nitro-1H-pyrazole 4-Nitro-1H-pyrazole (200 mg, 1.77 mmol) was dissolved in 25 ml of acetonitrile, to which potassium carbonate (733 mg, 5.31 mmol) and (2-bromoethoxy)-tert-butyldimethylsilane (508 mg, 2.12 mmol) were added. The resulting mixture was heated to 80 degrees to allow the reaction to proceed. After the reaction was completed, 50 ml of water was added to the system, and the reaction solution was extracted with ethyl acetate (EA), and partitioned, and the organic phase was washed with saturated salt water, dried over anhydrous sodium sulfate, and concentrated by column chromatography to afford 470 mg of Intermediate 2-1 with a yield of 97.9%.

$^{1}$H NMR (400 MHz, $CDCl_3$) δ 8.20 (s, 1H), 8.07 (s, 1H), 4.24 (t, J=4.9 Hz, 2H), 3.95 (t, J=4.9 Hz, 2H), 0.83 (s, 9H), −0.04 (s, 6H).

Synthesis of Intermediate 2-2: 1-(2-((tert-butyldimethylsilyl)oxy)ethyl)-1H-pyrazol-4-amine Intermediate 2-1 (450 mg, 1.66 mmol) was dissolved in 10 ml of methanol, to which 10% Pd/C (45 mg) was added, and the atmosphere was replaced with hydrogen gas three times. It was allowed to react at room temperature. After the reaction was completed, the system was filtered and concentrated to give 390 mg of intermediate 2-2 with a yield of 97.4%.

Synthesis of compound 2: 5-(1-(3,5-dichloropyridin-4-yl)ethoxy)-N-(1-(2-hydroxyethyl)-1H-pyrazol-4-yl)-1H-indazole-3-carboxamide Intermediate 1-6 (30.0 mg, 0.069 mmol) was dissolved in 4 ml DMF, to which HATU (28.8 mg, 0.076 mmol) and DIPEA (17.8 mg, 0.138 mmol) were added and the resulting mixture was stirred for one hour at room temperature. And then, to the system, the intermediate 2-2 (16.7 mg, 0.069 mmol) was added. After the addition was completed, it was allowed to react at room temperature. After the reaction was completed, the system was quenched with water, and extracted twice with ethyl acetate, and the resulting organic phases were combined, washed with saturated salt water, dried over anhydrous sodium sulfate, and concentrated. The resulting residue was dissolved with 4 ml of methanol, then 2 ml of concentrated hydrochloric acid was added and it was allowed to react at 50° C. After the reaction was completed, the reaction solution was evaporated under reduced pressure, and the residue was dissolved with 2 ml of methanol and neutralized with 0.5 ml of ammonia. After the neutralization was completed, the compound was purified by column chromatography to afford 14.0 mg of compound 2 with a yield of 44.1%.

$^1$H NMR (400 MHz, DMSO-$d_6$) δ 13.62 (s, 1H), 10.42 (s, 1H), 8.60 (s, 2H), 8.06 (s, 1H), 7.66 (s, 1H), 7.55 (d, J=5.2 Hz, 1H), 7.54 (s, 1H), 7.15 (dd, J=2.3, 9.1 Hz, 1H), 6.09 (q, J=6.6 Hz, 1H), 4.12 (t, J=5.6 Hz, 2H), 3.95 (t, J=5.6 Hz, 2H), 1.76 (d, J=6.6 Hz, 3H).

Example 3: Synthesis of 5-(1-(3,5-dichloropyridin-4-yl)ethoxy)-N-(4-((R)-3-hydroxypyrrolidin-1-yl)phenyl)-1H-indazole-3-carboxamide (3)

3

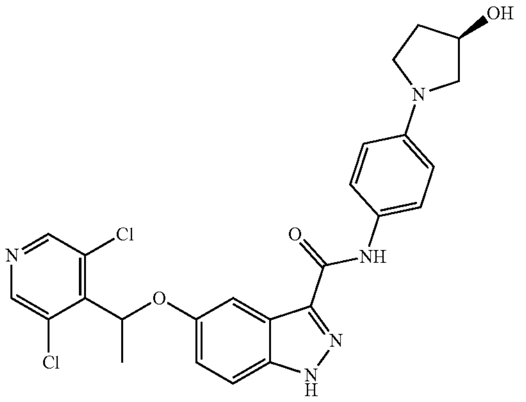

Synthetic Route of Compound 3:

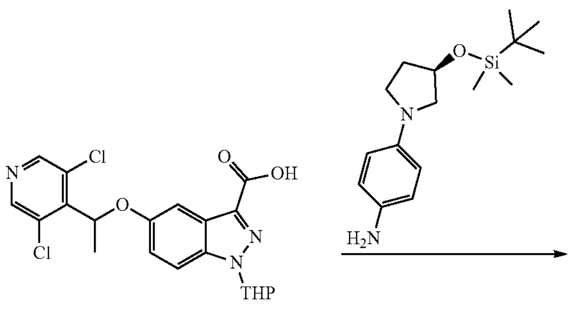

1-6

-continued

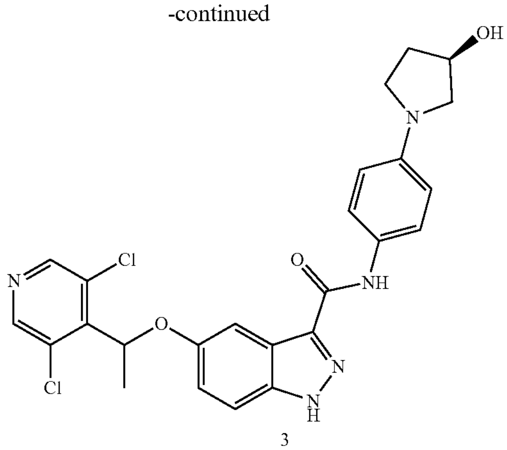

3

Synthesis Method:

Synthesis of compound 3: 5-(1-(3,5-dichloropyridin-4-yl)ethoxy)-N-(4-((R)-3-hydroxypyrrolidin-1-yl)phenyl)-1H-indazole-3-carboxamide 1-6 (25.0 mg, 0.06 mmol) and (R)-4-(3-((tert-butyldimethylsilyl)oxy) pyrrolidin-1-yl)aniline (25.2 mg, 0.09 mmol) were dissolved in 10 ml DMF, then HATU (32.7 mg, 0.09 mmol) and DIPEA (22.2 mg, 0.17 mmol) were added to the solution and it was allowed to react for 3 h at room temperature. Water was added to the reaction solution and the mixture was extracted twice with ethyl acetate, and the resulting organic phases were combined, washed with saturated salt water, dried over anhydrous sodium sulfate and concentrated. The concentrate was dissolved in 6 ml of methanol, to which 3 ml of concentrated hydrochloric acid was added, it was allowed to react at 50° C. for 1 h, and the reaction solution was concentrated. The concentrate was dissolved in 5 ml of methanol, neutralized with 0.5 ml of ammonia, concentrated, and purified by a preparative plate to afford 11.5 mg of the final product with a yield of 63.8%.

$^1$H NMR (400 MHz, DMSO-$d_6$) δ 13.57 (s, 1H), 9.83 (s, 1H), 8.60 (s, 2H), 7.62-7.50 (m, 4H), 7.15-7.13 (m, 1H), 6.51-6.49 (m, 2H), 6.07 (q, J=6.6 Hz, 1H), 4.41 (s, 1H), 3.43-3.23 (m, 3H), 3.08-3.05 (m, 1H), 2.09-1.95 (m, 1H), 1.92-1.86 (m, 1H), 1.75 (d, J=6.6 Hz, 3H).

Example 4: Synthesis of 5-(1-(3,5-dichloropyridin-4-yl)ethoxy)-N-(6-morpholinopyridin-3-yl)-1H-indazole-3-carboxamide (4)

4

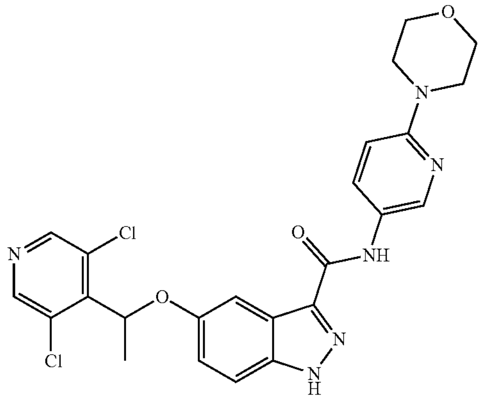

Synthetic Route of Compound 4:

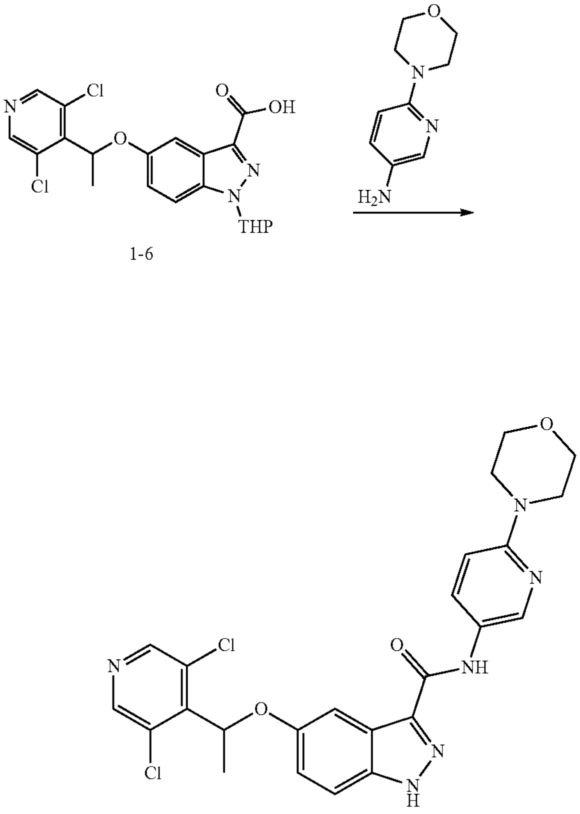

1-6

4

Synthesis Method:

Synthesis of compound 4: 5-(1-(3,5-dichloropyridin-4-yl)ethoxy)-N-(6-morpholinopyridin-3-yl)-1H-indazole-3-carboxamide 5-(1-(3,5-dichloropyridin-4-yl)ethoxy)-1-(tetrahydro-2H-pyran-2-yl)-1H-indazole-3-carboxylic acid (20.0 mg, 0.05 mmol) and 6-morpholinopyridin-3-amine (10.8 mg, 0.06 mmol) were dissolved in 5 ml DMF, then HATU (20.9 mg, 0.06 mmol) and DIPEA (17.8 mg, 0.14 mmol) were added to the solution and it was allowed to react for 3 h at room temperature. To the reaction solution, water was added, and the mixture was extracted with ethyl acetate twice. The resulting organic phases were combined, washed with saturated salt water, dried over anhydrous sodium sulfate, and concentrated, and the resulting solid was dissolved in 4 ml of methanol, to which 2 ml of concentrated hydrochloric acid was added, it was allowed to react at 50° C. for 1 h, and the reaction solution was concentrated. The concentrate was dissolved in 5 ml of methanol, neutralized with 0.5 ml of ammonia, concentrated, and purified by a preparative plate to afford 6.4 mg of the final product with a total yield of 19.6% in two steps.

$^1$H NMR (400 MHz, DMSO-$d_6$) δ 13.68 (s, 1H), 10.18 (s, 1H), 8.60 (s, 2H), 8.56 (d, J=4.0 Hz, 1H), 8.01 (dd, J=4.0 Hz, J=8.0 Hz, 1H), 7.58 (d, J=8.0 Hz, 1H), 7.50 (d, J=4.0 Hz, 1H), 7.16 (dd, J=4.0 Hz, J=8.0 Hz, 1H), 6.90 (d, J=12.0 Hz, 1H), 6.07 (q, J=6.6 Hz, 1H), 3.73-3.71 (m, 4H), 3.42-3.39 (m, 4H), 1.75 (d, J=8.0 Hz, 3H).

Example 5: Synthesis of N-(1-(1-cyanopropan-2-yl)-1H-pyrazol-4-yl)-5-(1-(3,5-dichloropyridin-4-yl)ethoxy)-1H-indazole-3-carboxamide (5)

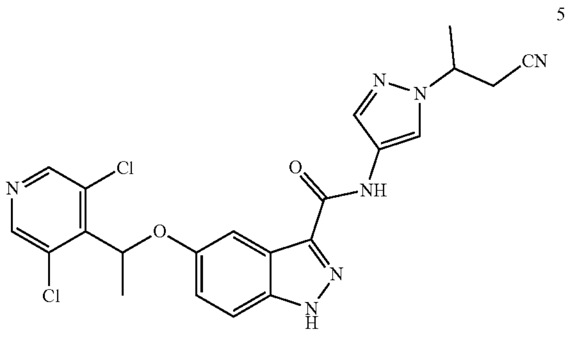 [SMILES: CC(Oc1ccc2[nH]nc(C(=O)Nc3cnn(C(C)CC#N)c3)c2c1)c1c(Cl)cncc1Cl]

Synthetic Route of Compound 5:

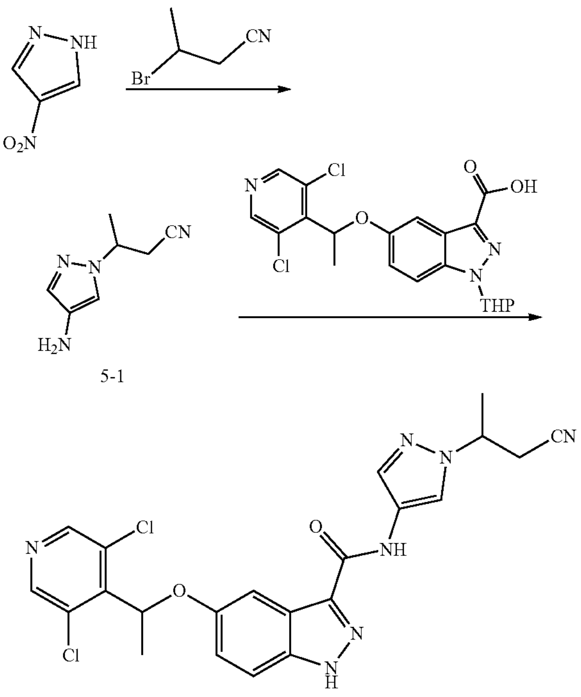

5-1

5

Synthesis Method:

Synthesis of Intermediate 5-1: 3-(4-amino-1H-pyrazol-1-yl)butanenitrile 4-nitro-1H-pyrazole (25 mg, 0.22 mmol) and 3-bromobutyronitrile (42.5 mg, 0.29 mmol) were dissolved in 5 ml of acetonitrile, potassium carbonate (92.1 mg, 0.66 mmol) was added to the solution and it was allowed to react at 80° C. for 3 hours. To the reaction solution, water was added, and the mixture was extracted with ethyl acetate twice. The resulting organic phases were combined, washed with saturated salt water, dried over anhydrous sodium sulfate, and concentrated. To the resulting residue, 3 ml of methanol and 2.5 mg of palladium carbon were added and the atmosphere was replaced by hydrogen gas. It was allowed to react at 40° C. for 1 h. After the reaction was completed, the reaction mixture was filtered, concentrated and purified on silica gel plate to afford 20 mg of Intermediate 5-1 with a yield of 60.24%.

$^1$H NMR (400 MHz, $CDCl_3$) δ 8.27 (s, 1H), 8.15 (s, 1H), 4.66-4.71 (m, 1H), 2.99-3.01 (m, 2H), 1.75 (d, J=8 Hz, 3H).

Synthesis of compound 5: N-(1-(1-cyanopropan-2-yl)-1H-pyrazol-4-yl)-5-(1-(3,5-dichloropyridin-4-yl)ethoxy)-1H-indazole-3-carboxamide Intermediate 5-1 (20 mg, 0.13 mmol) and Intermediate 1-6 (52.8 mg, 0.12 mmol) were dissolved in DMF (3 ml), then HATU (50.6 mg, 0.13 mmol) and DIPEA (31.2 mg, 0.24 mmol) were added, and it was allowed to react at room temperature for 3 h. Water was added to the reaction solution, the mixture was extracted twice with ethyl acetate, and the resulting organic phases were combined, washed with saturated salt water, dried over anhydrous sodium sulfate, and concentrated. The resulting residue was dissolved in 2 ml methanol and 1 ml concentrated hydrochloric acid, it was allowed to react at 50° C. for 2 h, and the reaction solution was concentrated. The concentrate was dissolved in 3 ml methanol, neutralized with 0.5 ml ammonia, concentrated, and purified by a preparative plate to afford 9 mg of final product with a yield of 15.5%.

$^1$H NMR (400 MHz, MeOD-$d_4$) δ 8.46 (s, 2H), 8.08 (s, 1H), 7.70 (s, 1H), 7.58 (d, J=4 Hz, 1H), 7.48 (d, J=8 Hz, 1H), 7.16 (d, J=8 Hz, 1H), 6.14-6.19 (m, 1H), 3.64 (m, 1H), 2.96-3.02 (m, 1H), 2.82-2.87 (m, 1H), 1.82 (d, J=4 Hz, 3H), 1.55 (d, J=8 Hz, 3H). LC-MS: $C_{22}H_{20}Cl_2N_7O_2$ $[M+H]^+$ m/z calculated as 484.1, detected as 484.1.

Example 6: Synthesis of 5-((R)-1-(3,5-dichloropyridin-4-yl)ethoxy)-N-(4-((3S,5R)-3,5-dimethylpiperazin-1-yl)phenyl)-1H-indazole-3-carboxamide (6)

6

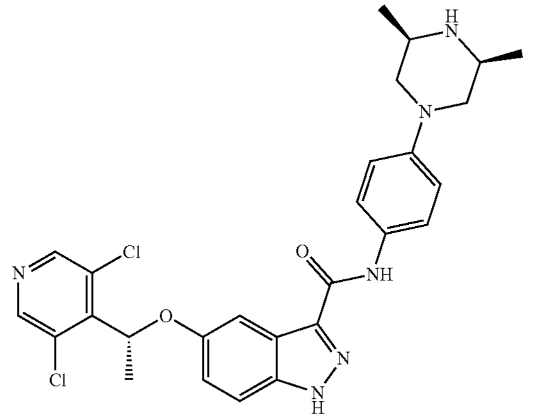

Synthetic Route of Compound 6:

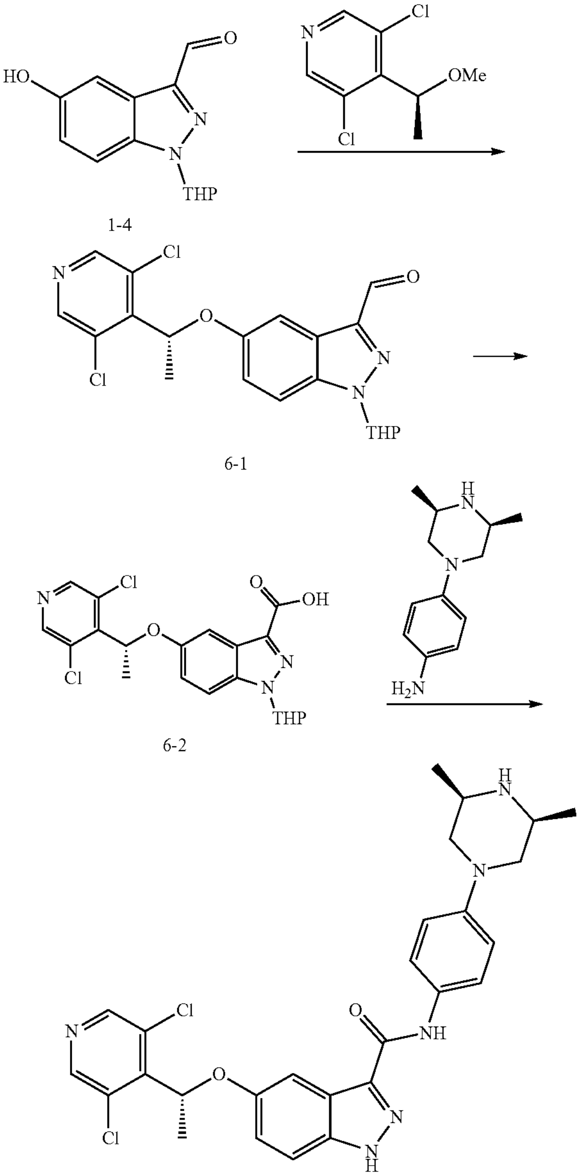

1-4

6-1

6-2

6

Synthesis Method:

Synthesis of Intermediate 6-1: 5-((R)-1-(3,5-dichloropyridin-4-yl)ethoxy)-1-(tetrahydro-2H-pyran-2-yl)-1H-indazole-3-carboxaldehyde (S)-1-(3,5-dichloropyridin-4-yl)ethan-1-ol (200.0 mg, 1.05 mmol) and triethylamine (317.6 mg, 3.14 mmol) were dissolved in 20 ml DCM and methanesulfonyl chloride (131.9 mg, 1.15 mmol) was added dropwise to the reaction solution at 0° C. The reaction was carried out at room temperature for 1 h. The reaction solution was quenched with water, and extracted twice with dichloromethane, and the resulting organic phases were combined, washed with saturated saline, dried over anhydrous sodium sulfate and concentrated. 1-4 (270.0 mg, 1.09 mmol) and the concentrate were dissolved in 20 ml DMF, to which cesium carbonate (684.2 mg, 2.10 mmol) was added, and it was allowed to react at 60° C. for 16 hours. Water was added to the reaction solution, and the mixture was extracted twice with ethyl acetate, and the resulting organic phases were combined, washed with saturated salt water, dried over anhydrous sodium sulfate, concentrated and purified by silica gel column to give 289.3 mg of Intermediate 6-1 with a yield of 65.5%.

$^1$H NMR (400 MHz, $CDCl_3$) δ 10.16 (s, 1H), 8.42 (s, 2H), 7.59-7.53 (m, 2H), 7.18-7.15 (m, 1H), 6.11 (q, J=6.7 Hz, 1H), 5.77-5.72 (m, 1H), 4.01-3.94 (m, 1H), 3.77-3.70 (m, 1H), 2.54-2.46 (m, 1H), 2.22-2.06 (m, 2H), 1.81 (d, J=6.7 Hz, 3H), 1.76-1.68 (m, 3H).

Synthesis of Intermediate 6-2: 5-((R)-1-(3,5-dichloropyridin-4-yl)ethoxy)-1-(tetrahydro-2H-pyran-2-yl)-1H-indazole-3-carboxylic acid 6-1 (289.3 mg, 0.69 mmol) was dissolved in 12 ml of acetonitrile and 4 ml of water, potassium permanganate (218.1 mg, 1.38 mmol) was added and the reaction was carried out for 16 h at room temperature. The reaction solution was filtered through diatomaceous earth, and the filtrate was adjusted to pH 3 with 3M hydrochloric acid, and extracted twice with dichloromethane, and the resulting organic phases were combined, washed with saturated salt water, dried over anhydrous sodium sulfate, concentrated, and purified by silica gel column to give 246.5 mg of Intermediate 6-2 with a yield of 81.8%.

$^1$H NMR (400 MHz, $CDCl_3$) δ 8.46 (s, 2H), 7.60-7.57 (m, 1H), 7.50 (s, 1H), 7.16 (d, J=9.1 Hz, 1H), 6.11 (q, J=6.7 Hz, 1H), 5.77-5.72 (m, 1H), 4.01-3.98 (m, 1H), 3.74-3.71 (m, 1H), 2.54-2.46 (m, 1H), 2.07-2.04 (m, 2H), 1.82 (d, J=6.7 Hz, 3H), 1.76-1.66 (m, 3H).

Synthesis of compound 6: 5-((R)-1-(3,5-dichloropyridin-4-yl)ethoxy)-N-(4-((3S,5R)-3,5-dimethylpiperazin-1-yl)phenyl)-1H-indazole-3-carboxamide 6-2 (40.0 mg, 0.09 mmol) and 4-((3S,5R)-3,5-dimethylpiperazin-1-yl)aniline (22.5 mg, 0.12 mmol) were dissolved in 10 ml DMF, then HATU (41.8 mg, 0.12 mmol) and DIPEA (35.6 mg, 0.26 mmol) were added to the solution and it was allowed to react for 3 h at room temperature. Water was added to the reaction solution and the mixture was extracted twice with ethyl acetate, and the resulting organic phases were combined, washed with saturated salt water, dried over anhydrous sodium sulfate and concentrated. The concentrate was dissolved in 6 ml of methanol, 3 ml of concentrated hydrochloric acid was added, it was allowed to react at 50° C. for 1 h, and the reaction solution was concentrated. The concentrate was dissolved in 5 ml of methanol, 0.5 ml of ammonia was added, and the resulting mixture was concentrated and purified by a preparative plate to give 37.2 mg of the final product with a yield of 76.3%.

$^1$H NMR (400 MHz, DMSO-$d_6$) δ 13.66 (s, 1H), 10.00 (s, 1H), 8.59 (s, 2H), 7.70 (d, J=8.6 Hz, 2H), 7.56 (d, J=9.0 Hz, 1H), 7.50 (s, 1H), 7.16-7.13 (m, 1H), 6.98 (d, J=8.7 Hz, 2H), 6.07 (q, J=6.6 Hz, 1H), 3.73 (d, J=12.7 Hz, 2H), 3.26-3.17 (m, 2H), 2.57-2.54 (m, 2H), 1.75 (d, J=6.6 Hz, 3H), 1.26-1.23 (m, 6H).

Example 7: Synthesis of (R)-5-(1-(3,5-dichloropyridin-4-yl)ethoxy)-N-(1-(2-hydroxyethyl)-1H-pyrazol-4-yl)-1H-indazole-3-carboxamide (7)

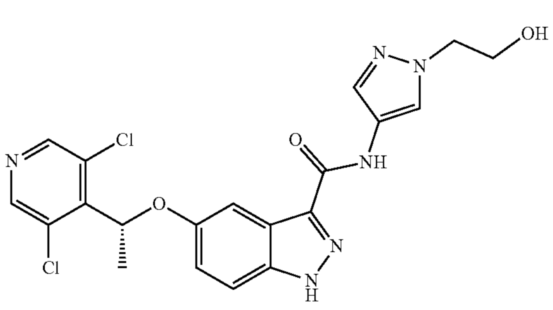

7

Synthetic Route of Compound 7:

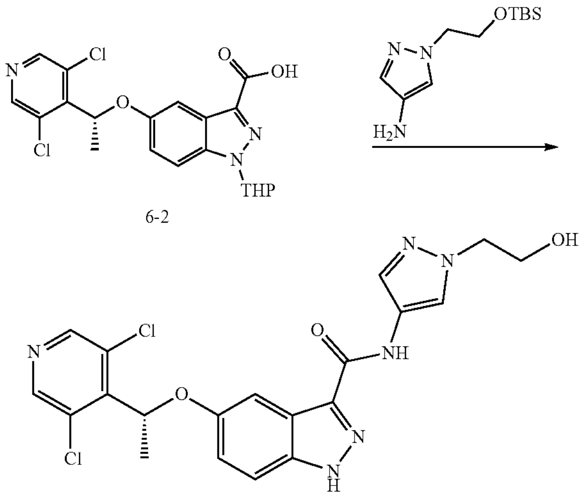

6-2

7

Synthesis Method:

Synthesis of compound 7: (R)-5-(1-(3,5-dichloropyridin-4-yl)ethoxy)-N-(1-(2-hydroxyethyl)-1H-pyrazol-4-yl)-1H-indazole-3-carboxamide 6-2 (40.0 mg, 0.09 mmol) and 1-(2-((tert-butyldimethylsilyl)oxy)ethyl)-1H-pyrazol-4-amine (24.4 mg, 0.10 mmol) were dissolved in 10 ml DMF, then HATU (41.8 mg, 0.12 mmol) and DIPEA (35.6 mg, 0.26 mmol) were added to the solution and it was allowed to react for 3 h at room temperature. Water was added to the reaction solution, and the mixture was extracted twice with ethyl acetate, and the resulting organic phases were combined, washed with saturated salt water, dried over anhydrous sodium sulfate and concentrated. The concentrate was dissolved in 6 ml of methanol, 3 ml of concentrated hydrochloric acid was added, it was allowed to react at 50° C. for 1 h, and the reaction solution was concentrated. The concentrate was dissolved in 5 ml of methanol, 0.5 ml of ammonia was added, and the resulting mixture was concentrated and purified by a preparative plate to afford 17.6 mg of the final product with a yield of 42.4%.

$^{1}H$ NMR (400 MHz, DMSO-$d_6$) δ 13.60 (s, 1H), 10.39 (s, 1H), 8.60 (s, 2H), 8.05 (s, 1H), 7.66 (s, 1H), 7.56-7.53 (s, 2H), 7.16-7.13 (m, 1H), 6.08 (q, J=6.6 Hz, 1H), 4.88 (t, J=5.3 Hz, 1H), 4.12 (t, J=5.7 Hz, 2H), 3.72 (q, J=5.6 Hz, 2H), 1.76 (d, J=6.6 Hz, 3H).

Example 8: Synthesis of 5-(1-(3,5-dichloropyridin-4-yl)ethoxy)-N-(6-((3S, 5R)-3,5-dimethylpiperazin-1-yl)pyridin-3-yl)-1H-indazole-3-carboxamide (8)

8

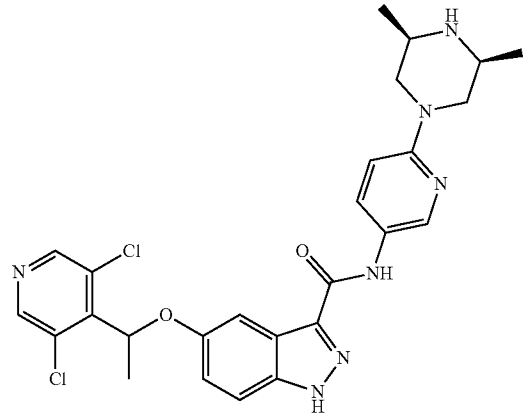

Synthetic Route of Compound 8:

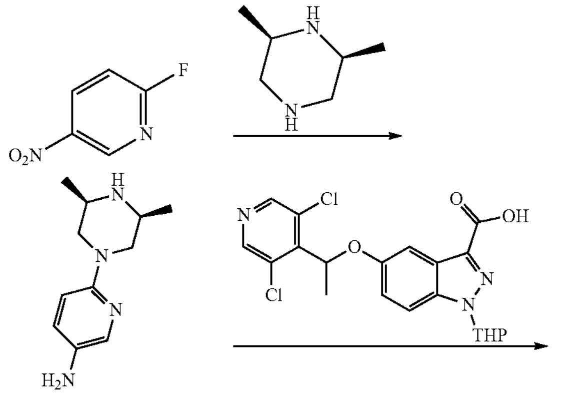

8-1

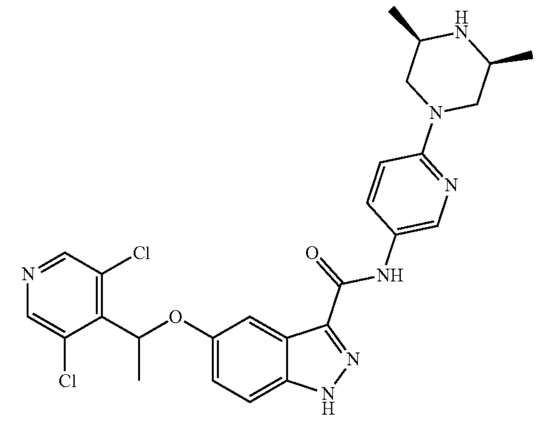

8

Synthesis Method:

Synthesis of Intermediate 8-1: 6-((3S, 5R)-3,5-dimethylpiperazin-1-yl) pyridine-3-amine 2-fluoro-5-nitropyridine (20 mg, 0.14 mmol) and (2S, 6R)-2,6-dimethyl piperazine (24.1 mg, 0.21 mmol) were dissolved in 3 ml DMSO, potassium carbonate (39.1 mg, 0.28 mmol) was added to the solution and it was allowed to react at 40° C. for 3 hours. Water was added to the reaction solution, and the mixture was extracted twice with ethyl acetate, and the resulting organic phases were combined, washed with saturated salt water, dried over anhydrous sodium sulfate and concentrated. To the resulting residue, 3 ml of methanol and 2.5 mg of 10% palladium carbon were added, and the atmosphere was replaced by hydrogen three times, and it was allowed to react at 40° C. for 1 h. After the reaction was completed, the reaction mixture was filtered, concentrated, and purified on silica gel plate to afford 20 mg of Intermediate 8-1 with a yield of 68.9%.

$^{1}H$ NMR (400 MHz, $CDCl_3$) δ 7.78 (s, 1H), 6.99 (d, J=8 Hz, 1H), 6.57 (d, J=8 Hz, 1H), 3.93-4.01 (m, 2H), 3.08-3.18 (m, 2H), 2.51-2.62 (m, 2H), 1.29-1.35 (m, 6H).

Synthesis of compound 8: 5-(1-(3,5-dichloropyridin-4-yl)ethoxy)-N-(6-((3S, 5R)-3, 5-dimethylpiperazin-1-yl)pyridin-3-yl)-1H-indazole-3-carboxamide Intermediate 8-1 (20 mg, 0.10 mmol) and Intermediate 1-6 (38.5 mg, 0.09 mmol) were dissolved in DMF (3 ml), then HATU (33.5 mg, 0.09 mmol) and DIPEA (22.74 mg, 0.18 mmol) were added and it was allowed to react at room temperature for 3 h. Water was added to the reaction solution, and the mixture was extracted twice with ethyl acetate, and the resulting organic phases were combined, washed with saturated salt water, dried over anhydrous sodium sulfate, concentrated and purified by silica gel column. The resulting product was dissolved in 2 ml of methanol and 1 ml of concentrated hydrochloric acid, it was allowed to react at 50° C. for 2 h, and the reaction solution was concentrated. The concentrate was dissolved in 3 ml of methanol, 0.5 ml of ammonia was added, and the resulting mixture was concentrated and purified by a preparative plate to afford 8 mg of the final product with a yield of 15.3%.

$^{1}H$ NMR (400 MHz, MeOD-$d_4$) δ 8.45 (s, 3H), 7.93 (d, J=8 Hz, 1H), 7.56 (s, 1H), 7.48 (d, J=12 Hz, 1H), 7.17 (d, J=8 Hz, 1H), 6.88 (d, J=8 Hz, 1H), 6.12-6.17 (m, 1H), 4.16 (d, J=12 Hz, 2H), 2.95-3.01 (m, 2H), 2.42-2.48 (m, 2H), 1.81 (d, J=4 Hz, 3H), 1.20 (d, J=4 Hz, 6H).

Example 9: Synthesis of 5-(1-(3,5-dichloropyridin-4-yl)ethoxy)-N-(4-(4-methylpiperazin-1-yl)phenyl)-1H-indazole-3-carboxamide (9)

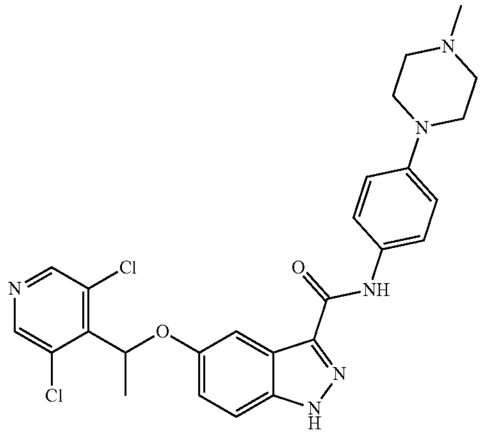

9

Synthetic Route of Compound 9:

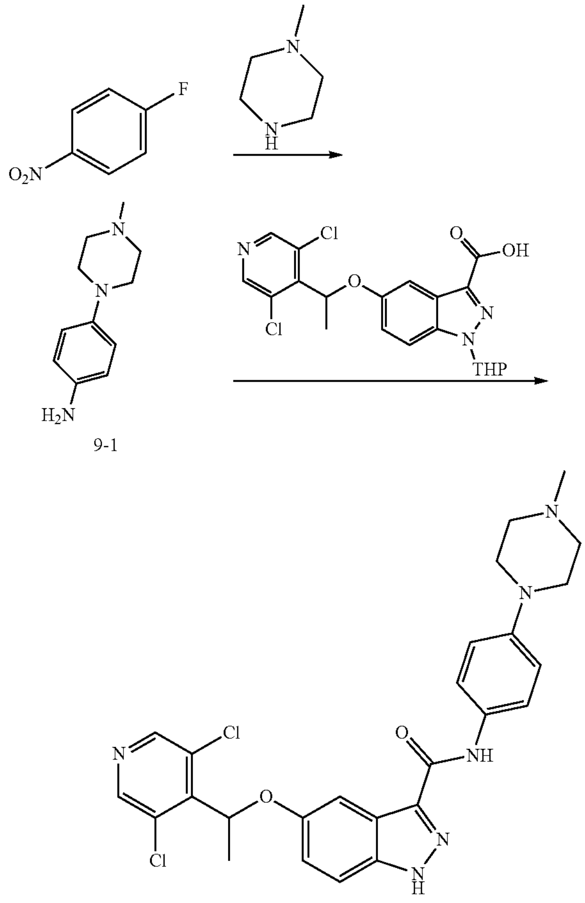

9-1

9

Synthesis Method:

Synthesis of Intermediate 9-1: 4-(4-methylpiperazin-1-yl)aniline 4-nitrofluorobenzene (25 mg, 0.18 mmol) and 1-methylpiperazine (26.6 mg, 0.27 mmol) were dissolved in 3 ml DMSO, potassium carbonate (49.3 mg, 0.35 mmol) was added to the solution and it was allowed to react at 40° C. for 3 hours. Water was added to the reaction solution, and the mixture was extracted twice with ethyl acetate, and the resulting organic phases were combined, washed with saturated salt water, dried over anhydrous sodium sulfate and concentrated. To the resulting residue, 3 ml of methanol and 2.5 mg of palladium carbon were added, the atmosphere was replaced by hydrogen gas and the reaction was carried out at 40° C. for 1 h. After the reaction was completed, the reaction mixture was filtered, concentrated and purified on silica gel plate to afford 20 mg of Intermediate 9-1 with a yield of 73.8%.

$^1$H NMR (400 MHz, $CDCl_3$) δ 6.82 (d, J=8 Hz, 2H), 6.65 (d, J=8 Hz, 2H), 3.08-3.10 (m, 4H), 2.60-2.63 (m, 4H), 2.37 (s, 3H).

Synthesis of compound 9: 5-(1-(3,5-dichloropyridin-4-yl)ethoxy)-N-(4-(4-methylpiperazin-1-yl)phenyl)-1H-indazole-3-carboxamide Intermediate 9-1 (20 mg, 0.10 mmol) and Intermediate 1-6 (41.5 mg, 0.09 mmol) were dissolved in DMF (3 ml), HATU (36.1 mg, 0.09 mmol) and DIPEA (24.5 mg, 0.19 mmol) were added, and it was allowed to react at room temperature for 3 h. Water was added to the reaction solution, and the mixture was extracted twice with ethyl acetate, and the resulting organic phases were combined, washed with saturated salt water, dried over anhydrous sodium sulfate, concentrated and purified by silica gel column. The resulting product was dissolved in 2 ml of methanol and 1 ml of concentrated hydrochloric acid, it was allowed to react at 50° C. for 2 h, and the reaction solution was concentrated. The concentrate was dissolved in 3 ml of methanol, 0.5 ml of ammonia was added, and the resulting mixture was concentrated and purified by a preparative plate to afford 10 mg of the final product with a yield of 18.2%.

$^1$H NMR (400 MHz, DMSO-$d_6$) δ 13.60 (s, 1H), 9.94 (s, 1H), 8.59 (s, 2H), 7.66 (d, J=8 Hz, 2H), 7.55 (d, J=8 Hz, 1H), 7.50 (d, J=4 Hz, 1H), 7.14 (d, J=8 Hz, 1H), 6.92 (d, J=8 Hz, 2H), 6.04-6.09 (m, 1H), 3.10-3.13 (m, 4H), 2.49-2.52 (m, 4H), 2.26 (s, 3H), 1.75 (d, J=4 Hz, 3H).

Example 10: Synthesis of 5-(1-(3,5-dichloropyridin-4-yl)ethoxy)-N-(4-(4-ethylpiperazin-1-yl)phenyl)-1H-indazole-3-carboxamide (10)

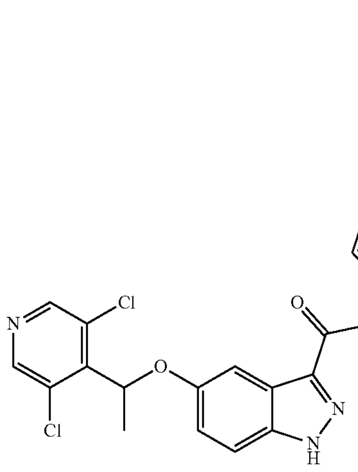

10

Synthetic Route of Compound 10:

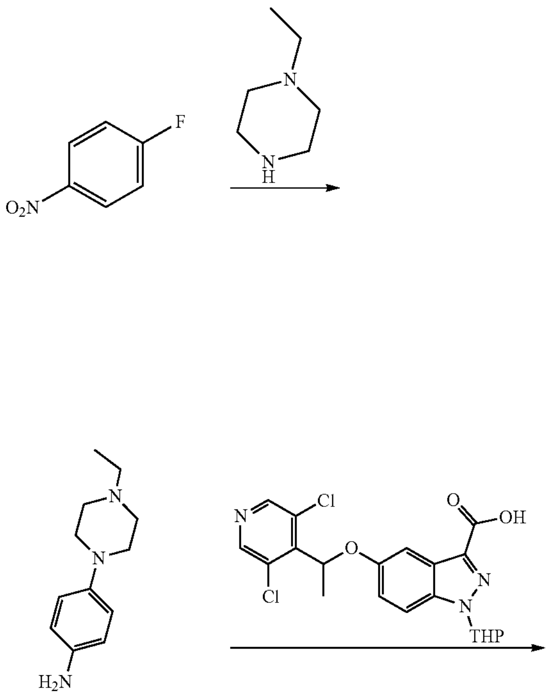

10-1

-continued

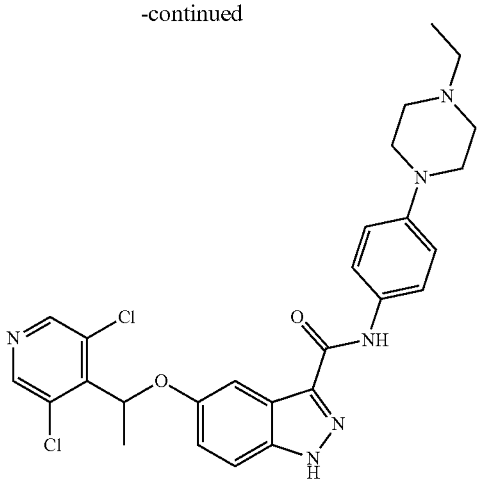

10

Synthesis Method

Synthesis of intermediate 10-1: 4-(4-ethylpiperazin-1-yl)aniline 4-nitrofluorobenzene (25 mg, 0.18 mmol) and 1-ethylpiperazine (30.4 mg, 0.27 mmol) were dissolved in 3 ml DMSO, potassium carbonate (49.3 mg, 0.35 mmol) was added to the solution and it was allowed to react at 40° C. for 3 hours. Water was added to the reaction solution, and the mixture was extracted twice with ethyl acetate, and the resulting organic phases were combined, washed with saturated salt water, dried over anhydrous sodium sulfate and concentrated. To the resulting residue, 3 ml of methanol and 2.5 mg of palladium carbon were added, the atmosphere was replaced by hydrogen gas three times and the reaction was carried out at 40° C. for 1 h. After the reaction was completed, the reaction mixture was filtered, concentrated and purified on silica gel plate to afford 20 mg of intermediate 10-1 with a yield of 68.7%.

$^1$H NMR (400 MHz, $CDCl_3$) δ 6.82 (d, J=8 Hz, 2H), 6.65 (d, J=8 Hz, 2H), 3.09-3.12 (m, 4H), 2.64-2.66 (m, 4H), 2.48-2.54 (m, 2H), 1.15 (t, J=8 Hz, 3H).

Synthesis of compound 10: 5-(1-(3, 5-dichloropyridin-4-yl)ethoxy)-N-(4-(4-ethylpiperazin-1-yl)phenyl)-1H-indazole-3-carboxamide Intermediate 10-1 (20 mg, 0.10 mmol) and Intermediate 1-6 (38.6 mg, 0.09 mmol) were dissolved in DMF (3 ml), HATU (33.7 mg, 0.09 mmol) and DIPEA (22.9 mg, 0.18 mmol) were added, and it was allowed to react at room temperature for 3 h. Water was added to the reaction solution, and the mixture was extracted twice with ethyl acetate, and the resulting organic phases were combined, washed with saturated salt water, dried over anhydrous sodium sulfate, concentrated and purified by silica gel column. The resulting product was dissolved in 2 ml of methanol and 1 ml of concentrated hydrochloric acid, it was allowed to react at 50° C. for 2 h, and the reaction solution was concentrated. The concentrate was dissolved in 3 ml of methanol, 0.5 ml of ammonia was added, and the resulting mixture was concentrated and purified by a preparative plate to afford 12 mg of the final product with a yield of 22.8%.

$^1$H NMR (400 MHz, DMSO-$d_6$) δ 13.60 (s, 1H), 9.95 (s, 1H), 8.59 (s, 2H), 7.66 (d, J=8 Hz, 2H), 7.55 (d, J=8 Hz, 1H), 7.50 (d, J=4 Hz, 1H), 7.14 (d, J=8 Hz, 1H), 6.92 (d, J=8 Hz, 2H), 6.04-6.09 (m, 1H), 3.09-3.14 (m, 4H), 2.51-2.55 (m, 4H), 2.41-2.44 (m, 2H), 1.75 (d, J=4 Hz, 3H), 1.06 (t, J=4 Hz, 3H).

Example 11: Synthesis of N-(1-(2-cyanoethyl)-1H-pyrazol-4-yl)-5-(1-(3,5-dichloropyridin-4-yl) ethoxy)-1H-indazole-3-carboxamide (11)

11

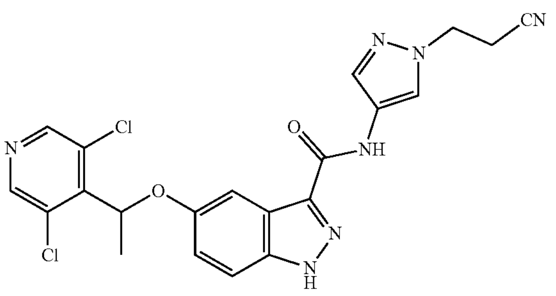

Synthetic Route of Compound 11:

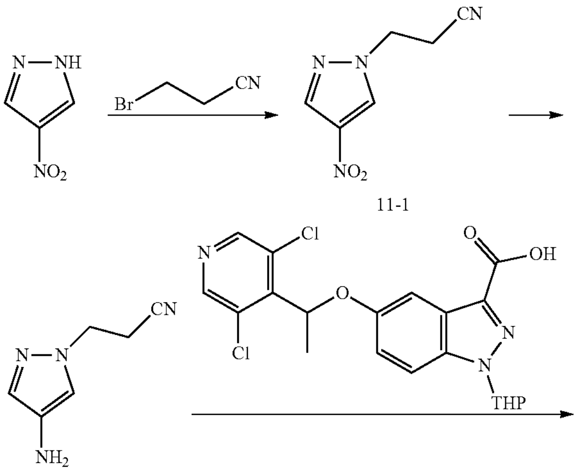

11-1

11-2

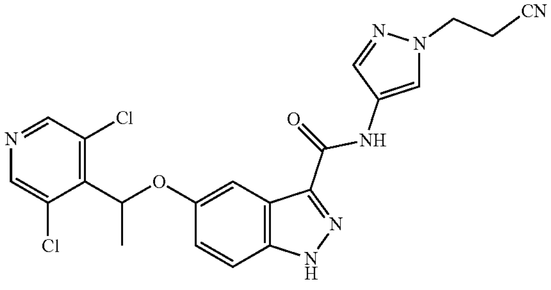

11

Synthesis Method:

Synthesis of intermediate 11-1: 3-(4-nitro-1H-pyrazol-1-yl)propanenitrile

4-Nitro-1H-pyrazole (200 mg, 1.77 mmol) was dissolved in 25 ml of acetonitrile, potassium carbonate (733 mg, 5.31 mmol) and bromopropionitrile (284 mg, 2.12 mmol) were added to the reaction solution, and the reaction was heated to 80° C. after the addition was completed. After the reaction was completed, 50 ml of water was added to the system, the mixture was extracted with EA, and partitioned, and the organic phase was washed with saturated salt water, dried over anhydrous sodium sulfate, and concentrated by column chromatography to afford 270 mg of Intermediate 11-1 with a yield of 91.9%.

$^1$H NMR (400 MHz, $CDCl_3$) δ 8.28 (s, 1H), 8.15 (s, 1H), 4.44 (t, J=6.5 Hz, 2H), 3.04 (t, J=6.5 Hz, 2H).

Synthesis of Intermediate 11-2: 3-(4-amino-1H-pyrazol-1-yl) propanenitrile

Intermediate 11-1 (200 mg, 1.20 mmol) was dissolved in 10 ml of methanol and 10% Pd/C (20 mg) was added to the system, which was replaced with hydrogen gas three times and then it was allowed to react at room temperature. After the reaction was completed, the system was filtered and concentrated to give 156 mg of intermediate 11-2 with a yield of 95.4%.

Synthesis of compound 11: N-(1-(2-cyanoethyl)-1H-pyrazol-4-yl)-5-(1-(3,5-dichloropyridin-4-yl) ethoxy)-1H-indazole-3-carboxamide Intermediate 5-(1-(3,5-dichloropyridin-4-yl)ethoxy)-1-(tetrahydro-2H-pyran-2-yl)-1H-indazole-3-carboxylic acid (30.0 mg, 0.069 mmol) was dissolved in 4 ml DMF, HATU (28.8 mg, 0.076 mmol) and DIPEA (17.8 mg, 0.138 mmol) were added to the system and the mixture was stirred for one hour at room temperature. Then Intermediate 15-2 (9.37 mg, 0.069 mmol) was added to the system and it was allowed to react at room temperature after the addition was completed. After the reaction was completed, the system was quenched with water, and extracted twice with ethyl acetate, and the resulting organic phases were combined, washed with saturated salt water, dried over anhydrous sodium sulfate, and concentrated. The resulting residue was dissolved in 4 ml of methanol, then 2 ml of concentrated hydrochloric acid was added, and it was allowed to react at 50° C. After the reaction was completed, the reaction solution was evaporated under reduced pressure, the residue was dissolved in 2 ml of methanol, and neutralized by adding 0.5 ml of ammonia. After the neutralization, it was concentrated and purified by column chromatography to give 5.3 mg of compound 11 with a yield of 18.4%.

$^1$H NMR (400 MHz, $CDCl_3$) δ 10.26 (s, 1H), 8.63 (s, 1H), 8.42 (s, 2H), 8.09 (s, 1H), 7.77 (d, J=2.3 Hz, 1H), 7.57 (s, 1H), 7.39 (d, J=9.0 Hz, 1H), 7.17 (dd, J=2.3, 9.0 Hz, 1H), 6.14 (q, J=6.7 Hz, 1H), 4.43 (t, J=6.8 Hz, 2H), 2.94 (t, J=6.8 Hz, 2H), 1.76 (d, J=6.7 Hz, 3H). LC-MS: $C_{21}H_{18}Cl_2N_7O_2$ $[M+H]^+$ m/z calculated as 470.1, detected as 470.1.

Example 12: Synthesis of 5-(1-(3,5-dichloropyridin-4-yl)ethoxy)-N-(1-(3-hydroxycyclobutyl)-1H-pyrazol-4-yl)-1H-indazole-3-carboxamide (12)

12

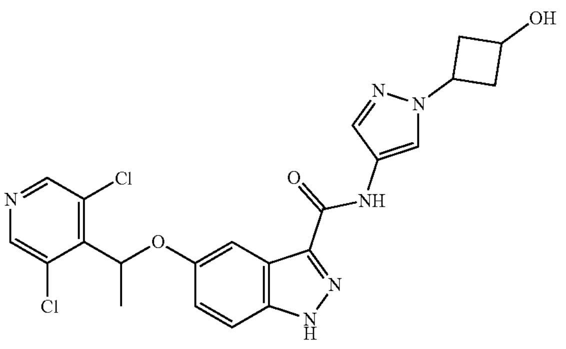

Synthetic Route of Compound 12:

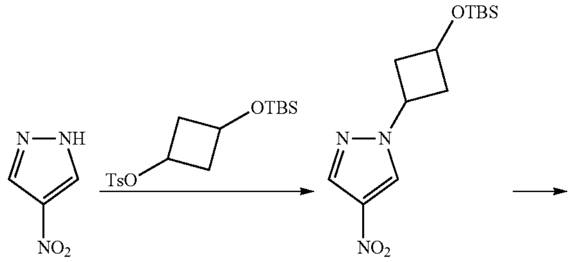

12-1

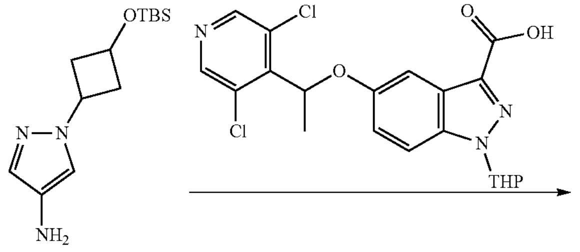

12-2

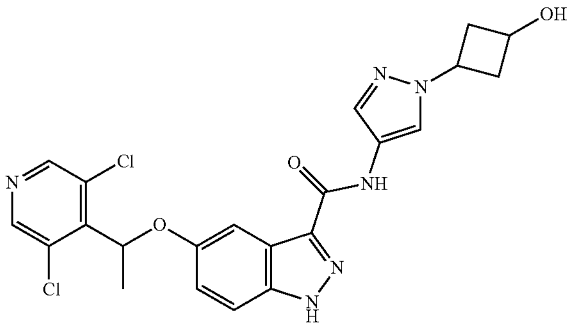

12

Synthesis Method:

Synthesis of intermediate 12-1: 1-(3-((tert-butyldimethylsilyl)oxy)cyclobutyl)-4-nitro-1H-pyrazole 4-Nitro-1H-pyrazole (149 mg, 1.32 mmol) was dissolved in 25 ml of acetonitrile, potassium phosphate (839 mg, 3.95 mmol) and cyclobutyl 3-((tert-butyldimethylsilyl)oxy)4-methylbenzenesulfonate (470 mg, 1.32 mmol) were added to the reaction solution and it was allowed to react at 80° C. After the reaction was completed, 50 ml of water was added to the system, the mixture was extracted with EA, and partitioned, and the organic phase was washed with saturated salt water, dried over anhydrous sodium sulfate and concentrated by column chromatography to give 223 mg of Intermediate 12-1 with a yield of 56.8%.

$^1$H NMR (400 MHz, $CDCl_3$) δ 8.07 (s, 1H), 8.04 (s, 1H), 4.86-4.79 (m, 1H), 4.64-4.58 (m, 1H), 2.75-2.69 (m, 2H), 2.52-2.45 (m, 2H), 0.84 (s, 9H), 0.02 (s, 6H).

Synthesis of Intermediate 12-2: 1-(3-((tert-butyldimethylsilyl)oxy) cyclobutyl)-1H-pyrazol-4-amine Intermediate 12-1 (50 mg, 0.168 mmol) was dissolved in 5 ml of methanol, 10% Pd/C (5 mg) was added to the system, the atmosphere was replaced with hydrogen three times and then the reaction was carried out at room temperature. After the reaction was completed, the reaction system was filtered and concentrated to give 43 mg of intermediate 12-2 with a yield of 95.6%.

Synthesis of compound 12: 5-(1-(3,5-dichloropyridin-4-yl)ethoxy)-N-(1-(3-hydroxycyclobutyl)-1H-pyrazol-4-yl)-1H-indazole-3-carboxamide Intermediate 5-(1-(3,5-dichloropyridin-4-yl)ethoxy)-1-(tetrahydro-2H-pyran-2-yl)-1H-indazole-3-carboxylic acid (36.0 mg, 0.082 mmol) was dissolved in 4 ml DMF, HATU (34.4 mg, 0.091 mmol) and DIPEA (21.2 mg, 0.165 mmol) were added to the system and the mixture was stirred for one hour at room temperature. Then Intermediate 12-2 (22.0 mg, 0.082 mmol) was added to the system and it was allowed to react at room temperature after the addition was completed. After the reaction was completed, the system was quenched with water, and extracted twice with ethyl acetate, and the resulting organic phases were combined, washed with saturated salt water, dried over anhydrous sodium sulfate, and concentrated. The resulting residue was dissolved in 4 ml of methanol, then 2 ml of concentrated hydrochloric acid was added, and it was allowed to react at 50° C. After the reaction was completed, the reaction solution was evaporated under reduced pressure, the residue was dissolved in 2 ml of methanol, and neutralized by adding 0.5 ml of ammonia. After the neutralization, it was concentrated and purified by column chromatography to give 16.0 mg of compound 12 with a yield of 42.3%.

$^1$H NMR (400 MHz, MeOD-$d_4$) δ 8.46 (s, 2H), 8.09 (s, 1H), 7.73 (s, 1H), 7.58 (d, J=2.2 Hz, 1H), 7.48 (d, J=9.1 Hz, 1H), 7.16 (dd, J=2.3, 9.0 Hz, 1H), 6.16 (q, J=6.7 Hz, 1H), 5.02-4.94 (m, 1H), 4.62-4.56 (m, 1H), 2.82-2.75 (m, 2H), 2.54-2.47 (m, 2H), 1.81 (d, J=6.7 Hz, 3H).

Example 13: Synthesis of 5-(1-(3,5-dichloropyridin-4-yl)ethoxy)-N-(4-(4-hydroxypiperidin-1-yl)phenyl)-1H-indazole-3-carboxamide (13)

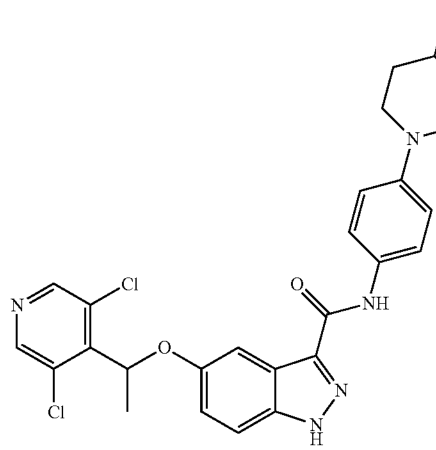

13

Synthetic Route of Compound 13:

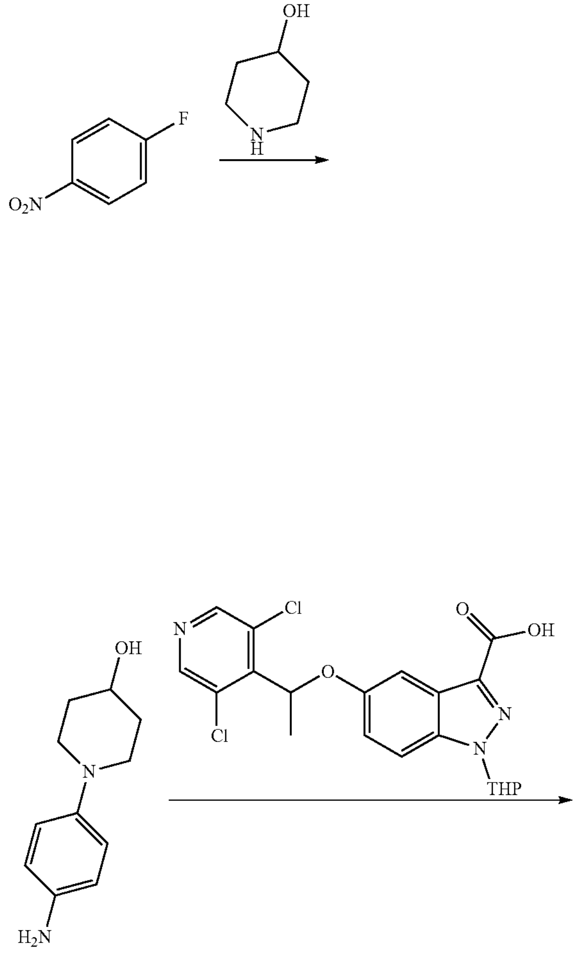

13-1

-continued

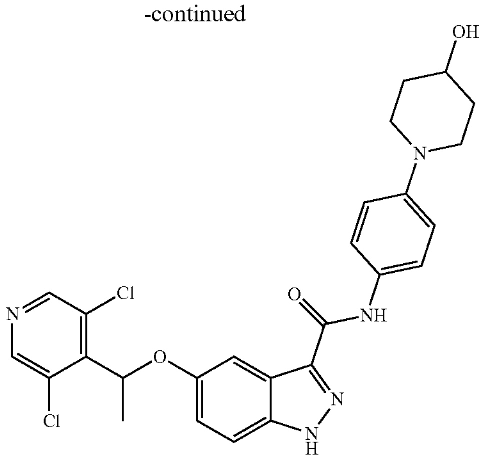

13

Synthesis Method:

Synthesis of Intermediate 13-1: 1-(4-aminophenyl)piperidin-4-ol 4-nitrofluorobenzene (25 mg, 0.18 mmol) and piperidin-4-ol (26.9 mg, 0.27 mmol) were dissolved in 3 ml DMSO, potassium carbonate (49.3 mg, 0.35 mmol) was added to the solution and it was allowed to react at 40° C. for 3 hours. Water was added to the reaction solution, and the mixture was extracted twice with ethyl acetate, and the resulting organic phases were combined, washed with saturated salt water, dried over anhydrous sodium sulfate and concentrated. To the resulting residue, 3 ml of methanol and 2.5 mg of palladium carbon were added, the atmosphere was replaced by hydrogen gas three times and the reaction was carried out at 40° C. for 1 h. After the reaction was completed, the reaction mixture was filtered, concentrated and purified on silica gel plate to afford 20 mg of intermediate 13-1 with a yield of 73.4%.

$^1$H NMR (400 MHz, $CDCl_3$) δ 6.85 (d, J=8 Hz, 2H), 6.64 (d, J=8 Hz, 2H), 3.79-3.83 (m, 1H), 3.33-3.39 (m, 2H), 2.77-2.83 (m, 2H), 2.01-2.05 (m, 2H), 1.68-1.77 (m, 2H).

Synthesis of compound 13: 5-(1-(3,5-dichloropyridin-4-yl)ethoxy)-N-(4-(4-hydroxypiperidin-1-yl)phenyl)-1H-indazole-3-carboxamide Intermediate 13-1 (20 mg, 0.10 mmol) and Intermediate 1-=(41.3 mg, 0.09 mmol) were dissolved in DMF (3 ml), HATU (35.9 mg, 0.09 mmol) and DIPEA (24.4 mg, 0.18 mmol) were added, and it was allowed to react at room temperature for 3 h. Water was added to the reaction solution, and the mixture was extracted twice with ethyl acetate, and the resulting organic phases were combined, washed with saturated salt water, dried over anhydrous sodium sulfate, concentrated and purified by silica gel column. The resulting product was dissolved in 2 ml of methanol and 1 ml of concentrated hydrochloric acid, it was allowed to react at 50° C. for 2 h, and the reaction solution was concentrated. The concentrate was dissolved in 3 ml of methanol, 0.5 ml of ammonia was added, and the resulting mixture was concentrated and purified by a preparative plate to afford 8 mg of the final product with a yield of 14.60%.

$^1$H NMR (400 MHz, DMSO-$d_6$) δ 13.58 (s, 1H), 9.92 (s, 1H), 8.59 (s, 2H), 7.63 (d, J=12 Hz, 2H), 7.55 (d, J=8 Hz, 1H), 7.50 (d, J=4 Hz, 1H), 7.14 (d, J=8 Hz, 1H), 6.90 (d,

J=12 Hz, 2H), 6.04-6.09 (m, 1H), 4.63-4.65 (m, 1H), 3.61-3.63 (m, 1H), 3.47-3.50 (m, 2H), 2.77-2.83 (m, 2H), 1.81-1.84 (m, 2H), 1.75 (d, J=4 Hz, 3H), 1.48-1.52 (m, 2H).

Example 14: Synthesis of 5-(1-(3,5-dichloropyridin-4-yl)ethoxy)-N-(1-(1-methylpiperidin-4-yl)-1H-pyrazol-4-yl)-1H-indazole-3-carboxamide (14)

14

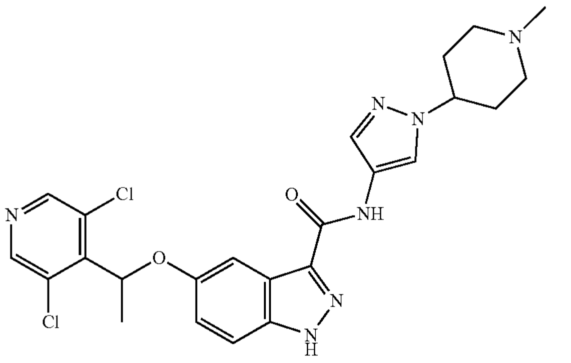

Synthetic Route of Compound 14

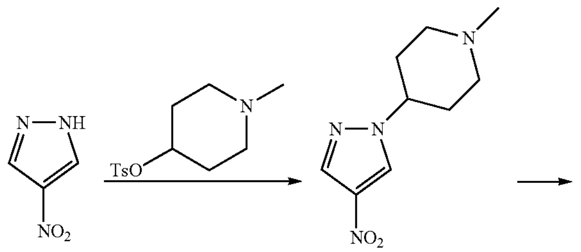

14-1

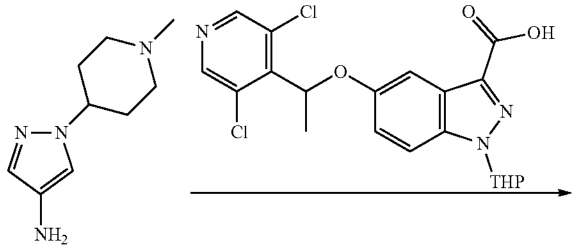

14-2

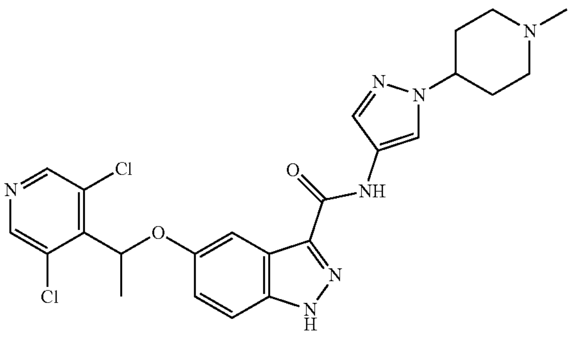

14

Synthesis Method:

Synthesis of Intermediate 14-1: 1-methyl-4-(4-nitro-1H-pyrazol-1-yl)piperidine 4-nitro-1H-pyrazole (100 mg, 0.884 mmol) was dissolved in 20 ml of acetonitrile, and potassium phosphate (563 mg, 2.65 mmol) and 1-methylpiperidin-4-yl-4-methylbenzene-sulfonate (238 mg, 0.884 mmol) were added to the reaction solution, and it was allowed to react at 80° C. After the reaction was completed, 50 ml of water was added to the system, the mixture was extracted with EA, and partitioned, and the organic phase was washed with saturated salt water, dried over anhydrous sodium sulfate and concentrated by column chromatography to give 112 mg of Intermediate 14-1 with a yield of 60.1%.

$^1$H NMR (400 MHz, $CDCl_3$) δ 8.17 (s, 1H), 8.08 (s, 1H), 4.18-4.10 (m, 1H), 3.02-2.98 (m, 2H), 2.51 (s, 3H), 2.22-2.13 (m, 4H), 2.09-1.99 (m, 2H).

Synthesis of Intermediate 14-2: 1-(1-methylpiperidin-4-yl)-1H-pyrazol-4-amine Intermediate 14-1 (50.0 mg, 0.238 mmol) was dissolved in 5 ml of methanol and 10% Pd/C (5 mg) was added to the system, the atmosphere was replaced with hydrogen three times and then the reaction was carried out at room temperature. After the reaction was completed, the system was filtered and concentrated to give 37.0 mg of intermediate 14-2 with a yield of 86.3%.

Synthesis of compound 14: 5-(1-(3,5-dichloropyridin-4-yl)ethoxy)-N-(1-(1-methylpiperidin-4-yl)-1H-pyrazol-4-yl)-1H-indazole-3-carboxamide Intermediate 5-(1-(3,5-dichloropyridin-4-yl)ethoxy)-1-(tetrahydro-2H-pyran-2-yl)-1H-indazole-3-carboxylic acid (30.0 mg, 0.069 mmol) was dissolved in 4 ml DMF, HATU (28.7 mg, 0.076 mmol) and DIPEA (17.8 mg, 0.138 mmol) were added to the system and the mixture was stirred for one hour at room temperature. Then Intermediate 14-2 (12.4 mg, 0.069 mmol) was added to the system and it was allowed to react at room temperature after the addition was completed. After the reaction was completed, the system was quenched with water, and extracted twice with ethyl acetate, and the resulting organic phases were combined, washed with saturated salt water, dried over anhydrous sodium sulfate, and concentrated. The resulting residue was dissolved in 4 ml of methanol, then 2 ml of concentrated hydrochloric acid was added, and it was allowed to react at 50° C. After the reaction was completed, the reaction solution was evaporated under reduced pressure, the residue was dissolved in 2 ml of methanol, and neutralized by adding 0.5 ml of ammonia. After the neutralization, it was concentrated and purified by column chromatography to give 14.0 mg of compound 14 with a yield of 39.6%.

$^1$H NMR (400 MHz, MeOD-$d_4$) δ 8.45 (s, 2H), 8.10 (s, 1H), 7.70 (s, 1H), 7.58 (d, J=2.3 Hz, 1H), 7.48 (d, J=9.1 Hz, 1H), 7.16 (dd, J=2.4, 9.1 Hz, 1H), 6.16 (q, J=6.7 Hz, 1H), 4.23-4.03 (m, 1H), 3.08-2.99 (m, 2H), 2.37 (s, 3H), 2.33-2.26 (m, 2H), 2.19-2.05 (m, 4H), 1.81 (d, J=6.7 Hz, 3H).

Example 15: Synthesis of 5-(1-(3,5-dichloropyridin-4-yl)ethoxy)-N-(1-(2-(1-hydroxycyclopropyl)ethyl)-1H-pyrazol-4-yl)-1H-indazole-3-methylamide (15)

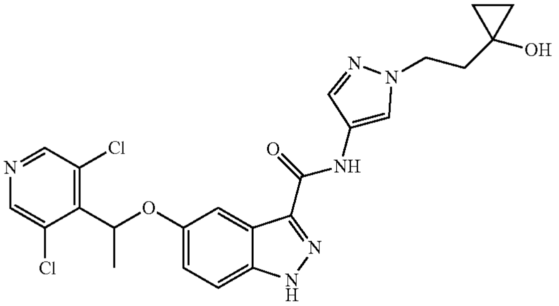

Synthetic Route of Compound 15:

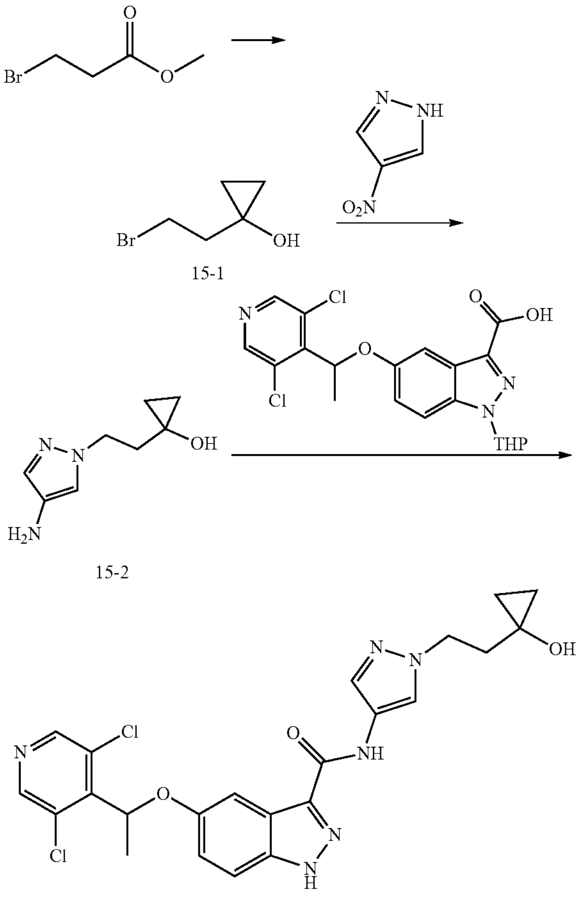

15-1

15-2

15

Synthesis Method:

Synthesis of Intermediate 15-1: 1-(2-bromoethyl)cyclopropan-1-ol

Methyl 3-bromopropionate (1 g, 5.99 mmol) and tetraisopropyl titanate (170.2 mg, 0.60 mmol) were dissolved in 30 ml THE (dry). The atmosphere was replaced by nitrogen, and the system was cooled down to 0° C. Ethylmagnesium bromide (13.2 ml, 1 mol/L) was added dropwise to the solution, and it was allowed to react for 2 h at room temperature. To the reaction solution, saturated ammonium chloride solution was added, and the mixture was extracted twice with ethyl acetate, and the resulting organic phases were combined, washed with saturated salt water, dried over anhydrous sodium sulfate, and concentrated and purified by column chromatography to afford 230 mg of Intermediate 15-1 with a yield of 23.3%.

$^1$H NMR (400 MHz, $CDCl_3$) δ 3.62 (t, J=6 Hz, 2H), 2.13 (t, J=8 Hz, 2H), 0.81-0.84 (m, 2H), 0.54-0.57 (m, 2H).

Synthesis of Intermediate 15-2: 1-(2-(4-amino-1H-pyrazol-1-yl)ethyl) cyclopropan-1-ol 4-nitro-1H-pyrazole (100 mg, 0.88 mmol) was dissolved in 15 ml acetonitrile, cesium carbonate (864.9 mg, 2.65 mmol) and Intermediate 15-1 (230 mg, 1.39 mmol) were added to the reaction solution, and it was allowed to react at 60° C. 3 hours later, 30 ml of water was added to the system, the mixture was extracted with EA, and partitioned, and the organic phase was washed with saturated salt water, dried over anhydrous sodium sulfate and concentrated by column chromatography to give 100 mg of product. The product was dissolved in 5 ml of methanol, 10 mg of palladium carbon was added, the atmosphere was replaced by hydrogen, and the reaction was carried out for 1 h at room temperature. After the reaction was completed, the reaction mixture was filtered, concentrated and purified by column chromatography to afford 60 mg of intermediate 15-2 with a yield of 40.6%.

$^1$H NMR (400 MHz, $CDCl_3$) δ 7.16 (s, 1H), 7.03 (s, 1H), 4.26 (t, J=6 Hz, 2H), 1.95 (t, J=6 Hz, 2H), 0.67-0.70 (m, 2H), 0.27-0.30 (m, 2H).

Synthesis of compound 15: 5-(1-(3,5-dichloropyridin-4-yl)ethoxy)-N-(1-(2-(1-hydroxycyclopropyl) ethyl)-1H-pyrazol-4-yl)-1H-indazole-3-carboxamide Intermediate 1-6 (50 mg, 0.11 mmol) was dissolved in 2 ml of methanol and 1 ml of concentrated hydrochloric acid, and it was allowed to react at 50° C. for 3 h. The reaction solution was concentrated, 3 ml of methanol and 0.5 ml of ammonia were added, and the resulting mixture was concentrated and purified by column chromatography. The resulting product and Intermediate 15-2 (14.2 mg, 0.08 mmol) were dissolved in DMF (3 ml), HATU (38.8 mg, 0.10 mmol) and DIPEA (22.0 mg, 0.17 mmol) were added, and it was allowed to react at room temperature for 2 h. Water was added to the reaction solution, and the mixture was extracted twice with ethyl acetate, and the resulting organic phases were combined, washed with saturated salt water, dried over anhydrous sodium sulfate, concentrated and purified by column chromatography to afford 2.8 mg of the final product with a yield of 7%.

$^1$H NMR (400 MHz, DMSO-$d_6$) δ 13.61 (s, 1H), 10.39 (s, 1H), 8.60 (s, 2H), 8.05 (s, 1H), 7.64 (s, 1H), 7.54-7.56 (m, 2H), 7.15 (d, J=8 Hz, 1H), 6.06-6.11 (m, 1H), 4.25 (t, J=6 Hz, 2H), 1.94 (t, J=6 Hz, 2H), 1.76 (d, J=8 Hz, 3H), 0.50-0.53 (m, 2H), 0.25-0.28 (m, 2H).

Example 16: Synthesis of 5-(1-(3, 5-dichloropyridin-4-yl)ethoxy)-N-(5-((3S, 5R)-3, 5-dimethylpiperazin-1-yl)pyridin-2-yl)-1H-indazole-3-carboxamide (16)

16

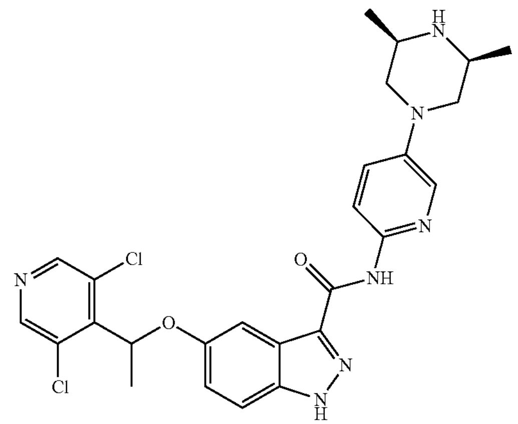

Synthetic Route of Compound 16:

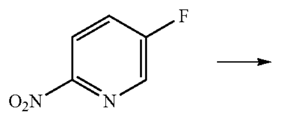

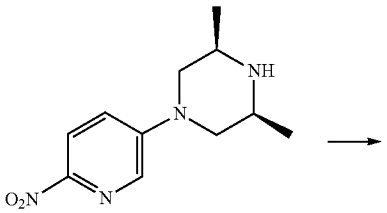

16-1

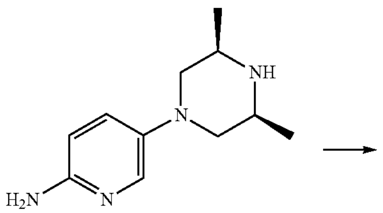

16-2

-continued

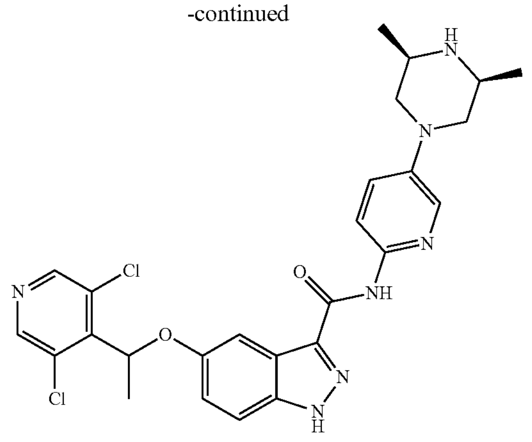

16

Synthesis Method:

Synthesis of Intermediate 16-1: (3S, 5R)-3, 5-dimethyl-1-(6-nitropyridin-3-yl)piperazine 5-Fluoro-2-nitropyridine (100 mg, 0.70 mmol) and (2S, 6R)-2, 6-dimethylpiperazine (88.4 mg, 0.77 mmol) were dissolved in 2 ml DMF, DIPEA (181.6 mg, 1.41 mmol) was added to the solution and it was allowed to react at 50° C. for 3 hours. Water was added to the reaction solution, and the mixture was extracted twice with ethyl acetate, and the resulting organic phases were combined, washed with saturated salt water, dried over anhydrous sodium sulfate, and concentrated to afford 155 mg of Intermediate 16-1 with a yield of 93.2%.

$^1H$ NMR (400 MHz, $CDCl_3$) δ 8.16-8.12 (m, 2H), 7.20-7.17 (m, 1H), 3.76-3.72 (m, 2H), 3.04-2.99 (m, 2H), 2.60-2.54 (m, 2H), 0.90 (dd, J=4 Hz, J=8 Hz, 6H).

Synthetic Intermediate 16-2: 5-((3S, 5R)-3, 5-dimethylpiperazin-1-yl) pyridin-2-amine Intermediate 16-1 (155 mg, 0.66 mmol) was dissolved in 10 ml methanol, 20 mg of 10% palladium carbon was added, the atmosphere was replaced with hydrogen 3 times, and the reaction was carried out at room temperature for 2 h. The mixture was filtered and concentrated to give 130 mg of Intermediate 16-2 with a yield of 96.1%.

Synthesis of compound 16: 5-(1-(3, 5-dichloropyridin-4-yl)ethoxy)-N-(5-((3S, 5R)-3, 5-dimethylpiperazin-1-yl)pyridin-2-yl)-1H-indazole-3-carboxamide Intermediate 5-(1-(3, 5-dichloropyridin-4-yl)ethoxy)-1-(tetrahydro-2H-pyran-2-yl)-1H-indazole-3-carboxylic acid (30 mg, 0.07 mmol) and Intermediate 16-2 (15.6 mg, 0.08 mmol) were dissolved in DMF (1 ml), HATU (31.4 mg, 0.08 mmol) and DIPEA (17.8 mg, 0.14 mmol) were added and it was allowed to react at room temperature for 3 h. Water was added to the reaction solution, the mixture was extracted twice with ethyl acetate, and the resulting organic phases were combined, washed with saturated salt water, dried over sodium sulfate and concentrated. The resulting crude product was dissolved in 2 ml of methanol and 1 ml of concentrated hydrochloric acid, it was allowed to react at 50° C. for 2 h, and the reaction solution was concentrated. The concentrate was dissolved in 3 ml of methanol, 0.5 ml of ammonia was added, and the resulting solution was concentrated and purified by a preparative plate to afford 4 mg of the final product with a total yield of 10.8% in two steps.

$^1$H NMR (400 MHz, DMSO-$d_6$) δ 9.45 (s, 1H), 8.60 (s, 2H), 8.05-8.03 (m, 2H), 7.59 (d, J=8 Hz, 1H), 7.49-7.46 (m, 2H), 7.18 (dd, J=4 Hz, J=8 Hz, 1H), 6.11-6.06 (m, 1H), 3.56-3.51 (m, 2H), 2.90-2.85 (m, 2H), 2.18-2.12 (m, 2H), 1.77 (d, J=8 Hz, 3H), 1.04 (d, J=4 Hz, 6H).

Example 17: Synthesis of 5-(1-(3, 5-dichloropyridin-4-yl)ethoxy)-N-(4-((3S, 5R)-3, 5-dimethylpiperazin-1-yl)-3-fluorophenyl)-1H-indazole-3-carboxamide (17)

17

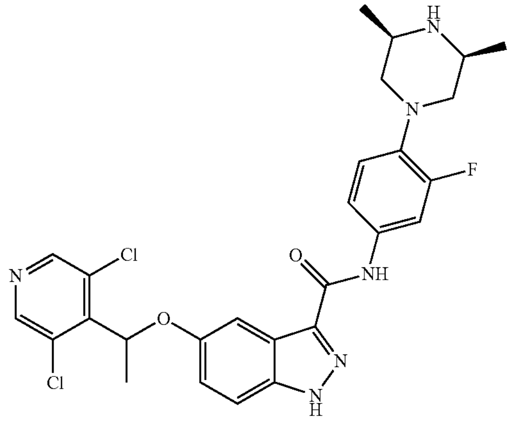

Synthetic Route of Compound 17:

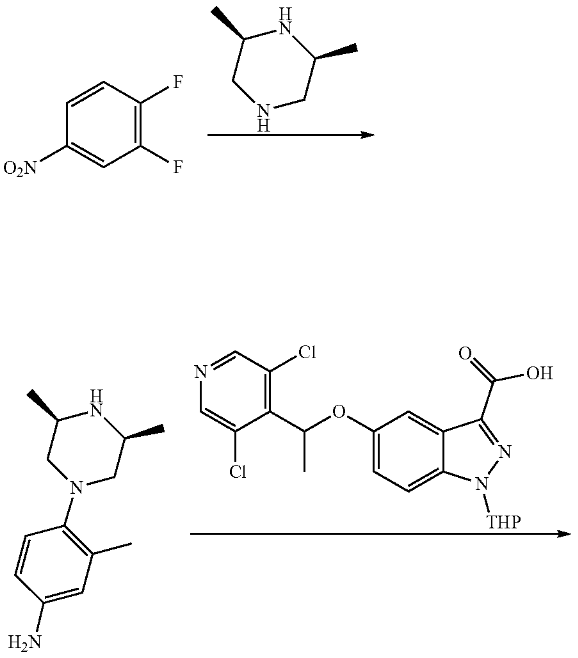

17-1

-continued

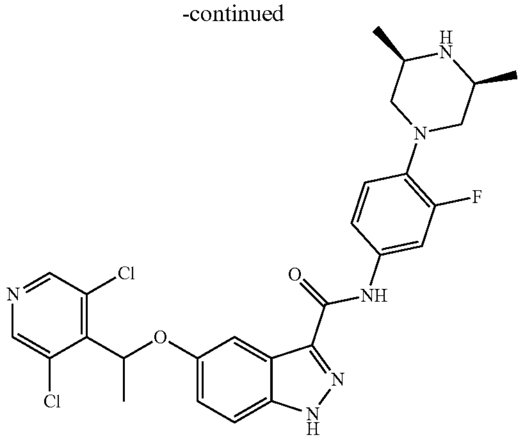

17

Synthesis Method:

Synthesis of Intermediate 17-1: 4-((3S, 5R)-3, 5-dimethylpiperazin-1-yl)-3-fluoroaniline 1, 2-difluoro-4-nitrobenzene (50 mg, 0.31 mmol) and (2S, 6R)-2, 6-dimethylpiperazine (39.5 mg, 0.34 mmol) were dissolved in 5 ml of acetonitrile, DIPEA (81.1 mg, 0.63 mmol) was added to the solution and it was allowed to react at 80° C. for 2 hours. Water was added to the reaction solution, and the mixture was extracted twice with ethyl acetate, and the resulting organic phases were combined, washed with saturated salt water, dried over anhydrous sodium sulfate and concentrated. To the resulting residue, 3 ml of methanol and 5 mg of 10% palladium carbon were added, the atmosphere was replaced by hydrogen three times and the reaction was carried out at 40° C. for 1 h. After the reaction was completed, the reaction mixture was filtered, concentrated and purified on silica gel plate to afford 44 mg of intermediate 17-1 with a yield of 62.7%.

$^1$H NMR (400 MHz, $CDCl_3$) δ 6.79 (t, J=8 Hz, 1H), 6.37-6.43 (m, 2H), 3.07-3.16 (m, 4H), 2.26 (t, J=10 Hz, 2H), 1.10 (d, J=8 Hz, 6H).

Synthesis of compound 17: 5-(1-(3, 5-dichloropyridin-4-yl)ethoxy)-N-(4-((3S, 5R)-3, 5-dimethylpiperazin-1-yl)-3-fluorophenyl)-1H-indazole-3-carboxamide Intermediate 17-1 (18.4 mg, 0.08 mmol) and Intermediate 1-6 (30 mg, 0.06 mmol) were dissolved in DMF (3 ml), HATU (31.4 mg, 0.08 mmol) and DIPEA (17.7 mg, 0.14 mmol) were added, and it was allowed to react at room temperature for 3 h. Water was added to the reaction solution, the mixture was extracted twice with ethyl acetate, and the resulting organic phases were combined, washed with saturated salt water, dried over sodium sulfate, concentrated and purified by silica gel column. The resulting product was dissolved in 2 ml of methanol and 1 ml of concentrated hydrochloric acid, it was allowed to react at 50° C. for 2 h, and the reaction solution was concentrated. The concentrate was dissolved in 3 ml of methanol, 0.5 ml of ammonia was added, and the resulting solution was concentrated and purified by a preparative plate to afford 10 mg of the final product with a yield of 26.1%.

$^1$H NMR (400 MHz, $CDCl_3$) δ 10.48 (s, 1H), 8.71 (s, 1H), 8.43 (s, 2H), 7.77 (s, 1H), 7.67 (d, J=12 Hz, 1H), 7.39 (d, J=8

Hz, 1H), 7.16-7.24 (m, 2H), 6.94 (t, J=10 Hz, 1H), 6.13-6.18 (m, 1H), 3.28-3.31 (m, 2H), 3.16-3.20 (m, 2H), 2.40 (m, 2H), 1.81 (d, J=8 Hz, 3H), 1.18 (d, J=4 Hz, 6H).

Example 18: Synthesis of 5-(1-(3, 5-dichloropyridin-4-yl)ethoxy)-N-(4-(1-ethylpiperidin-4-yl)phenyl)-1H-indazole-3-carboxamide (18)

18

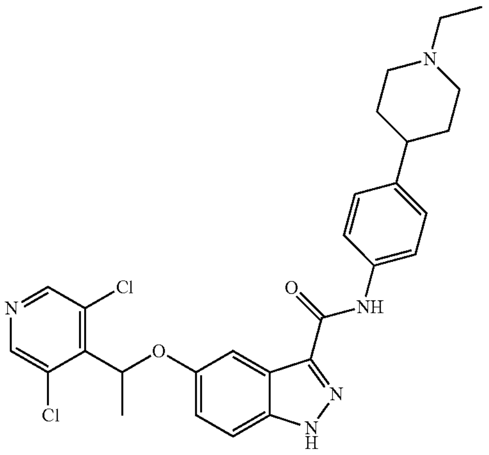

Synthetic Route of Compound 18:

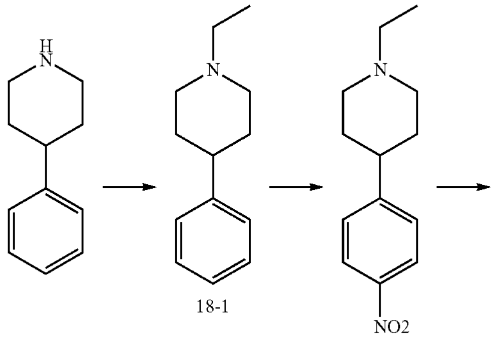

18-1

18-2

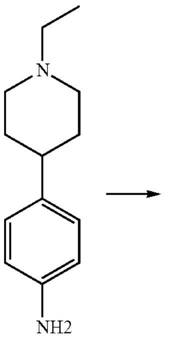

-continued

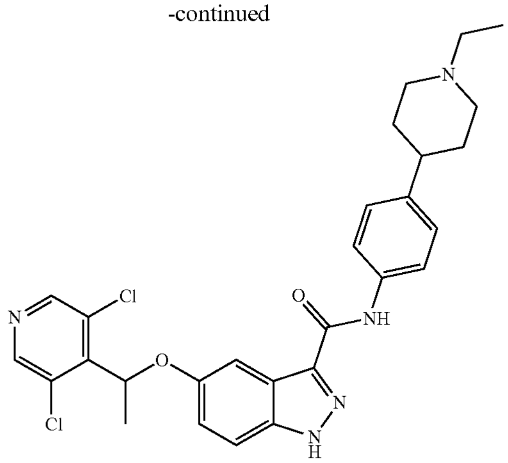

18

Synthesis Method:

Synthesis of Intermediate 18-1: 1-ethyl-4-phenylpiperidine

4-Phenylpiperidine (100 mg, 0.62 mmol) and triethylamine (188.4 mg, 1.86 mmol) were dissolved in 10 ml of dichloromethane and acetyl chloride (58.4 mg, 0.74 mmol) was added dropwise to the solution and the reaction was carried out at room temperature for 1 hour. Water was added to the reaction solution, the reaction solution was washed with saturated salt water, dried over anhydrous sodium sulfate, and concentrated. The resulting solid was dissolved in dry THF, and cooled to 0° C. Lithium tetrahydroaluminum (61.7 mg, 1.62 mmol) was added and it was allowed to react at room temperature for 3 h. The reaction was quenched by adding a small amount of water, and anhydrous sodium sulfate was added while stirring for 20 min. The resulting mixture was filtered and concentrated to give 96 mg of Intermediate 18-1 with a total yield of 82.1% in two steps.

$^1$H NMR (400 MHz, $CDCl_3$) δ 7.32-7.19 (m, 5H), 3.11-3.06 (m, 2H), 2.50-2.42 (m, 3H), 2.05-2.01 (m, 2H), 1.99-1.79 (m, 4H), 1.11 (t, J=8 Hz, 3H).

Synthetic intermediate 18-2: 1-ethyl-4-(4-nitrophenyl)piperidine

Intermediate 18-1 (96 mg, 0.51 mmol) was dissolved in 196 mg concentrated sulfuric acid, and cooled to 0° C., to which concentrated nitric acid (56.7 mg, 0.90 mmol) was added dropwise, and it was allowed to react overnight at room temperature. Water was added to the reaction solution and the mixture was adjusted to pH=8 with sodium hydroxide solution. The resulting solution was extracted with ethyl acetate, washed with saturated salt water, dried over anhydrous sodium sulfate, and concentrated to give 83 mg of Intermediate 18-2 with a yield of 70.9% N.

$^1$H NMR (400 MHz, $CDCl_3$) δ 8.17 (d, J=8 Hz, 2H), 7.39 (d, J=8 Hz, 2H), 3.13-3.10 (m, 2H), 2.64-2.60 (m, 1H), 2.50-2.45 (m, 2H), 2.07-2.01 (m, 2H), 1.89-1.81 (m, 4H), 1.13 (t, J=8 Hz, 3H).

Synthetic intermediate 18-3: 4-(1-ethylpiperidin-4-yl)aniline

Intermediate 18-2 (83 mg, 0.35 mmol) was dissolved in 10 ml of methanol, 8 mg of 10% palladium carbon was added, the atmosphere was replaced with hydrogen 3 times, and the reaction was carried out at room temperature for 2 h. The reaction mixture was filtered and concentrated to give 49 mg of Intermediate 18-3 with a yield of 67.7%.

Synthesis of compound 18: 5-(1-(3, 5-dichloropyridin-4-yl)ethoxy)-N-(4-(1-ethylpiperidin-4-yl)phenyl)-1H-indazole-3-carboxamide Intermediate 5-(1-(3, 5-dichloropyridin-4-yl)ethoxy)-1-(tetrahydro-2H-pyran-2-yl)-1H-indazole-3-carboxylic acid (30 mg, 0.07 mmol) and Intermediate 18-3 (15.5 mg, 0.08 mmol) were dissolved in DMF (1 ml), HATU (31.4 mg, 0.08 mmol) and DIPEA (17.8 mg, 0.14 mmol) were added and it was allowed to react at room temperature for 3 h. Water was added to the reaction solution, the mixture was extracted twice with ethyl acetate, and the resulting organic phases were combined, washed with saturated salt water, dried over sodium sulfate and concentrated. The resulting crude product was dissolved in 2 ml of methanol and 1 ml of concentrated hydrochloric acid, it was allowed to react at 50° C. for 2 h, and the reaction solution was concentrated. The concentrate was dissolved in 3 ml of methanol, 0.5 ml of ammonia was added, and the resulting solution was concentrated and purified by a preparative plate to afford 11 mg of the final product with a total yield of 29.7% in two steps.

$^1$H NMR (400 MHz, DMSO-$d_6$) δ 13.65 (s, 1H), 10.10 (s, 1H), 8.60 (s, 2H), 7.74 (d, J=8 Hz, 2H), 7.58 (d, J=8 Hz, 1H), 7.51 (d, J=4 Hz, 1H), 7.22 (d, J=8 Hz, 2H), 7.17-7.14 (m, 1H), 6.10-6.07 (m, 1H), 3.00-2.97 (m, 2H), 2.50-2.46 (m, 1H), 2.37-2.33 (m, 2H), 2.01-1.94 (m, 3H), 1.77 (d, J=8 Hz, 3H), 1.68-1.63 (m, 3H), 1.04 (t, J=8 Hz, 3H).

Example 19: Synthesis of 5-(1-(3, 5-dichloropyridin-4-yl)ethoxy)-N-(1-(2-morpholinoethyl)-1H-pyrazol-4-yl)-1H-indazole-3-carboxamide (19)

19

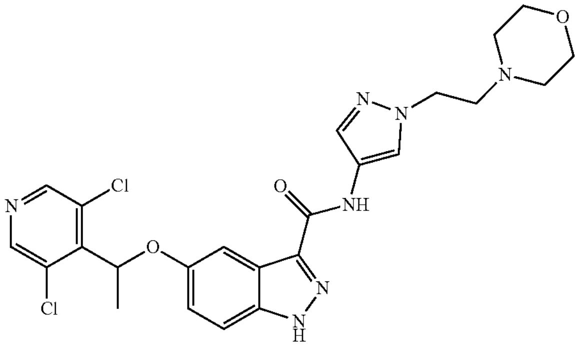

Synthetic Route of Compound 19:

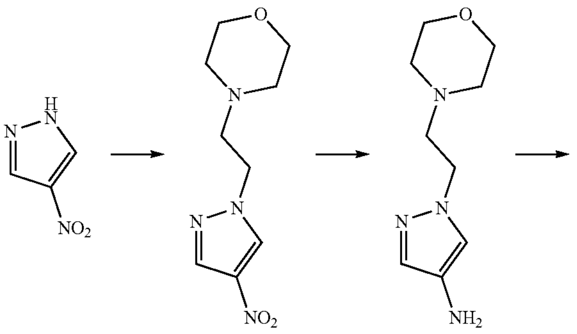

19-1

19-2

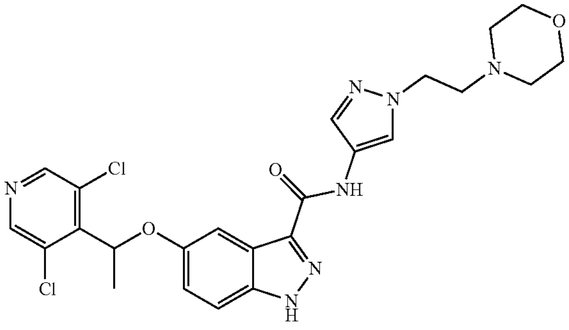

19

Synthesis Method:

Synthesis of Intermediate 19-1: 4-(2-(4-nitro-1H-pyrazol-1-yl)ethyl) morpholine

4-Nitro-1H-pyrazole (70 mg, 0.62 mmol) was dissolved in 10 ml of acetonitrile and potassium carbonate (256.7 mg, 1.86 mmol) and 4-(2-bromoethyl)morpholine hydrobromide (187.7 mg, 0.68 mmol) were added to the reaction solution and it was allowed to react at 80° C. for 4 hours. After the reaction was completed, 50 ml of water was added to the system, the mixture was extracted with ethyl acetate, and the organic phase was washed with saturated salt water, dried over anhydrous sodium sulfate and concentrated by column chromatography to give 103 mg of Intermediate 19-1 with a yield of 73.5%.

$^1$H NMR (400 MHz, $CDCl_3$) δ 8.28 (s, 1H), 8.08 (s, 1H), 4.27 (t, J=8 Hz, 2H), 3.73-3.71 (m, 4H), 2.84 (t, J=8 Hz, 2H), 2.52-2.50 (m, 4H).

Synthesis of Intermediate 19-2: 1-(2-morpholinoethyl)-1H-pyrazol-4-amine

Intermediate 19-1 (103 mg, 0.46 mmol) was dissolved in 10 ml of methanol, 10 mg of 10% palladium carbon was added, the atmosphere was replaced with hydrogen 3 times, the reaction was carried out at room temperature for 2 h. The reaction mixture was filtered and concentrated to give 92 mg of Intermediate 19-2 with a yield of 91.8%.

Synthesis of compound 19: 5-(1-(3, 5-dichloropyridin-4-yl)ethoxy)-N-(1-(2-morpholinoethyl)-1H-pyrazol-4-yl)-1H-indazole-3-carboxamide Intermediate 5-(1-(3, 5-dichloropyridin-4-yl)ethoxy)-1-(tetrahydro-2H-pyran-2-yl)-1H-indazole-3-carboxylic acid (30 mg, 0.07 mmol) and Intermediate 19-2 (16.2 mg, 0.08 mmol) were dissolved in DMF (1 ml), HATU (31.4 mg, 0.08 mmol) and DIPEA (17.8 mg, 0.14 mmol) were added and it was allowed to react at room temperature for 3 h. Water was added to the reaction solution, the mixture was extracted twice with ethyl acetate, and the resulting organic phases were combined, washed with saturated salt water, dried over sodium sulfate and concentrated. The resulting crude product was dissolved in 2 ml of methanol and 1 ml of concentrated hydrochloric acid, it was allowed to react at 50° C. for 2 h, and the reaction solution was concentrated. The concentrate was dissolved in 3 ml of methanol, 0.5 ml of ammonia was added, and the resulting solution was concentrated and purified by a preparative plate to afford 23 mg of the final product with a total yield of 63.0% in two steps.

$^{1}$H NMR (400 MHz, MeOD-$d_4$) δ 8.48 (s, 2H), 8.17 (s, 1H), 7.70 (s, 1H), 7.60 (d, J=4 Hz, 1H), 7.51 (d, J=8 Hz, 1H), 7.20 (dd, J=4 Hz, J=8 Hz, 1H), 6.21-6.16 (m, 1H), 4.31 (t, J=4 Hz, 2H), 3.74-3.71 (m, 4H), 2.84 (t, J=8 Hz, 2H), 2.55-2.52 (m, 4H), 1.83 (d, J=4 Hz, 3H).

Example 20: Synthesis of 5-(1-(3, 5-dichloropyridin-4-yl)ethoxy)-N-(1-ethyl-1H-pyrazol-4-yl)-1H-indazole-3-carboxamide (20)

20

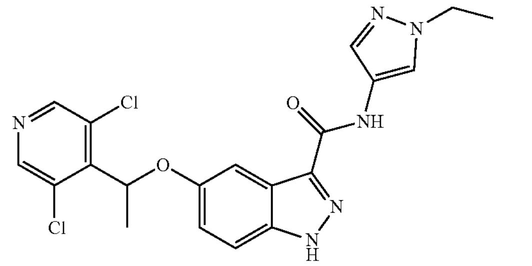

Synthetic Route of Compound 20:

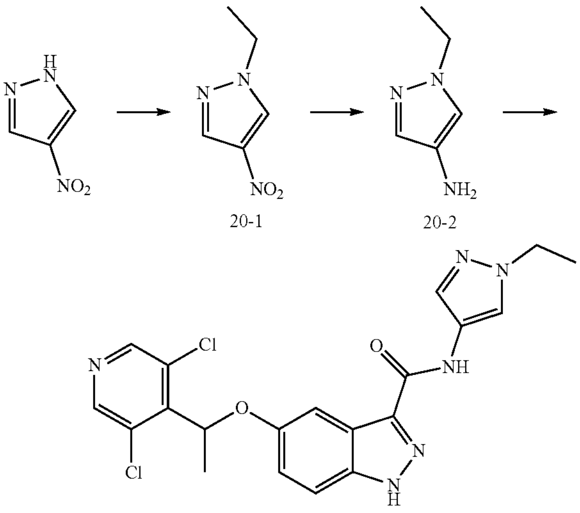

20-1

20-2

20

Synthesis Method:

Synthesis of Intermediate 20-1: 1-ethyl-4-nitro-1H-pyrazole

4-Nitro-1H-pyrazole (100 mg, 0.88 mmol) was dissolved in 15 ml of acetonitrile and potassium carbonate (366.7 mg, 2.65 mmol) and bromoethane (217.6 mg, 1.77 mmol) were added to the reaction solution and it was allowed to react at 80° C. After the reaction was completed, 50 ml of water was added to the system, the mixture was extracted with ethyl acetate, and the organic phase was washed with saturated salt water, dried over anhydrous sodium sulfate, and concentrated by column chromatography to afford 110 mg of Intermediate 20-1 with a yield of 88.1%.

$^{1}$H NMR (400 MHz, $CDCl_3$) δ 8.16 (s, 1H), 8.10 (s, 1H), 4.27 (dd, J=8 Hz, J=12 Hz, 2H), 1.59-1.56 (m, 3H).

Synthetic Intermediate 20-2: 1-ethyl-1H-pyrazol-4-amine

Intermediate 20-1 (110 mg, 0.78 mmol) was dissolved in 10 ml of methanol, 20 mg of 10% palladium carbon was added, the atmosphere was replaced with hydrogen three times, and the reaction was carried out at room temperature for 2 h. The reaction mixture was filtered and concentrated to give 73 mg of intermediate 20-2 with a yield of 84.3%.

Synthesis of compound 20: 5-(1-(3, 5-dichloropyridin-4-yl)ethoxy)-N-(1-ethyl-1H-pyrazol-4-yl)-1H-indazole-3-carboxamide Intermediate 5-(1-(3, 5-dichloropyridin-4-yl)ethoxy)-1-(tetrahydro-2H-pyran-2-yl)-1H-indazole-3-carboxylic acid (30 mg, 0.07 mmol) and Intermediate 2 (8.4 mg, 0.08 mmol) were dissolved in DMF (1 ml), HATU (31.4 mg, 0.08 mmol) and DIPEA (17.8 mg, 0.14 mmol) were added and it was allowed to react at room temperature for 3 h. Water was added to the reaction solution, the mixture was extracted twice with ethyl acetate, and the resulting organic phases were combined, washed with saturated salt water, dried over sodium sulfate and concentrated. The resulting crude product was dissolved in 2 ml of methanol and 1 ml of concentrated hydrochloric acid, it was allowed to react at 50° C. for 2 h, and the reaction solution was concentrated. The concentrate was dissolved in 3 ml of methanol, 0.5 ml of ammonia was added, and the resulting solution was concentrated and purified by a preparative plate to afford 19 mg of the final product with a total yield of 62.0% in two steps.

$^{1}$H NMR (400 MHz, MeOD-$d_4$) δ 8.48 (s, 2H), 8.08 (s, 1H), 7.70 (s, 1H), 7.60 (d, J=4 Hz, 1H), 7.51 (d, J=8 Hz, 1H), 7.20 (dd, J=4 Hz, J=8 Hz, 1H), 6.21-6.16 (m, 1H), 4.24 (dd, J=8 Hz, J=16 Hz, 2H), 1.85 (d, J=8 Hz, 3H), 1.52 (t, J=8 Hz, 3H).

Example 21: Synthesis of 5-(1-(3, 5-dichloropyridin-4-yl)ethoxy)-N-(1-(1-methylazetidin-3-yl)-1H-pyrazol-4-yl)-1H-indazole-3-carboxamide (21)

21

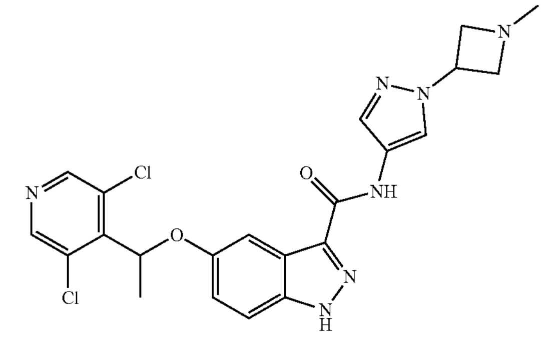

Synthetic Route of Compound 21:

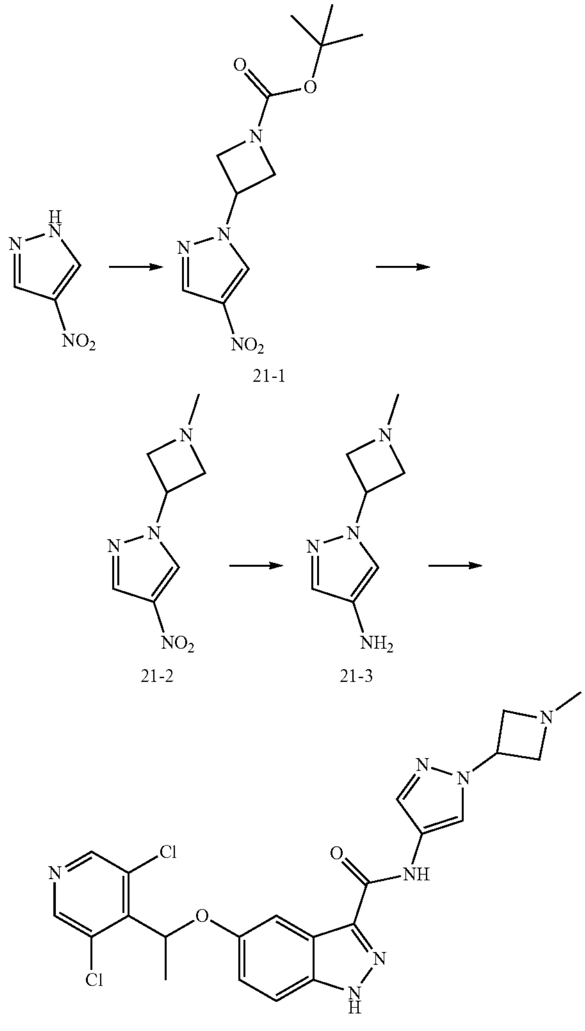

21-1

21-2

21-3

21

Synthesis Method.

Synthesis of Intermediate 21-1: tert-butyl 3-(4-nitro-1H-pyrazol-1-yl)azetidine-1-carboxylate 4-Nitro-1H-pyrazole (230 mg, 2.04 mmol) was dissolved in 4 ml DMF, cesium carbonate (1.33 g, 4.08 mmol) and tert-butyl 3-((methylsulfonyl)oxy)azetidine-1-carboxylate (614.4 mg, 2.45 mmol) were added to the reaction solution and it was allowed to react at 100° C. overnight. After the reaction was completed, 50 ml of water was added to the system, the mixture was extracted with ethyl acetate, and the organic phase was washed with saturated salt water, dried over anhydrous sodium sulfate, and concentrated by column chromatography to afford 480 mg of Intermediate 21-1 with a yield of 87.6%.

$^1H$ NMR (400 MHz, $CDCl_3$) δ 8.30 (s, 1H), 8.18 (s, 1H), 5.09-5.05 (m, 1H), 4.47-4.42 (m, 2H), 4.36-4.33 (m, 2H), 1.46 (s, 9H).

Synthetic intermediate 21-2: 1-(1-methylazetidin-3-yl)-4-nitro-1H-pyrazole

Intermediate 21-1 (460 mg, 1.72 mmol) was dissolved in 10 ml of dichloromethane, 2.5 ml of trifluoroacetic acid was added and it was allowed to react at room temperature for 0.5 h. The reaction solution was concentrated, and the resulting residue was dissolved with dichloromethane, adjusted to pH=8 with saturated sodium bicarbonate solution, and extracted three times with dichloromethane. The resulting organic phases were combined, dried over anhydrous sodium sulfate, and concentrated. The obtained product (83 mg, 0.49 mmol) was dissolved with dichloromethane, aqueous formaldehyde solution (0.12 ml, 1.48 mmol) was added, and the mixture was stirred for 20 min at room temperature. $NaBH(OAc)_3$ (627.9 mg, 2.96 mmol) was added, and the mixture was stirred for 2 h at room temperature and extracted with water, dried over anhydrous sodium sulfate and concentrated to give Intermediate 21-2 of 42 mg in a total yield of 13.5% in two steps.

$^1H$ NMR (400 MHz, $CDCl_3$) δ 8.39 (s, 1H), 8.13 (s, 1H), 4.97-4.90 (m, 1H), 3.83-3.79 (m, 2H), 3.58-3.54 (m, 2H), 2.47 (s, 3H).

Synthesis of Intermediate 21-3: 1-(1-methylazetidin-3-yl)-1H-pyrazol-4-amine

Intermediate 21-2 (42 mg, 0.23 mmol) was dissolved in 5 ml methanol, 5 mg 10% palladium carbon was added, the atmosphere was replaced with hydrogen 3 times, and the reaction was carried out at room temperature for 2 h. The reaction mixture was filtered and concentrated to give 29 mg of Intermediate 21-3 with a yield of 82.9%.

Synthesis of compound 21: 5-(1-(3, 5-dichloropyridin-4-yl)ethoxy)-N-(1-(1-methylazetidin-3-yl)-1H-pyrazol-4-yl)-1H-indazole-3-carboxamide Intermediate 5-(1-(3, 5-dichloropyridin-4-yl)ethoxy)-1-(tetrahydro-2H-pyran-2-yl)-1H-indazole-3-carboxylic acid (30 mg, 0.07 mmol) and Intermediate 21-3 (12.6 mg, 0.08 mmol) were dissolved in DMF (1 ml), HATU (31.4 mg, 0.08 mmol) and DIPEA (17.8 mg, 0.14 mmol) were added and it was allowed to react at room temperature for 3 h. Water was added to the reaction solution, the mixture was extracted twice with ethyl acetate, and the resulting organic phases were combined, washed with saturated salt water, dried over sodium sulfate and concentrated. The resulting crude product was dissolved in 2 ml of methanol and 1 ml of concentrated hydrochloric acid, it was allowed to react at 50° C. for 2 h, and the reaction solution was concentrated. The concentrate was dissolved in 3 ml of methanol, 0.5 ml of ammonia was added, and the resulting solution was concentrated and purified by a preparative plate to afford 3.6 mg of the final product with a total yield of 10.8% in two steps.

$^1$H NMR (400 MHz, MeOD-$d_4$) δ 8.48 (s, 2H), 8.19 (s, 1H), 7.79 (s, 1H), 7.60 (d, J=4 Hz, 1H), 7.51 (d, J=8 Hz, 1H), 7.20 (dd, J=4 Hz, J=8 Hz, 1H), 6.21-6.16 (m, 1H), 5.06-5.02 (m, 1H), 3.94-3.90 (m, 2H), 3.68-3.65 (m, 2H), 2.52 (s, 3H), 1.52 (d, J=4 Hz, 3H). LC-MS: $C_{22}H_{22}Cl_2N_7O_2$ $[M+H]^+$ m/z calculated as 486.1, detected as 486.1.

Example 22: Synthesis of 5-(1-(3,5-dichloropyridin-4-yl)ethoxy)-N-(1-(((1-methylpiperidin-4-yl)methyl)-1H-pyrazol-4-yl)-1H-indazole-3-carboxamide (22)

22

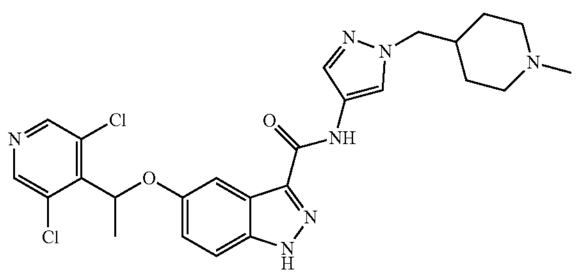

Synthetic Route of Compound 22:

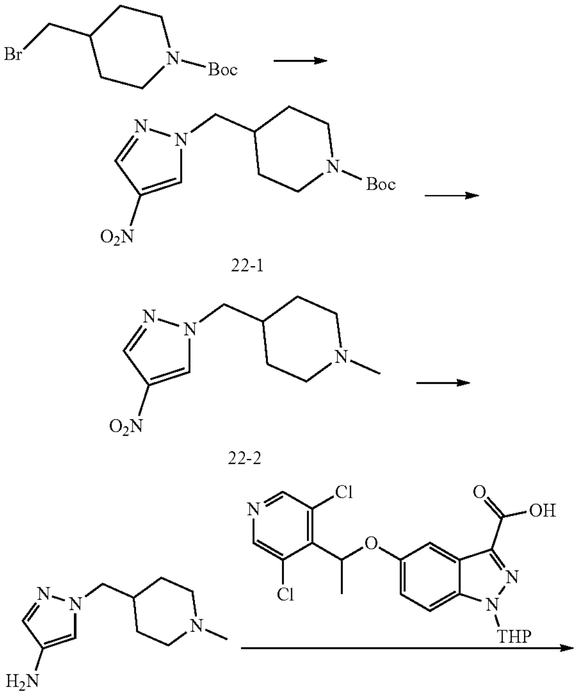

22-1

22-2

22-3

-continued

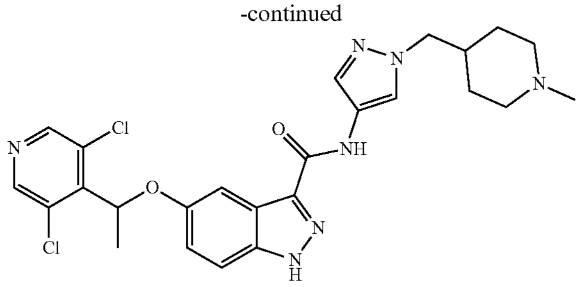

22

Synthesis Method:

Synthesis of intermediate 22-1: tert-butyl 4-((4-nitro-1H-pyrazol-1-yl)methyl)piperidine-1-carboxylate Tert-butyl 4-(bromomethyl)piperidine-1-carboxylate (130.0 mg, 0.47 mmol) and 4-nitro-1H-pyrazole (48.0 mg, 0.42 mmol) were dissolved in 20 ml of acetonitrile, cesium carbonate (276.8 mg, 0.85 mmol) was added to the reaction solution and it was allowed to react at 80° C. for 2 hours. After the reaction was completed, water was added to the system, the system was extracted with ethyl acetate, and partitioned, and the organic phase was washed with saturated salt water, dried over anhydrous sodium sulfate, concentrated and purified by column chromatography to afford 130.3 mg of Intermediate 22-1 with a yield of 98.6%.

Synthesis Intermediate 22-2: 1-methyl-4-((4-nitro-1H-pyrazol-1-yl)methyl)piperidine Intermediate 22-1 (130.3 mg, 0.41 mmol) was dissolved in 10 ml of dichloromethane, 2 ml of trifluoroacetic acid was added to the solution, and it was allowed to react for 30 minutes at room temperature. The reaction solution was concentrated, the concentrate was dissolved in 10 ml of dichloromethane, aqueous formaldehyde solution (0.10 ml, 1.25 mmol) was added, and the mixture was stirred for 20 min at room temperature. $NaBH(OAc)_3$ (265.1 mg, 1.25 mmol) was added, and the mixture was stirred for 2 h at room temperature, extracted with water, dried over anhydrous sodium sulfate and concentrated to give 90.2 mg of Intermediate 22-2 with a yield of 95.8%.

$^1$H NMR (400 MHz, MeOD-$d_4$) δ 8.61 (s, 1H), 8.14 (s, 1H), 4.14 (d, J=7.2 Hz, 2H), 3.09-3.04 (m, 2H), 2.44 (s, 3H), 2.32-2.21 (m, 2H), 2.08-2.01 (m, 1H), 1.71-1.66 (m, 2H), 1.48-1.40 (m, 2H).

Synthesis of compound 22-3: 1-((1-methylpiperidin-4-yl)methyl)-1H-pyrazol-4-amine Intermediate 22-2 (50.0 mg, 0.22 mmol) was dissolved in 5 ml of methanol, 5 mg of 10% palladium carbon was added, the atmosphere was replaced with hydrogen three times and the reaction was carried out at room temperature for 2 h. The reaction solution was filtered and the filtrate was concentrated to give 42.9 mg of Intermediate 22-3 with a yield of 99.2%.

Synthesis of compound 22: 5-(1-(3,5-dichloropyridin-4-yl)ethoxy)-N-(1-(((1-methylpiperidin-4-yl)methyl)-1H-pyrazol-4-yl)-1H-indazole-3-carboxamide Intermediate 5-(1-(3, 5-dichloropyridin-4-yl)ethoxy)-1-(tetrahydro-2H-pyran-2-yl)-1H-indazole-3-carboxylic acid (30 mg, 0.07 mmol) and Intermediate 22-3 (14.7 mg, 0.08 mmol) were dissolved in 5 ml DMF, HATU (31.4 mg, 0.08 mmol) and DIPEA (17.8 mg, 0.14 mmol) were added and it was allowed to react at room temperature for 3 h. Water was added to the reaction solution, the mixture was extracted twice with ethyl acetate, and the resulting organic phases were combined, washed with saturated salt water, dried over anhydrous sodium sulfate and concentrated. The resulting crude product was dissolved in 2 ml of methanol and 1 ml of concentrated hydrochloric acid, it was allowed to react at 50° C. for 2 h, and the reaction solution was concentrated. The concentrate was dissolved in 3 ml of methanol, 0.5 ml of ammonia was added, and the resulting solution was concentrated and purified by a preparative plate to afford 7.6 mg of the final product with a total yield of 35.2% in two steps.

$^1$H NMR (400 MHz, MeOD-$d_4$) δ 8.47 (s, 2H), 8.08 (s, 1H), 7.71 (s, 1H), 7.59 (d, J=2.4 Hz, 1H), 7.50 (d, J=9.1 Hz, 1H), 7.18 (dd, J=9.1 Hz, 2.4 Hz, 1H), 6.18 (q, J=6.6 Hz, 1H), 4.06 (d, J=7.2 Hz, 2H), 2.94 (d, J=11.7 Hz, 2H), 2.32 (s, 3H), 2.09 (t, J=11.3 Hz, 2H), 2.00-1.89 (m, 1H), 1.83 (d, J=6.7 Hz, 3H), 1.64 (d, J=13.1 Hz, 2H), 1.44-1.37 (m, 2H).

Example 23: 5-(1-(3,5-dichloropyridin-4-yl)ethoxy)-N-(1-(2-oxo-2-(pyrrolidin-1-yl)ethyl)-1H-pyrazol-4-yl)-1H-indazole-3-carboxamide

23

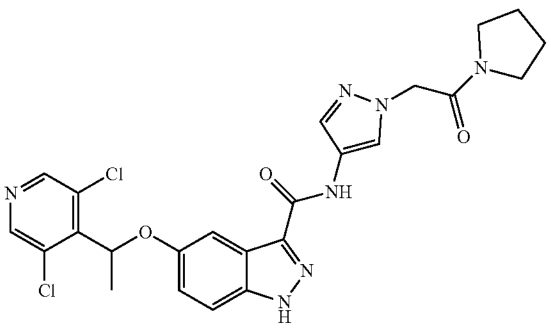

Synthetic Route of Compound 23:

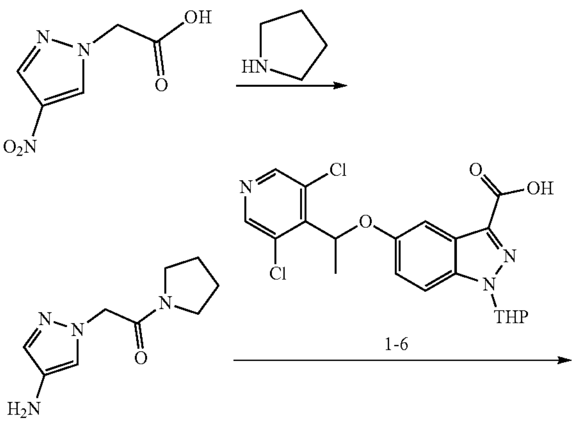

23-1

-continued

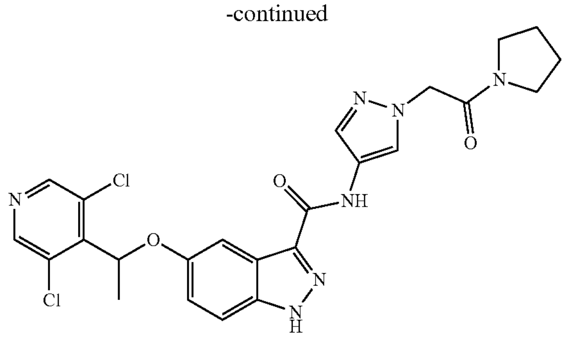

23

Synthesis Method:

Synthesis of Intermediate 23-1: 2-(4-amino-1H-pyrazol-1-yl)-1-(pyrrolidin-1-yl)ethan-1-one 2-(4-Nitro-1H-pyrazol-1-yl)acetic acid (50 mg, 0.29 mmol) and pyrrolidine (24.9 mg, 0.35 mmol) were dissolved in DMF, HATU (133.3 mg, 0.35 mmol) and DIPEA (75.4 mg, 0.58 mmol) were added to the solution, and it was allowed to react for 3 h at room temperature. Water was added to the reaction solution, the mixture was extracted twice with ethyl acetate, and the resulting organic phases were combined, washed with saturated salt water, dried over anhydrous sodium sulfate, concentrated and purified by silica gel plate. The resulting product was dissolved in 3 ml of methanol, 5 mg of 10% palladium carbon was added, the atmosphere was replaced with hydrogen, and the reaction was carried out at 40° C. for 1 h. After the reaction was completed, the product was filtered, concentrated and purified on silica gel plate to afford 40 mg of Intermediate 23-1 with a yield of 70.4%.

$^1$H NMR (400 MHz, $CDCl_3$) δ 7.17 (d, J=4 Hz, 2H), 4.78 (s, 2H), 3.42-3.50 (m, 4H), 2.00-1.93 (m, 2H), 1.88-1.81 (m, 2H).

Synthesis of compound 23: 5-(1-(3,5-dichloropyridin-4-yl)ethoxy)-N-(1-(2-oxo-2-(pyrrolidin-1-yl)ethyl)-1H-pyrazol-4-yl)-1H-indazole-3-carboxamide Intermediate 23-1 (16.0 mg, 0.08 mmol) and Intermediate 1-6 (30 mg, 0.07 mmol) were dissolved in DMF (3 ml), HATU (31.3 mg, 0.08 mmol) and DIPEA (17.7 mg, 0.14 mmol) were added, and it was allowed to react at room temperature for 3 h. Water was added to the reaction solution, the mixture was extracted twice with ethyl acetate, and the resulting organic phases were combined, washed with saturated salt water, dried over anhydrous sodium sulfate, concentrated and purified by silica gel column. The resulting product was dissolved in 2 ml of methanol and 1 ml of concentrated hydrochloric acid, it was allowed to react at 50° C. for 2 h, and the reaction solution was concentrated. The concentrate was dissolved in 3 ml of methanol, 0.5 ml of ammonia was added, and the resulting solution was concentrated and purified by a preparative plate to afford 6 mg of the final product with a yield of 16.5%.

$^1$H NMR (400 MHz, DMSO) δ 13.62 (s, 1H), 10.45 (s, 1H), 8.60 (s, 2H), 8.03 (s, 1H), 7.66 (s, 1H), 7.57-7.54 (m, 2H), 7.17-7.14 (m, 1H), 6.11-6.06 (m, 1H), 5.01 (s, 2H), 3.49 (t, J=8 Hz, 2H), 3.36-3.34 (m, 2H), 1.96-1.89 (m, 2H), 1.83-1.76 (m, 5H).

Examples 24 to 30

Each compound shown in the table below was prepared via a synthetic route and method similar to that of Example 23 by varying the starting materials, and their $^1$H NMR and/or mass spectrometry data were measured.

| Examples | $^1$HNMR(400 MHz) | LC-MS Theoretical Calculated values $(M+1)^+$ | LC-MS Measured values $(M+1)^+$ |
|---|---|---|---|
| 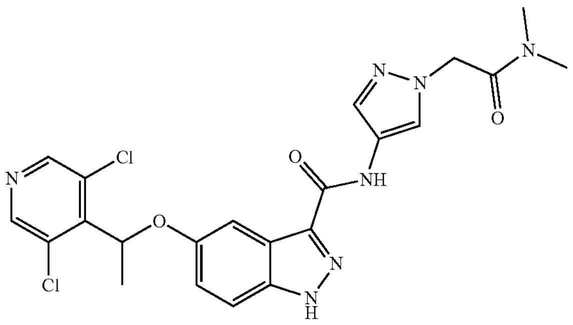 24 Example 24: 5-(1-(3,5-dichloropyridin-4-yl)ethoxy)-N-(1-(2-(dimethylamino)-2-oxoethyl)-1H-pyrazol-4-yl)-1H-indazole-3-carboxamide | (MeOD)δ 8.47 (s, 2H), 8.11 (s, 1H), 7.75 (s, 1H), 7.60 (d, J = 4.0 Hz, 1H), 7.51 (d, J = 8.0 Hz, 1H), 7.19-7.17 (m, 1H), 6.20-6.15 (m, 1H), 5.15 (s, 2H), 3.15 (s, 3H), 3.01 (s, 3H), 1.83 (d, J = 8.0 Hz, 3H). | | |
| 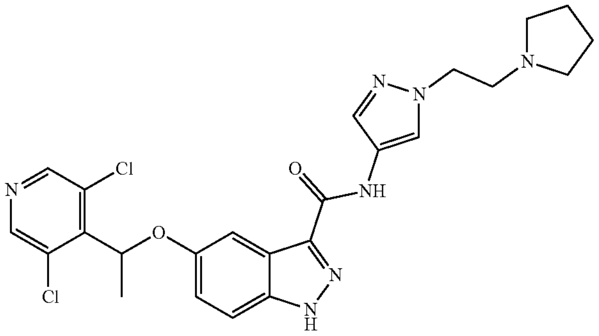 25 Example 25: 5-(1-(3,5-dichloropyridin-4-yl)ethoxy)-N-(1-(2-(pyrrolidin-1-yl)ethyl)-1H-pyrazol-4-yl)-1H-indazole-3-carboxamide | | 514.1 | 514.1 |
| 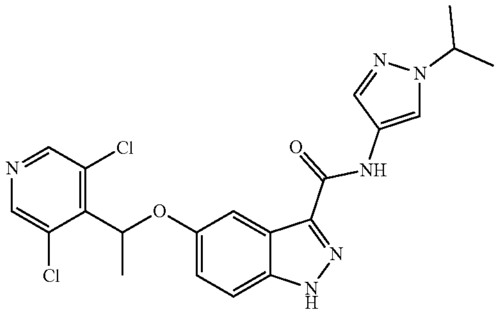 26 Example 26: 5-(1-(3,5-dichloropyridin-4-yl)ethoxy)-N-(1-isopropyl-1H-pyrazol-4-yl)-1H-indazole-3-carboxainide | | 459.1 | 459.1 |

-continued

| Examples | $^1$HNMR(400 MHz) | LC-MS Theoretical Calculated values $(M + 1)^+$ | LC-MS Measured values $(M + 1)^+$ |
|---|---|---|---|
| 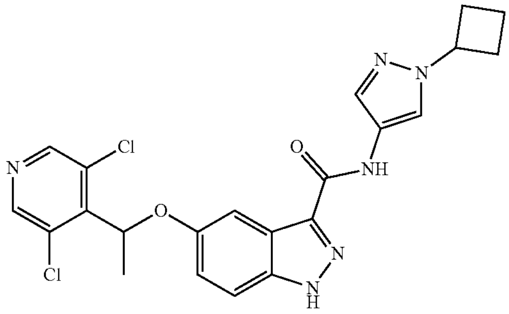<br>27<br>Example 27: N-(1-cyclobutyl-1H-pyrazol-4-yl)-5-(1-(3,5-dichloropyridin-4-yl)ethoxy)-1H-indazole-3-carboxamide | | 471.1 | 471.1 |
| 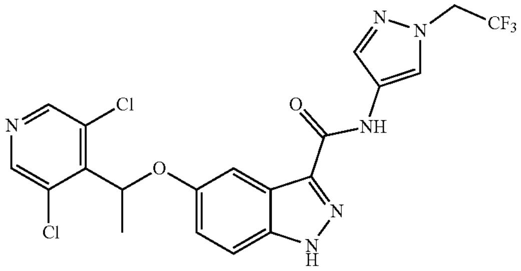<br>28<br>Example 28: 5-(1-(3,5-dichloropyridin-4-yl)ethoxy)-N-(1-(2,2,2-trifluoroethyl)-1H-pyrazol-4-yl)-1H-indazole-3-carboxamide | | 499.1 | 499.0 |
| 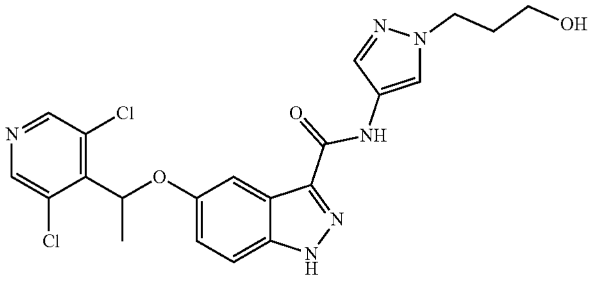<br>29<br>Example 29: 5-(1-(3,5-dichloropyridin-4-yl)ethoxy)-N-(1-(3-hydroxypropyl)-1H-pyrazol-4-yl)-1H-indazole-3-carboxamide | | 475.1 | 475.1 |

-continued

| Examples | $^1$HNMR(400 MHz) | LC-MS Theoretical Calculated values $(M+1)^+$ | LC-MS Measured values $(M+1)^+$ |
|---|---|---|---|
| 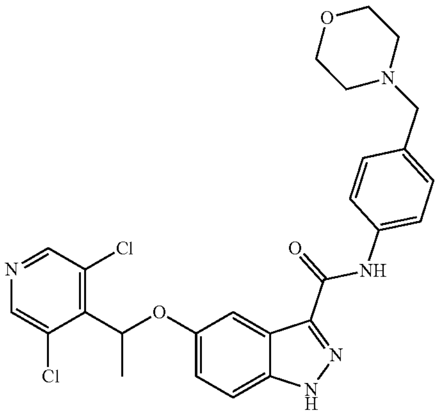 30 Example 30: 5-(1-(3,5-dichloropyridin-4-yl)ethoxy)-N-(4-(morpholinomethyl)phenyl)-1H-indazole-3-carboxamide | | 526.1 | 526.1 |

Example 31: (R)-5-(1-(3,5-dichloropyridin-4-yl)ethoxy)-N-(1-(1-ethyl-azetidin-3-yl)-1H-pyrazol-4-yl)-1H-indazole-3-carboxamide

31

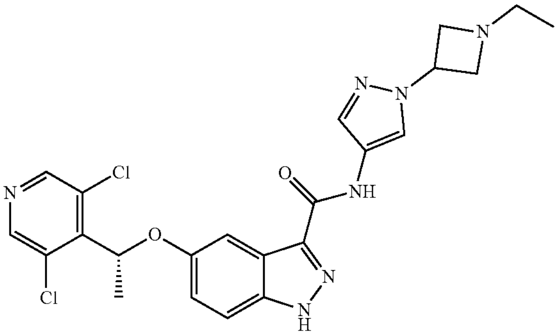

Synthetic Route of Compound 31

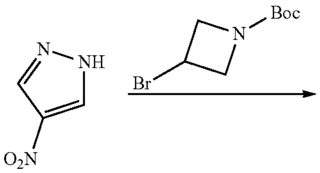

-continued

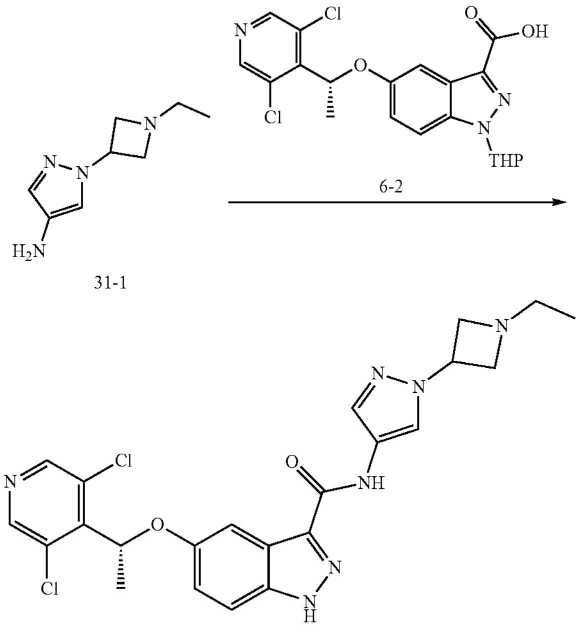

31

Synthesis Method:

Synthesis of Intermediate 31-1: 1-(1-ethylazetidin-3-yl)-1H-pyrazol-4-amine

4-Nitro-1H-pyrazole (50 mg, 0.44 mmol) and tert-butyl 3-bromoazetidine-1-carboxylate (114.8 mg, 0.47 mmol) were dissolved in DMF, $K_2CO_3$ (184.4 mg, 1.33 mmol) was added to the solution and it was allowed to react at 80° C. for 4 h. Water was added to the reaction solution, the mixture was extracted twice with ethyl acetate and the resulting organic phases were combined, washed with water twice, washed with saturated saline, dried over anhydrous sodium sulfate, concentrated and purified by silica gel plate. The obtained product was dissolved in 5 ml of dichloromethane, 1 ml of trifluoroacetic acid was added and the reaction was carried out at room temperature for 1 h. After the reaction was completed, the reaction solution was concentrated. The obtained product was dissolved in 5 ml of dichloromethane, acetaldehyde (21.4 mg, 0.49 mmol) was added to the solution and the mixture was stirred at room temperature for half an hour. Sodium triacetylborohydride (186.5 mg, 0.88 mmol) was added and it was allowed to react at room temperature for 1 hour. After the reaction was completed, water was added to the reaction solution, the reaction solution was extracted twice with dichloromethane, and the resulting organic phases were combined, concentrated, purified on silica gel plate. The resulting product was dissolved in 5 ml of methanol, 5 mg of palladium carbon was added, the atmosphere was replaced with hydrogen, and the reaction was carried out at room temperature for 1 h. After the reaction was completed, the product was filtered and concentrated to afford 29 mg of Intermediate 31-1 with a yield of 39.5%.

$^1$H NMR (400 MHz, $CDCl_3$) δ 8.39 (s, 1H), 8.13 (s, 1H), 4.98-4.96 (m, 1H), 3.82-3.79 (m, 2H), 3.53-3.50 (m, 2H), 2.64-2.62 (m, 2H), 1.05 (t, J=8 Hz, 3H).

Synthesis of compound 31: (R)-5-(1-(3,5-dichloropyridin-4-yl)ethoxy)-N-(1-(1-ethyl-azetidin-3-yl)-1H-pyrazol-4-yl)-1H-indazole-3-carboxamide Intermediate 31-1 (13.7 mg, 0.08 mmol) and Intermediate 6-2 (30 mg, 0.07 mmol) were dissolved in DMF (3 ml), HATU (31.3 mg, 0.08 mmol) and DIPEA (17.7 mg, 0.14 mmol) were added, and the reaction was carried out at room temperature for 3 h. Water was added to the reaction solution, the mixture was extracted twice with ethyl acetate, and the resulting organic phases were combined, washed with saturated salt water, dried over anhydrous sodium sulfate, concentrated and purified by silica gel column. The resulting product was dissolved in 2 ml of methanol and 1 ml of concentrated hydrochloric acid, it was allowed to react at 50° C. for 2 h, and the reaction solution was concentrated. The concentrate was dissolved in 3 ml of methanol, 0.5 ml of ammonia was added, and the resulting solution was concentrated and purified by a preparative plate to afford 12 mg of the final product with a yield of 34.9%.

1H NMR (400 MHz, MeOD) δ 8.47 (s, 2H), 8.20 (s, 1H), 7.80 (s, 1H), 7.59 (s, 1H), 7.50 (d, J=8 Hz, 1H), 7.18 (d, J=8 Hz, 1H), 6.20-6.15 (m, 1H), 5.13-5.05 (m, 1H), 3.98-3.93 (m, 2H), 3.70-3.35 (m, 2H), 2.80-2.75 (m, 2H), 1.83 (d, J=8 Hz, 3H), 1.09 (t, J=8 Hz, 3H).

Examples 32-46 and Examples 47-51

Each compound shown in the table below was prepared via a synthetic route and method similar to that of Example 31 by varying the starting materials, and their $^1$H NMR and/or mass spectrometry data were measured.

| Examples | $^1$HNMR(400 MHz) | LC-MS Theoretical Calculated values (M + 1)$^+$ | LC-MS Measured values (M + 1)$^+$ |
|---|---|---|---|
| 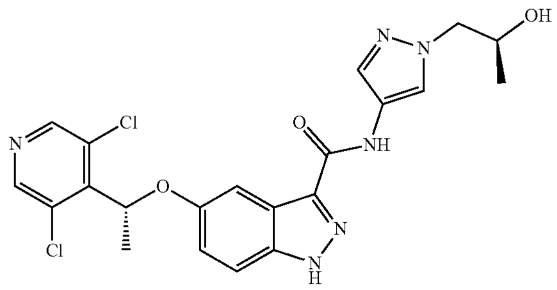<br>32<br>Example 32: 5-((R)-1-(3,5-dichloropyridin-4-yl)ethoxy)-N-(1-((S)-2-hydroxypropyl)-1H-pyrazol-4-yl)-1H-indazole-3-carboxamide | (MeOD) δ 8.48 (s, 2H), 8.10 (s, 1H), 7.73 (s, 1H), 7.59 (d, J = 4.0 Hz, 1H), 7.50 (d, J = 8.0 Hz, 1H), 7.22-7.15 (m, 1H), 6.18 (q, J = 4.0 Hz, 1H), 4.22-4.04 (m, 3H), 1.83 (d, J = 8.0 Hz, 3H), 1.20 (d, J = 4.0 Hz, 3H). | | |

-continued

| Examples | $^1$HNMR(400 MHz) | LC-MS Theoretical Calculated values (M + 1)$^+$ | LC-MS Measured values (M + 1)$^+$ |
|---|---|---|---|
| 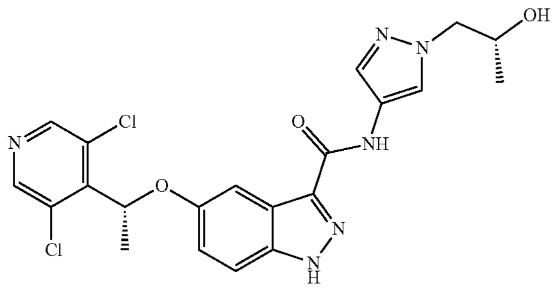 33 Example 33: 5-((R)-1-(3,5-dichloropyridin-4-yl)ethoxy)-N-(1-((R)-2-hydroxypropyl)-1H-pyrazol-4-yl)-1H-indazole-3-carboxamide | (MeOD) δ 8.47 (s, 2H), 8.10 (s, 1H), 7.73 (s, 1H), 7.59 (d, J = 4.0 Hz, 1H), 7.50 (d, J = 8.0 Hz, 1H), 7.20-7.16 (m, 1H), 6.18 (q, J = 8.0 Hz, 1H), 4.21-4.04 (m, 3H), 1.83 (d, J = 8.0 Hz, 3H), 1.20 (d, J = 4.0 Hz, 3H). | | |
| 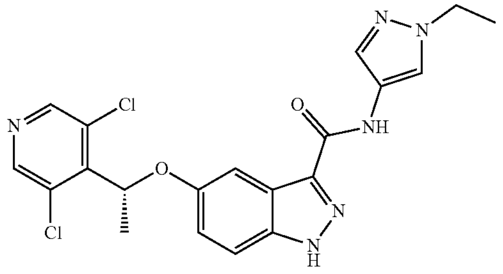 34 Example 34: (R)-5-(1-(3,5-dichloropyridin-4-yl)ethoxy)-N-(1-ethyl-1H-pyrazol-4-yl)-1H-indazole-3-carboxamide | (MeOD) δ 8.49 (s, 2H), 8.08 (s, 1H), 7.70 (s, 1H), 7.60 (d, J = 4 Hz, 1H), 7.50 (d, J = 8 Hz, 1H), 7.18 (dd, J = 8, 4 Hz, 1H), 6.20-6.17 (m, 1H), 4.24-4.18 (m, 2H), 1.83 (d, J = 4 Hz, 3H), 1.50 (t, J = 8 Hz, 3H). | | |
| 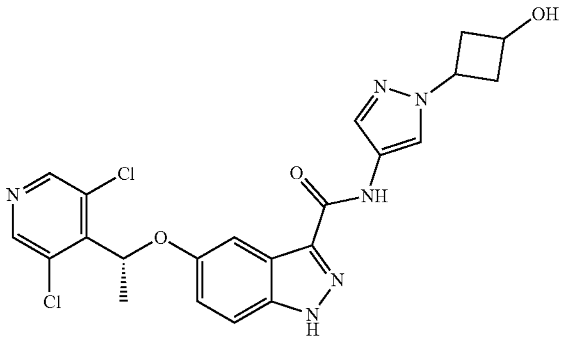 35 Example 35: (R)-5-(1-(3,5-dichloropyridin-4-yl)ethoxy)-N-(1-(3-hydroxycyclobutyl)-1H-pyrazol-4-yl)-1H-indazole-3-carboxamide | (DMSO)δ 13.63 (s, 1H), 10.42 (s, 1H), 8.60 (s, 2H), 8.06 (s, 1H), 7.70 (s, 1H), 7.63-7.49 (m, 2H), 7.21-7.11 (m, 1H), 6.15-6.03 (m, 1H), 5.21 (d, J = 4.0 Hz, 1H), 4.98-4.89 (m, 1H), 4.51-4.41 (m, 1H), 2.69-2.57 (m, 2H), 2.42-2.27 (m, 2H), 1.75 (d, J = 8.0 Hz, 3H). | | |

-continued

| Examples | $^1$HNMR(400 MHz) | LC-MS Theoretical Calculated values $(M + 1)^+$ | LC-MS Measured values $(M + 1)^+$ |
|---|---|---|---|
| 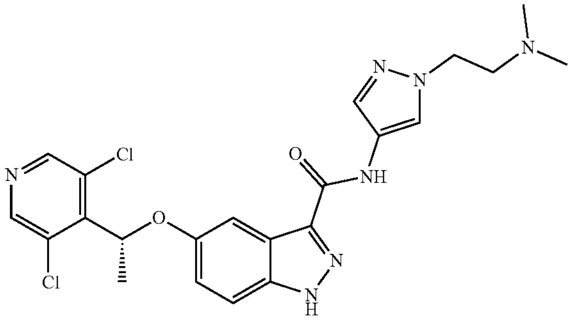 36 Example 36: (R)-5-(1-(3,5-dichloropyridin-4-yl)ethoxy)-N-(1-(2-(dimethylamino)ethyl)-1H-pyrazol-4-yl)-1H-indazole-3-carboxamide | (MeOD) δ 8.47 (s, 2H), 8.13 (s, 1H), 7.72 (s, 1H), 7.59 (d, J = 2.3 Hz, 1H), 7.51-7.48 (m, 1H), 7.17 (dd, J = 9.1 Hz, 2.4 Hz, 1H), 6.17 (q, J = 6.7 Hz, 1H), 4.30 (t, J = 6.8 Hz, 2H), 2.85 (t, J = 6.8 Hz, 2H), 2.32 (s, 6H), 1.82 (d, J = 6.6 Hz, 3H). | | |
| 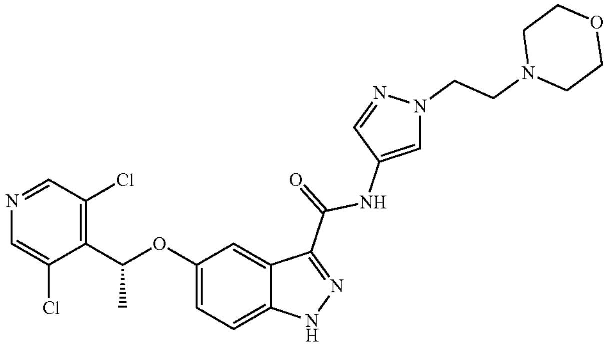 37 Example 37: (R)-5-(1-(3,5-dichloropyridin-4-yl)ethoxy)-N-(1-(2-morpholinoethyl)-1H-pyrazol-4-yl)-1H-indazole-3-carboxamide | (MeOD) δ 8.48 (s, 2H), 8.17 (s, 1H), 7.70 (s, 1H), 7.59 (d, J = 2.4 Hz, 1H), 7.50 (d, J = 8.8 Hz, 1H), 7.19 (dd, J = 2.4, 9.0 Hz, 1H), 6.18 (q, J = 6.7 Hz, 1H), 4.31 (t, J = 6.5 Hz, 2H), 3.73-3.71 (m, 4H), 2.85 (t, J = 6.5 Hz, 2H), 2.56-2.53 (m, 4H), 1.83 (d, J = 6.7 Hz, 3H). | | |
| 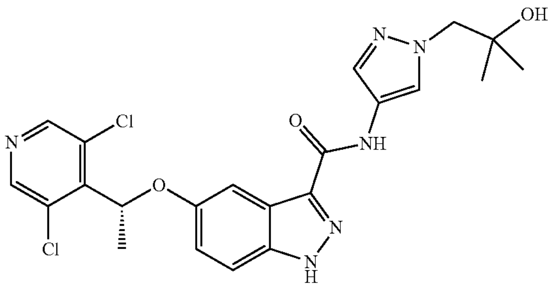 38 Example 38: (R)-5-(1-(3,5-dichloropyridin-4-yl)ethoxy)-N-(1-(2-hydroxy-2-methylpropyl)-1H-pyrazol-4-yl)-1H-indazole-3-carboxamide | (MeOD) δ 8.48 (s, 2H), 8.12 (s, 1H), 7.72 (s, 1H), 7.59 (d, J = 2.5 Hz, 1H), 7.51-7.49 (m, 1H), 7.18 (dd, J = 9.1 Hz, 2.4 Hz, 1H), 6.18 (q, J = 6.6 Hz, 1H), 4.12 (s, 2H), 1.83 (d, J = 6.6 Hz, 3H), 1.22 (s, 6H). | | |

-continued

| Examples | $^1$HNMR(400 MHz) | LC-MS Theoretical Calculated values (M + 1)$^+$ | LC-MS Measured values (M + 1)$^+$ |
|---|---|---|---|
| 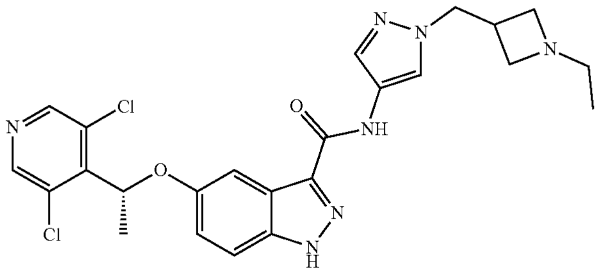 39 Example 39: (R)-5-(1-(3,5-dichloropyridin-4-yl)ethoxy)-N-(1-((1-ethyl-azetidin-3-yl)methyl)-1H-pyrazol-4-yl)-1H-indazole-3-carboxamide | (MeOD) δ 8.48 (s, 2H), 8.10 (s, 1H), 7.71 (s, 1H), 7.59 (d, J = 2.4 Hz,1H), 7.51-7.49 (m, 1H), 7.18 (dd, J = 9.1 Hz, 2.4 Hz, 1H), 6.18 (q, J = 6.7 Hz, 1H), 4.34 (d, J = 7.1 Hz, 2H), 3.52-3.48 (m, 2H), 3.16-3.12 (m, 2H), 3.09-3.00 (m, 1H), 2.57 (q, J = 7.2 Hz, 2H), 1.83 (d, J = 6.7 Hz, 3H), 1.00 (t, J = 7.2 Hz, 3H). | | |
| 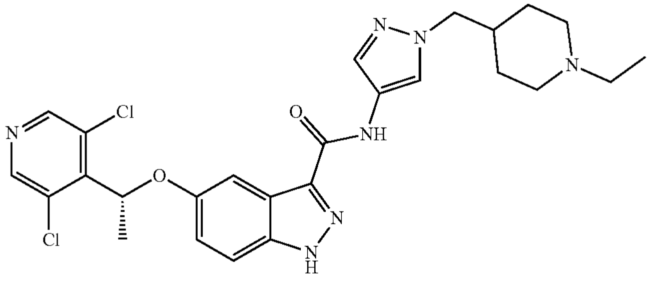 40 Example 40: (R)-5-(1-(3,5-dichloropyridin-4-yl)ethoxy)-N-(1-((1-ethylpiperidin-4-yl)methyl)-1H-pyrazol-4-yl)-1H-indazole-3-carboxamide | (MeOD) δ 8.48 (s, 2H), 8.08 (s, 1H), 7.72 (s, 1H), 7.60 (d, J = 2.3 Hz, 1H), 7.51-7.49 (m, 1H), 7.18 (dd, J = 9.1 Hz, 2.4 Hz, 1H), 6.18 (q, J = 6.7 Hz, 1H), 4.06 (d, J = 7.2 Hz, 2H), 3.04 (d, J = 11.7 Hz, 2H), 2.49 (q, J = 7.2 Hz, 2H), 2.07-1.94 (m, 3H), 1.83 (d, J = 6.7 Hz, 3H), 1.65 (d, J = 12.2 Hz, 2H), 1.44-1.34 (m, 2H), 1.13 (t, J = 7.2 Hz, 3H). | | |
| 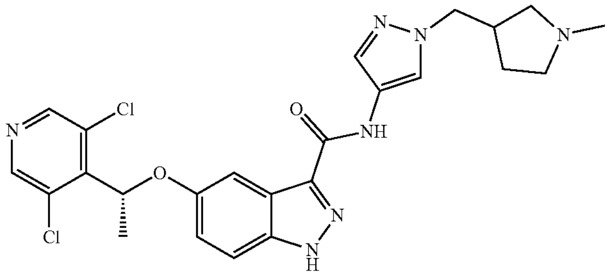 41 Example 41: 5-((R)-1-(3,5-dichloropyridin-4-yl)ethoxy)-N-(1-((1-methylpyrrolidin-3-yl)methyl)-1H-pyrazol-4-yl)-1H-indazole-3-carboxamide | | 514.1 | 514.1 |

-continued

| Examples | $^1$HNMR(400 MHz) | LC-MS Theoretical Calculated values (M + 1)$^+$ | LC-MS Measured values (M + 1)$^+$ |
|---|---|---|---|
| 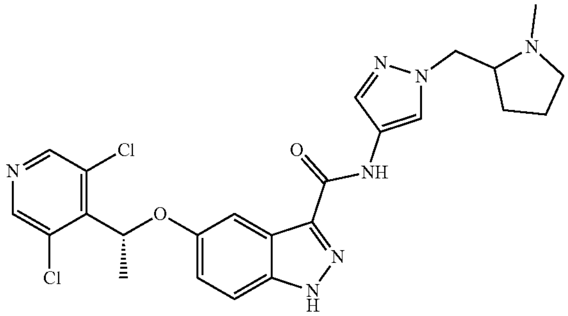 42 Example 42: 5-((R)-1-(3,5-dichloropyridin-4-yl)ethoxy)-N-(1-1((1-(methylpyrrolidin-2-yl)methyl)-1H-pyrazol-4-yl)-1H-indazole-3-carboxamide | | 514.1 | 514.1 |
| 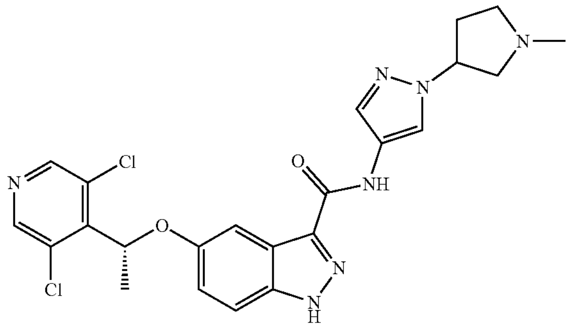 43 Example 43: 5-((R)-1-(3,5-dichloropyridin-4-yl)ethoxy)-N-(1-(1-methylpyrrolidin-3-yl)-1H-pyrazol-4-yl)-1H-indazole-3-carboxamide | | 500.1 | 500.1 |
| 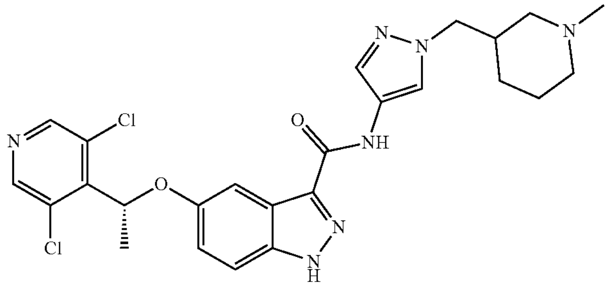 44 Example 44: 5-((R)-1-(3,5-dichloropyridin-4-yl)ethoxy)-N-(1-((1-methylpiperidin-3-yl)methyl)-1H-pyrazol-4-yl)-1H-indazole-3-carboxamide | | 528.1 | 528.1 |

-continued

| Examples | $^1$HNMR(400 MHz) | LC-MS Theoretical Calculated values $(M + 1)^+$ | LC-MS Measured values $(M + 1)^+$ |
|---|---|---|---|
| 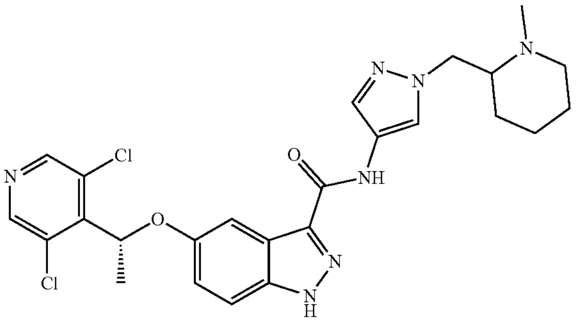<br>45<br>Example 45: 5-((R)-1-(3,5-dichloropyridin-4-yl)ethoxy)-N-(1-((1-methylpiperidin-2-yl)methyl)-1H-pyrazol-4-yl)-1H-indazole-3-carboxamide | | 528.1 | 528.1 |
| 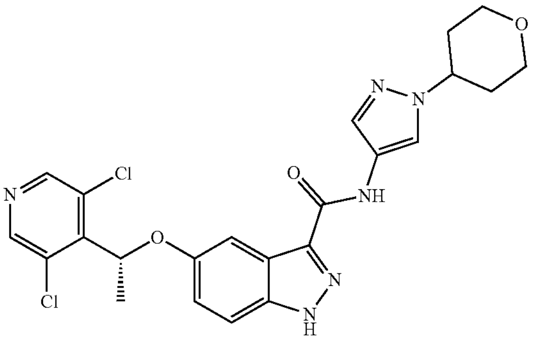<br>47<br>Example 47: (R)-5-(1-(3,5-dichloropyridin-4-yl)ethoxy)-N-(1-(tetrahydro-2H-pyran-4-yl)-1H-pyrazol-4-yl)-1H-indazole-3-carboxamide | (CDCl3)δ 10.56 (s, 1H), 8.74 (s, 1H), 8.44 (s, 2H), 8.17 (s, 1H), 7.79 (d, J = 2.0 Hz, 1H), 7.58 (s, 1H), 7.41 (d, J = 12.0 Hz, 1H), 7.19 (d, J = 10.0 Hz, 1H), 6.19-6.14 (m, 1H), 4.40-4.32 (m, 1H), 4.17-4.13 (m, 2H), 3.61-3.54 (m, 2H), 2.18-2.12 (m, 4H), 1.83 (d, J = 8.0 Hz, 3H). | | |
| 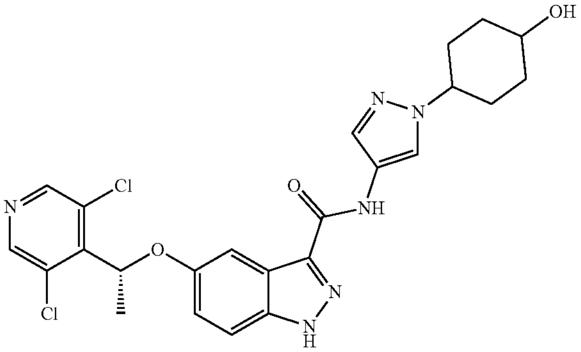<br>48<br>Example 48: (R)-5-(1-(3,5-dichloropyridin-4-yl)ethoxy)-N-(1-(4-hydroxycyclohexyl)-1H-pyrazol-4-yl)-1H-indazole-3-carboxamide | (MeOD) δ 8.48 (s, 2H), 8.09 (s, 1H), 7.70 (s, 1H), 7.59 (d, J = 2.4 Hz, 1H), 7.51-7.49 (m, 1H), 7.18 (dd, J = 9.1 Hz, 2.4 Hz, 1H), 6.18 (q, J = 6.7 Hz, 1H), 4.21-4.14 (m, 1H), 3.73-3.66 (m, 1H), 2.28-2.10 (m, 4H), 1.97-1.87 (m, 2H), 1.83 (d, J = 6.7 Hz, 3H), 1.55-1.46 (m, 2H). | | |

-continued

| Examples | $^1$HNMR(400 MHz) | LC-MS Theoretical Calculated values (M + 1)$^+$ | LC-MS Measured values (M + 1)$^+$ |
| --- | --- | --- | --- |
| 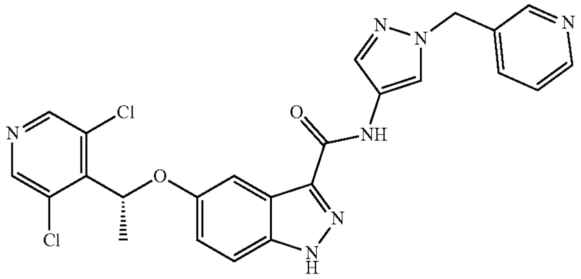<br>49<br>Example 49: (R)-5-(1-(3,5-dichloropyridin-4-yl)ethoxy)-N-(1-(pyridin-3-ylmethyl)-1H-pyrazol-4-yl)-1H-indazole-3-carboxamide | (MeOD) δ 8.53-8.50 (m, 2H), 8.47 (s, 2H), 8.24 (s, 1H), 7.78-7.76 (m, 2H), 7.58 (d, J = 2.4 Hz, 1H), 7.51-7.44 (m, 2H), 7.18 (dd, J = 9.1Hz, 2.4 Hz, 1H), 6.17 (q, J = 6.7 Hz, 1H), 5.44 (s, 2H), 1.83 (d, J = 6.6 Hz, 3H). | | |
| 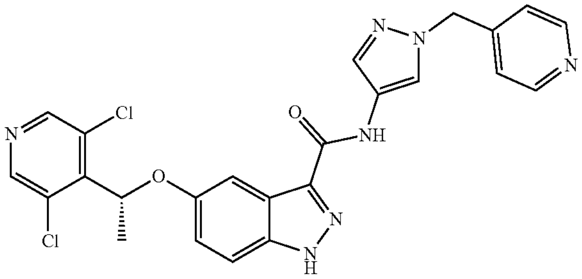<br>50<br>Example 50: (R)-5-(1-(3,5-dichloropyridin-4-yl)ethoxy)-N-(1-(pyridin-4-ylmethyl)-1H-pyrazol-4-yl)-1H-indazole-3-carboxamide | (MeOD) δ 8.53-8.52 (m, 2H), 8.47 (s, 2H), 8.26 (s, 1H), 7.80 (s, 1H), 7.59 (d, J = 2.5 Hz, 1H), 7.51-7.49 (m, 1H), 7.24 (d, J = 5.2 Hz, 2H), 7.18 (dd, J = 9.1 Hz, 2.5 Hz, 1H), 6.17 (q, J = 6.6 Hz, 1H), 5.47 (s, 2H), 1.83 (d, J = 6.5 Hz, 3H). | | |
| 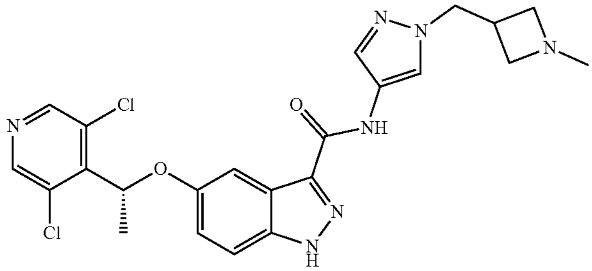<br>51<br>Example 51: (R)-5-(1-(3,5-dichloropyridin-4-yl)ethoxy)-N-(1-((1-methylazetidin-3-yl)methyl)-1H-pyrazol-4-yl)-1H-indazole-3-carboxamide | | 500.1 | 500.1 |

Example 46: 5-(1-3,5-dichloropyridin-4-yl)propoxy)-N-(1-methyl-1H-pyrazol-4-yl)-1H-indazole-3-carboxamide

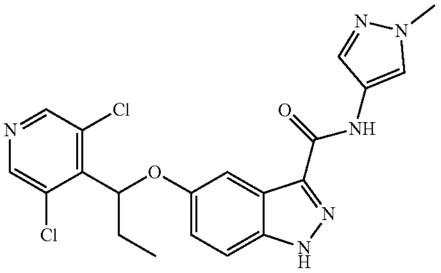

46

Synthetic Route of Compound 46:

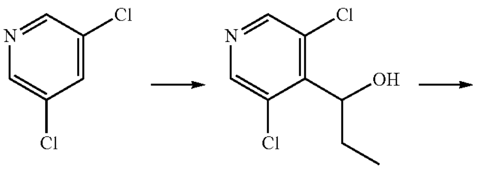

46-1

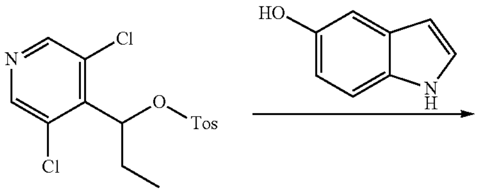

46-2

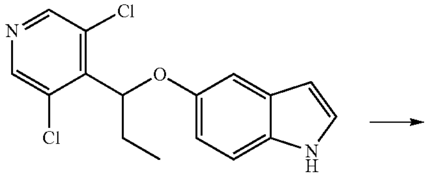

46-3

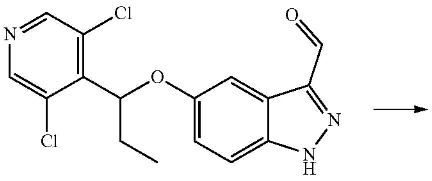

46-4

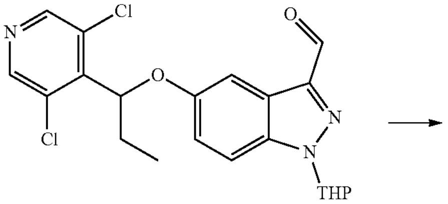

46-5

-continued

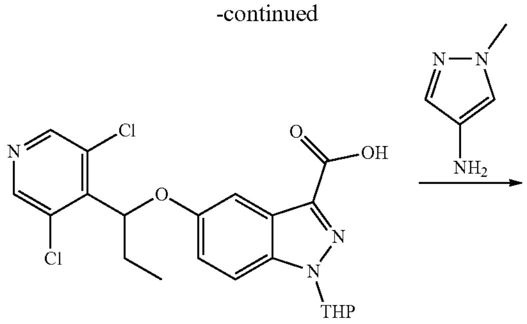

46-6

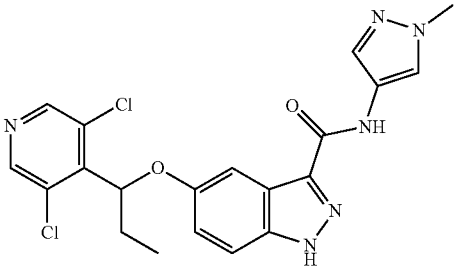

46

Synthesis Method:

Synthesis of Intermediate 46-1: 1-(3,5-dichloropyridin-4-yl)propan-1-ol

DIEA (6.35 g, 0.049 mol) was dissolved in 20 ml THF, the atmosphere was replaced with nitrogen, and the solution was cooled down to below −50° C. N-butyllithium (20 ml, 0.049 mol) was added dropwise and it was allowed to react for 10 min. The temperature was controlled in the range of −70° C. to −50° C. 3,5-Dichloropyridine (6.0 g, 0.041 mol) dissolved in THE was added dropwise and it was allowed to react for 20 min. Finally, anhydrous propionaldehyde (4.7 g, 0.082 mol) was added dropwise and the reaction was carried out at −50° C. for 2 h, then the reaction system was allowed to naturally return to room temperature and monitored by LCMS whether the reaction was completed. To the reaction solution, 30 ml of ammonium chloride solution was added, the mixture was extracted twice with ethyl acetate, and the resulting organic phases were combined, washed with saturated salt water, dried over anhydrous sodium sulfate, concentrated and purified by silica gel column to afford 7.8 g of intermediate 46-1 with a yield of 93.9%.

Synthesis of Intermediate 46-2: 1-(3,5-dichloropyridin-4-yl)propyl 4-methylbenzenesulfonate Intermediate 46-1 (7.8 g, 0.038 mol) and TEA (11.5 g, 0.114 mol) were dissolved in 20 ml DCM, and the reaction was cooled down to 0° C. p-Toluenesulfonyl chloride (8.7 g, 0.045 mol) and DMAP (0.48 g, 0.0038 mol) were added, and it was allowed to react at room temperature overnight. The reaction solution was quenched with water, and extracted twice with ethyl acetate, and the resulting organic phases were combined, washed with saturated salt water, dried over anhydrous sodium sulfate and concentrated to afford 10.3 g of crude Intermediate 46-2 with a yield of 75.7%.

Synthesis of Intermediate 46-3: 5-(1-(3,5-dichloropyridin-4-yl)propoxy)-1H-indole Intermediate 46-2 (10.3 g, 0.028 mol) and 5-hydroxyindole (4.6 g, 0.034 mol) were dissolved in 20 ml DMF, cesium carbonate (28.0 g, 0.086 mol) was added, and it was allowed to react at 60° C. for 2 h. Water was added to the reaction solution, the mixture was extracted twice with ethyl acetate, and the resulting organic phases were combined, washed with saturated salt water, dried over anhydrous sodium sulfate, concentrated and purified by silica gel column to give 4.51 g of intermediate 46-3 with a yield of 49.1%. LC-MS m/z (ESI) $[M+H]^+$ for $C_{15}H_{13}Cl_2N_3O$ was calculated as: 322.04; measured as: 322.04.

Synthesis of Intermediate 46-4: 5-(1-(3,5-dichloro-pyridin-4-yl)propoxy)-1H-indazole-3-carbaldehyde Sodium nitrite (8.1 g, 0.117 mol) was dissolved in 20 ml of water, 20 ml of DMF was added, and the reaction was cooled down to 0° C. 3M HCl (24 ml, 0.073 mol) was added dropwise, and then the cooling batch was removed after addition was completed. The mixture was stirred for 10 min at room temperature. Intermediate 46-3 (4.51 g, 0.015 mol) dissolved in 20 ml of DMF was added dropwise, and it was allowed to react for 3 h at room temperature. Water was added to the reaction solution, the mixture was extracted twice with ethyl acetate, and the resulting organic phases were combined, washed with saturated salt water, dried over anhydrous sodium sulfate, and concentrated to afford 4.63 g of crude intermediate 46-4 with a yield of 94.3%. LC-MS m/z (ESI) $[M+H]^+$ for $C_{15}H_{12}Cl_2N_4O_2$ was calculated as: 351.03; measured as: 351.03.

Synthesis of Intermediate 46-5: 5-(1-(3,5-dichloro-pyridin-4-yl)propoxy)-1-(tetrahydro-2H-pyran-2-yl)-1H-indazole-3-carbaldehyde 46-4 (4.63 g, 0.013 mol) was dissolved in 20 ml DCM, p-toluenesulfonic acid (2.26 g, 0.013 mol) was added, and the mixture was stirred for 2 min. 3,4-dihydro-2H-pyran (1.32 g, 0.015 mol) in DCM (5 ml) was added to the reaction solution and it was allowed to react for 2 h at room temperature. Water was added to the reaction solution, the mixture was extracted twice with DCM, and the resulting organic phases were combined, washed with saturated sodium bicarbonate solution and saturated salt water, dried over anhydrous sodium sulfate, concentrated and purified by silica gel column to give 2.61 g of Intermediate 46-5 with a yield of 45.6%. LC-MS m/z (ESI) LC-MS $[M+H]^+$ for $C_{20}H_{20}N_4O_3$ was calculated as: 435.09; measured as: 435.09.

Synthesis of Intermediate 46-6: 5-(1-(3,5-dichloro-pyridin-4-yl)propoxy)-1-(tetrahydro-2H-pyran-2-yl)-1H-indazole-3-carboxylic acid 46-5 (100.0 mg, 0.221 mmol) was dissolved in 24 ml of acetonitrile and 8 ml of water, potassium permanganate (87.1 mg, 0.442 mmol) was added and the reaction was carried out at room temperature for 16 hours. The reaction solution was filtered through diatomaceous earth and the filtrate was adjusted to pH 3 with 3M hydrochloric acid, and extracted twice with dichloromethane, and the resulting organic phases were combined, washed with saturated salt water, dried over anhydrous sodium sulfate, concentrated and purified by silica gel column to give 91 mg of Intermediate 46-6 with a yield of 88.1%. LC-MS m/z (ESI) $[M+H]^+$ for $C_{20}H_{20}N_4O_4$ was calculated as: 451.09; measured as: 451.09.

Synthesis of compound 46: 5-(1-(3,5-dichloropyridin-4-yl)propoxy)-N-(1-methyl-1H-pyrazol-4-yl)-1H-indazole-3-carboxamide Intermediate 46-6 (40.0 mg, 0.088 mmol) was dissolved in 5 ml DMF, HATU (40.5 mg, 0.11 mmol) and DIPEA (16.1 mg, 0.12 mmol) were added to the system and the mixture was stirred for one hour at room temperature. Then 1-methyl-1H-pyrazol-4-amine (8.6 mg. 0.088 mmol) was added to the system. After the addition was completed, it was allowed to react for 1 hour at room temperature. After the reaction was completed, the system was quenched with water, and extracted twice with ethyl acetate, and the resulting organic phases were combined, washed with saturated salt water, dried over anhydrous sodium sulfate, and concentrated. The obtained residue was dissolved in 4 ml of methanol, then 2 ml of concentrated hydrochloric acid was added and it was allowed to react at 50° C. After the reaction was completed, the reaction solution was evaporated under reduced pressure, and the residue was dissolved in 2 ml of methanol, and neutralized with 0.5 mmol of ammonia. After neutralization, the product was concentrate and purified by a preparative plate to afford 6.0 mg of the final product with a yield of 15.4%. LC-MS m/z (ESI) $[M+H]^+$ for $C_{20}H_{18}Cl_2N_6O_2$ was calculated as: 445.09; measured as: 445.09.

Assay I: Determination of Inhibitory Activity Against FGFR Mutants

1. Reagents and Equipment

| Materials and reagents | Manufacturer | Cat. No. |
|---|---|---|
| HTRF KinEASE-TK kit | Cisbio | 62TK0PEC |
| FGFR1 V561M | Signalchem | F04-13G |
| FGFR2 V564F | Signalchem | F05-12FG |
| VEGFR2 | Carna | 08-191 |
| FGFR3 V555M | Signalchem | F06-12GG |
| MgCl2 | Sigma | M1028 |
| ATP | Promega | V910B |
| DTT | Sigma | D0632 |
| DMSO | Sigma | D8418-1L |
| Infigratinib (NVP-BGJ398) | MCE | HY-13311 |
| Nintedanib | MCE | HY-50904 |

| Instruments and Equipment | Manufacturer | Cat. No. or Model No. |
|---|---|---|
| 384-well plate, white, low volume, round-bottom | Greiner | Sep. 20, 4046 |
| 96-well polypropylene plate | Nunc | Apr. 26, 2584 |
| Microplate low-speed centrifuge | Xiang Zhi | TD5B |
| Biotek Enzyme Labeler | Biotek | Synergy 4 |

2. Experimental Steps 2.1 Preparation of 1×Kinase Reaction Buffer:

1×Kinase reaction buffer was formulated with 1×volume of 5× kinase reaction buffer and 4×volume of water; 5 mM $MgCl_2$; and 1 mM DTT.

2.2 Reaction conditions

| Kinase | ATP Km[μM] | ATP working concentration [μM] | Substrate TK[μM] |
|---|---|---|---|
| FGFR1 V561M | 4.24 | 5 | 1 |
| FGFR2 V564F | 13.81 | 10 | 1 |
| FGFR3 K650E | 45.58 | 50 | 1 |
| FGFR3 V555M | 18.02 | 20 | 1 |
| VEGFR2 | 5.92 | 5 | 1 |

2.3 Screening of Compounds:

1. Diluting a compound 4-fold in a dilution plate with DMSO, with a starting compound concentration of 2 mM (4 mM for Nentedanib).
2. Diluting the compound 40-fold into 1× kinase reaction buffer and shaking it on a shaker for 20 minutes.
3. Formulating 2×FGFR1 V561M/FGFR2 V564F/FGFR3 K650E/VEGFR2 with 1× of enzyme reaction buffer.
4. Adding 2 μl FGFR1 V561M/FGFR2 V564F/FGFR3 K650E/VEGFR2 kinase (formulated in step 3) to each well of the reaction plate.
5. Adding 1 μl of the compound diluted in buffer to each well, sealing the plate with a sealing membrane and centrifuging the plate at 1000 g for 30 seconds and leaving it at room temperature for 10 minutes.
6. Formulating 2.5×TK-substrate-biotin and ATP mixture with 1× enzyme reaction buffer and adding 2 μl of K-substrate-biotin/ATP mixture to the reaction plate.

le;.3q7. Sealing the plate with a sealing membrane and centrifuging the plate at 1000 g for 30 seconds and allowing it to react at room temperature for 50 minutes.

8. Formulating 4×Sa-XL 665 (250 nM) with HTRF assay buffer.
9. Adding 5 μl Sa-XL 665 and 5 μl TK-Antibody-Cryptate to each well, centrifuging it at 1000 g for 30 seconds, and allowing it to react for 1 hour at room temperature.
10. Reading fluorescence signals at 615 nm (Cryptate) and 665 nm (XL665) with Biotek.

3. Data Analysis 3.1 Calculation of the ratio for each well: the ratio was calculated as 665/615 nm.

3.2 The inhibition rate was calculated as follows: inhibition rate of compound (% inh)=100%−(compound−positive control)/(negative control−positive control)*100%. The positive control was 20,000 nM Nintedanib or Infigratinib, and the negative control was 0.5% DMSO.

3.3 Calculation of IC50 and plotting of inhibition curves for the compounds.

The IC50 (half inhibition concentration) of a compound was obtained using the following non-linear fitting equation, wherein data analysis was performed using Graphpad 6.0 software.

$$Y=\text{Bottom}+(\text{Top}-\text{Bottom})/(1+10\hat{}((\text{Log IC50}-X)*\text{Hill Slope}))$$

X: log value of compound concentration; and Y: inhibition rate (% inh)

3.4 Validation of Results

Data were exported from Envision and analyzed manually. The ratios were converted to inhibition rates and IC50 was calculated by Prism GraphPad 6.0 from the inhibition rates. IC50 was calculated again by the ratios to verify accuracy of the results.

3.5 Quality Control

Z-factor>0.5; and S/B>2

Positive control IC50 was within 3 times of the average value

4. Results

TABLE 1

Inhibition of FGFR mutants by compounds of Examples 1-22

| Compounds | IC$_{50}$ (nM) FGFR1 V561M | FGFR2 V564F | FGFR3 K650E | FGFR3 V555M | VEGFR2 |
|---|---|---|---|---|---|
| Infigratinib | 26.6 | 691 | Not measured | 129 | Not measured |

TABLE 1-continued

Inhibition of FGFR mutants by compounds of Examples 1-22

| Compounds | IC$_{50}$ (nM) FGFR1 V561M | FGFR2 V564F | FGFR3 K650E | FGFR3 V555M | VEGFR2 |
|---|---|---|---|---|---|
| Nintedanib | 166.4 | 19.4 | 16.7 | Not measured | 1.8 |
| 1 | 6.3 | 2.3 | 26.8 | 8.6 | Not measured |
| 2 | 7.0 | 2.0 | 30 | 2.2 | 176 |
| 3 | 69.7 | 22.1 | Not measured | Not measured | >10000 |
| 4 | 95.1 | 9.5 | Not measured | Not measured | 1586 |
| 5 | 7.2 | 2.4 | 33.4 | 4.6 | Not measured |
| 6 | 2.3 | 0.66 | Not measured | 0.94 | 84.1 |
| 7 | 5.2 | 0.42 | Not measured | 0.73 | 97.6 |
| 8 | 2.3 | 4.0 | Not measured | 2.6 | 224 |
| 9 | 1.0 | 0.94 | Not measured | 1.1 | 152 |
| 10 | 1.7 | 3.2 | Not measured | 2.0 | 1387 |
| 11 | 5.6 | 1.1 | Not measured | 1.7 | 230 |
| 12 | 1.9 | 0.48 | Not measured | 0.74 | 208 |
| 13 | 6.8 | 8.9 | Not measured | 5.9 | >10000 |
| 14 | 0.47 | 0.14 | Not measured | 0.27 | 24.7 |
| 15 | 2.2 | 0.84 | Not measured | 2.1 | 66.2 |
| 16 | 22.8 | 34.1 | Not measured | 41.7 | 1209 |
| 17 | 8.6 | 2.3 | Not measured | 6.9 | 173 |
| 18 | 1.6 | 0.63 | Not measured | 1.1 | 141 |
| 19 | 0.35 | 0.24 | Not measured | 0.27 | 63.4 |
| 20 | 9.1 | 0.82 | Not measured | 0.88 | 327 |
| 21 | 0.27 | 0.09 | Not measured | 0.15 | 39.4 |
| 22 | 0.91 | 0.6 | Not measured | 0.79 | 179 |

Each example compound being tested above showed good inhibitory activity against FGFR1 V561M/FGFR2 V564F/FGFR3 V555M, while exhibiting relatively weak inhibitory activity against VEGFR2.

Assay II: Determination of inhibitory activity against wild-type FGFR

1. Reagents and Equipment

| Materials and reagents | Manufacturer | Cat. No. |
|---|---|---|
| HTRF KinEASE-TK kit | Cisbio | 62TK0PEC |
| FGFR1 | Carna | 08-133 |
| FGFR2 | Carna | 08-134 |
| FGFR3 | Carna | 08-135 |
| MgCl2 | Sigma | M1028 |
| ATP | Promega | V910B |

-continued

| | | |
|---|---|---|
| DTT | Sigma | D0632 |
| DMSO | Sigma | D8418-1L |
| Nintedanib | MCE | HY-50904 |

| Instruments and Equipment | Manufacturer | Cat. No. or Model No. |
|---|---|---|
| 384-well plate, white, low volume, round-bottom | Greiner | Sep. 20, 4046 |
| 96-well polypropylene plate | Nunc | Apr. 26, 2584 |
| Microplate low-speed centrifuge | Xiang Zhi | TD5B |
| Biotek Enzyme Labeler | Biotek | Synergy 4 |

2. Experimental Steps 2.1 Preparation of 1×Kinase Reaction Buffer:

1×Kinase reaction buffer was formulated with 1×volume of 5× kinase reaction buffer and 4×volume of water; 5 mM $MgCl_2$; and 1 mM DTT.

| 2.2 Reaction conditions | | | |
|---|---|---|---|
| Kinase | ATP Km[μM] | ATP working concentration [μM] | Substrate TK[μM] |
| FGFR1 | 28.3 | 50 | 1 |
| FGFR2 | 36.47 | 50 | 1 |
| FGFR3 | 67.28 | 50 | 1 |

2.3 Screening of Compounds:

1. Diluting a compound 4-fold in a dilution plate with DMSO, with a starting compound concentration of 2 mM (4 mM for Nentedanib).

2. Diluting the compound 40-fold into 1× kinase reaction buffer and shaking it on a shaker for 20 minutes.

3. Formulating 2×FGFR1/FGFR2/FGFR3 with 1× of enzyme reaction buffer.

4. Adding 2 μl FGFR1/FGFR2/FGFR3 kinase (formulated in step 3) to each well of the reaction plate.

5. Adding 1 μl of the compound diluted in buffer to each well, sealing the plate with a sealing membrane and centrifuging the plate at 1000 g for 30 seconds and leaving it at room temperature for 10 minutes.

6. Formulating 2.5×TK-substrate-biotin and ATP mixture with 1× enzyme reaction buffer and adding 2 μl of K-substrate-biotin/ATP mixture to the reaction plate.

7. Sealing the plate with a sealing membrane and centrifuging the plate at 1000 g for 30 seconds and allowing it to react at room temperature for 50 minutes.

8. Formulating 4×Sa-XL 665 (250 nM) with HTRF assay buffer.

9. Adding 5 μl Sa-XL 665 and 5 μl TK-Antibody-Cryptate to each well, centrifuging it at 1000 g for 30 seconds, and allowing it to react for 1 hour at room temperature.

10. Reading fluorescence signals at 615 nm (Cryptate) and 665 nm (XL665) with Biotek.

3. Data Analysis 3.1 Calculation of the ratio for each well: the ratio was calculated as 665/615 nm.

3.2 The inhibition rate was calculated as follows: inhibition rate of compound (% inh)=100%−(compound−positive control)/(negative control−positive control)*100%. The positive control was 20,000 nM Nintedanib, and the negative control was 0.5% DMSO.

3.3 Calculation of IC50 and plotting of inhibition curves for the compounds.

The IC50 (half inhibition concentration) of a compound was obtained using the following non-linear fitting equation, wherein data analysis was performed using Graphpad 6.0 software.

$$Y\text{=Bottom+(Top−Bottom)/(1+10^((Log IC50−}X\text{)*Hill Slope))}$$

X: log value of compound concentration; and Y: inhibition rate (% inh)

3.4 Validation of Results

Data were exported from Envision and analyzed manually. The ratios were converted to inhibition rates and IC50 was calculated by Prism GraphPad 6.0 from the inhibition rates. IC50 was calculated again by the ratios to verify accuracy of the results.

3.5 Quality Control

Z-factor>0.5; and S/B>2

Positive control IC50 was within 3 times of the average value

4. Results

TABLE 2

| Inhibition of wild FGFR by compounds | | | |
|---|---|---|---|
| | $IC_{50}$ (nM) | | |
| Compounds | FGFR1 | FGFR2 | FGFR3 |
| Nintedanib | 35.2 | 55.9 | 130.6 |
| 6 | 27.7 | 21.3 | 52.2 |
| 7 | 27.5 | 7.6 | 42.6 |
| 8 | 69.7 | 58.6 | 106 |
| 9 | 61.0 | 48.7 | 102 |
| 10 | 64.5 | 48 | 98.8 |
| 12 | 45.1 | 24.5 | 42.9 |
| 14 | 11.1 | 9.5 | 19.2 |

Each example compound being tested above showed similar or better inhibitory activity against wild-type FGFR1/FGFR2/FGFR3 compared with Nintedanib.

Assay III: Determination of Inhibitory Activity Against FGFR Mutants

The inhibitory activities of the compounds of examples 23-50 and the control compound Infigratinib against various FGFR mutants were measured using the same test method and equipment as described in "Assay I: Determination of Inhibitory Activity against FGFR Mutants", but by a different experimental operator, and the results are shown in Table 3 below.

TABLE 3

| Inhibition of FGFR mutants by compounds of Examples 23-50 | | | | |
|---|---|---|---|---|
| | $IC_{50}$ (nM) | | | |
| Compounds | FGFR1 V561M | FGFR2 V564F | FGFR3 V555M | VEGFR2 |
| Infigratinib | 67.5 | 1128 | 69.6 | 73 |
| 23 | 2.2 | 0.47 | 0.92 | 114 |
| 24 | 3.3 | 0.43 | 1.3 | 201 |
| 25 | 3.6 | 0.26 | 0.21 | 145 |
| 26 | 11.4 | 1.8 | 2.9 | 255 |
| 27 | 20 | 2.1 | 7.3 | 581 |
| 28 | 11 | 2.6 | 3.0 | 68 |
| 29 | 2.3 | 0.93 | 0.25 | 144 |
| 30 | 36 | 3.7 | 7.6 | 729 |
| 31 | 0.93 | 0.11 | 0.07 | 54 |
| 32 | 0.3 | 0.37 | 0.26 | 86 |
| 33 | 1.0 | 0.33 | 0.39 | 99 |
| 34 | 0.24 | 0.06 | 0.75 | 61 |

TABLE 3-continued

Inhibition of FGFR mutants by compounds of Examples 23-50

| | $IC_{50}$ (nM) | | | |
|---|---|---|---|---|
| Compounds | FGFR1 V561M | FGFR2 V564F | FGFR3 V555M | VEGFR2 |
| 35 | 0.29 | 0.16 | 0.27 | 89 |
| 36 | 0.88 | 0.07 | 0.11 | 41 |
| 37 | 1.6 | 0.44 | 0.16 | 79 |
| 38 | 3.7 | 0.40 | 0.59 | 61 |
| 39 | 0.35 | 0.05 | 0.05 | 30 |
| 40 | 0.42 | 1.3 | 0.02 | 33 |
| 41 | 0.37 | 0.18 | 0.22 | 84 |
| 42 | 1.1 | 0.43 | 0.44 | 169 |
| 43 | 0.38 | 0.15 | 0.14 | 62 |
| 44 | 1.1 | 0.39 | 0.55 | 145 |
| 45 | 0.34 | 0.10 | 0.14 | 62 |
| 46 | 3.4 | 1.0 | 2.1 | 184 |
| 47 | 2.3 | 1.2 | 2.1 | 194 |
| 48 | 1.0 | 0.31 | 0.82 | 115 |
| 49 | 0.51 | 0.55 | 1.4 | 110 |
| 50 | 1.7 | 0.37 | 0.64 | 152 |

It can be seen from the above table that each example compound being tested showed good inhibitory activity against FGFR1 V561M/FGFR2 V564F/FGFR3 V555M, while exhibiting relatively weak inhibitory activity against VEGFR2.

Although specific embodiments of the present disclosure have been illustrated and described, it does not mean that these embodiments illustrate and describe all possible implementation forms of the present disclosure. More precisely, the language used in this specification are only descriptive words and not restrictive. It will be obvious to those skilled in the art that various kinds of changes and modifications can be made without departing from the general scope of the present disclosure. Therefore, the appended claims are intended to include all these changes and modifications within the scope of the present disclosure.

What is claimed is:

1. A compound or an optical isomer thereof, a geometric isomer thereof, a tautomer thereof, or a pharmaceutically acceptable salt thereof, which is a compound selected from formula (II), formula (III), formula (IV) and formula (V), or an optical isomer thereof, a geometric isomer thereof, a tautomer thereof, or a pharmaceutically acceptable salt thereof (II)

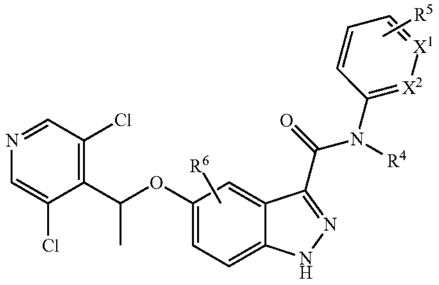

-continued (III)

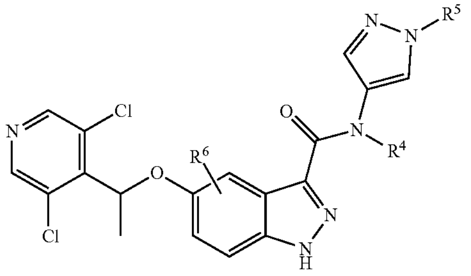

(IV)

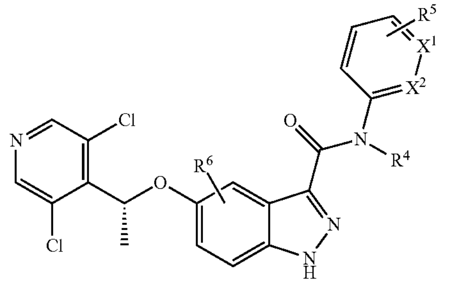

(V)

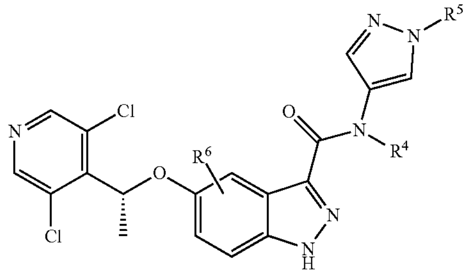

wherein $R^4$ is H;

0 to 8 $R^5$(s) are present, and each $R^5$ is independently selected from the group consisting of H, halogen, —OH, —$NO_2$, —CN, —$SF_5$, —SH, —S—$C_{1-4}$ alkyl, $C_{1-6}$ alkyl, $C_{1-6}$ haloalkyl, $C_{1-6}$ alkoxy, $C_{1-6}$ haloalkoxy, $C_{2-8}$ alkenyl, $C_{2-8}$ alkynyl, $C_{3-7}$ cycloalkyl, 3-10 membered heterocycloalkyl, $C_{6-12}$ bicycloalkyl, 6-12 membered bicycloheteroalkyl, $C_{8-15}$ tricycloalkyl, 8-15 membered tricycloheteroalkyl, $C_{5-8}$ aryl, 5-7 membered heteroaryl, $C_{7-11}$ bicycloaryl, 7-11 membered bicycloheteroaryl, —$C_{1-4}$ alkyl-($C_{3-7}$ cycloalkyl), —$C_{1-4}$ alkyl-(3-10 membered heterocycloalkyl), —$C_{1-4}$ alkyl-($C_{6-12}$ bicycloalkyl), —$C_{1-4}$ alkyl-(6-12 membered bicycloheteroalkyl), —$C_{1-4}$ alkyl-($C_{8-15}$-tricycloalkyl), —$C_{1-4}$ alkyl-(8-15 membered tricycloheteroalkyl), —N($R^7$)($R^8$), —N($R^7$)(C(═O) $R^8$), —N($R^7$)(C(═O)—O$R^8$), —N($R^7$)(C(═O)—N($R^8$)($R^9$), —C(═O)—N($R^7$)($R^8$), —C(═O)—$R^7$, —C(═O)—O$R^7$, —OC(═O) $R^7$, —N($R^7$)(S(═O)$_2R^8$), —S(═O)$_2$—N($R^7$)($R^8$), —S$R^7$, and —O$R^7$, wherein the —S—$C_{1-4}$ alkyl, $C_{1-6}$ alkyl, $C_{1-6}$ alkoxy, $C_{1-6}$ haloalkoxy, $C_{2-8}$ alkenyl, $C_{2-8}$ alkynyl, $C_{3-7}$ cycloalkyl, 3-10 membered heterocycloalkyl, $C_{6-12}$ bicycloalkyl, 6-12 membered bicycloheteroalkyl, $C_{8-15}$ tricycloalkyl, 8-15 membered tricycloheteroalkyl, $C_{5-8}$ aryl, 5-7 membered heteroaryl, $C_{7-11}$ bicycloaryl, 7-11 membered bicycloheteroaryl, —$C_{1-4}$ alkyl-($C_{3-7}$ cycloalkyl), —$C_{1-4}$ alkyl-(3-10 membered heterocycloalkyl), —$C_{1-4}$ alkyl-($C_{6-12}$ bicycloalkyl), —$C_{1-4}$ alkyl-(6-12 membered bicycloheteroalkyl), —$C_{1-4}$ alkyl-($C_{8-15}$ tricycloalkyl), and —$C_{1-4}$ alkyl-(8-15 membered tricycloheteroalkyl) are each optionally substituted with 0 to 4 $R^{5a}$(s);

each $R^{5a}$ is independently selected from the group consisting of H, halogen, —OH, —$NO_2$, —CN, —$SF_5$, —SH, —S—$C_{1-4}$ alkyl, $C_{1-6}$ alkyl, $C_{1-6}$ haloalkyl, $C_{1-6}$ alkoxy, $C_{1-6}$ haloalkoxy, $C_{2-8}$ alkenyl, $C_{2-8}$ alkynyl, $C_{3-7}$ cycloalkyl, 3-10 membered heterocycloalkyl, $C_{6-12}$ bicycloalkyl, 6-12 membered bicycloheteroalkyl, $C_{8-15}$ tricycloalkyl, 8-15 membered tricycloheteroalkyl, $C_{5-8}$ aryl, 5-7 membered heteroaryl, $C_{7-11}$ bicycloaryl, 7-11 membered bicycloheteroaryl, —$C_{1-4}$ alkyl-($C_{3-7}$ cycloalkyl), —$C_{1-4}$ alkyl-(3-10 membered heterocycloalkyl), —$C_{1-4}$ alkyl-($C_{6-12}$ bicycloalkyl), —$C_{1-4}$ alkyl-(6-12 membered bicycloheteroalkyl), —N($R^7$)($R^8$), —N($R^7$)(C(═O) $R^8$), —N($R^7$)(C(═O)—O$R^8$), —N($R^7$)(C(═O)—N($R^8$)($R^9$), —C(═O)—N($R^7$)($R^8$), —C(═O)—$R^7$, —C(═O)—O$R^7$, —OC(═O) $R^7$—N($R^7$)(S(═O)$_2R^8$), —S(═O)$_2$—N($R^7$)($R^8$), —S$R^7$, and —O$R^7$, wherein the —S—$C_{1-4}$ alkyl, $C_{1-6}$ alkyl, $C_{1-6}$ haloalkyl, $C_{1-6}$ alkoxy, $C_{1-6}$ haloalkoxy, $C_{2-8}$ alkenyl, $C_{2-8}$ alkynyl, $C_{3-7}$ cycloalkyl, 3-10 membered heterocycloalkyl, $C_{6-12}$ bicycloalkyl, 6-12 membered bicycloheteroalkyl, $C_{8-15}$ tricycloalkyl, 8-15 membered tricycloheteroalkyl, $C_{5-8}$ aryl, 5-7 membered heteroaryl, $C_{7-11}$ bicycloaryl, 7-11 membered bicycloheteroaryl, —$C_{1-4}$ alkyl-($C_{3-7}$ cycloalkyl), —$C_{1-4}$ alkyl-(3-10 membered heterocycloalkyl), —$C_{1-4}$ alkyl-($C_{6-12}$ bicycloalkyl) and —$C_{1-4}$ alkyl-(6-12 membered bicycloheteroalkyl) are each optionally substituted with 0 to 4 $R^{5b}$;

each $R^{5b}$ is independently selected from the group consisting of H, halogen, —OH, —CN, —$NO_2$, $SF_5$, —SH, —S—$C_{1-4}$ alkyl, oxo, $C_{1-6}$ alkyl, $C_{1-6}$ haloalkyl, $C_{1-6}$ alkoxy, $C_{1-6}$ haloalkoxy, $C_{3-7}$ cycloalkyl, 3-10 membered heterocycloalkyl, $C_{6-10}$ aryl, 5-10 membered heteroaryl, —$C_{1-4}$ alkyl-($C_{3-7}$ cycloalkyl), —$C_{1-4}$ alkyl-(3-10 membered heterocycloalkyl), —N($R^7$)($R^8$), —N($R^7$)(C(═O) $R^8$), —N($R^7$)(C(═O)—O$R^8$), —N($R^7$)(C(═O)—N($R^8$)($R^9$)), —C(═O)—N($R^7$)($R^8$), —C(═O)—$R^7$, —C(═O)—O$R^7$, —OC(═O) $R^7$, —N($R^7$)(S(═O)$_2R^8$), and —S(═O)$_2$—N($R^7$)($R^8$), wherein the —S—$C_{1-4}$ alkyl, $C_{1-6}$ alkyl, $C_{1-6}$ haloalkyl, $C_{1-6}$ alkoxy, $C_{1-6}$ haloalkoxy, $C_{3-7}$ cycloalkyl, 3-10 membered heterocycloalkyl, $C_{6-10}$ aryl, 5-10 membered heteroaryl, —$C_{1-4}$ alkyl-($C_{3-7}$ cycloalkyl), and —$C_{1-4}$ alkyl-(3-10 membered heterocycloalkyl) are each optionally substituted with 0 to 4 substitutes each independently selected from the group consisting of halogen, —OH, —$NH_2$, —NH($CH_3$), —N($CH_3$)$_2$, —CN, —$NO_2$, —$SF_5$, —SH, —S—$C_{1-4}$ alkyl, oxo, $C_{1-4}$ alkyl, $C_{2-6}$ alkenyl, $C_{2-6}$ alkynyl, $C_{3-7}$ cycloalkyl, $C_{1-4}$ hydroxyalkyl, —S—$C_{1-4}$ alkyl, —C(═O) H, —C(═O)—$C_{1-4}$ alkyl, —C(═O)—O—$C_{1-4}$ alkyl, —C(═O)—$NH_2$, —C(═O)—N($C_{1-4}$ alkyl)$_2$, $C_{1-4}$ haloalkyl, $C_{1-4}$ alkoxy and $C_{1-4}$ haloalkoxy; and 0 to 3 $R^6$(s) are present, and each $R^6$ is independently selected from the group consisting of H, halogen, —CN, —$NO_2$, $C_{1-3}$ alkyl, $C_{1-3}$ haloalkyl, $C_{1-3}$ alkoxy, $C_{3-6}$ cycloalkyl, and 4-6 membered heterocycloalkyl; and $X_1$ and $X_2$ are each independently selected from the group consisting of —CH N and C in case of being directly connected with $R^5$.

2. The compound according to claim 1 or an optical isomer thereof, a geometric isomer thereof, a tautomer thereof, or a pharmaceutically acceptable salt thereof, wherein $R^6$ is H.

3. The compound according to claim 1 or an optical isomer thereof, a geometric isomer thereof, a tautomer thereof, or a pharmaceutically acceptable salt thereof, or a prodrug thereof, wherein $R^5$ is selected from halogen, $C_{1-6}$ alkyl, $C_{3-7}$ cycloalkyl, and 3-10 membered heterocycloalkyl, wherein the $C_{1-6}$ alkyl, $C_{3-7}$ cycloalkyl, and 3-10 membered heterocycloalkyl are each optionally substituted with 0 to 4 substituents each independently selected from the group consisting of: halogen, —CN, —OH, $C_{1-4}$ alkyl, $C_{3-6}$ cycloalkyl.

4. The compound according to claim 1 or an optical isomer thereof, a geometric isomer thereof, a tautomer thereof, or a pharmaceutically acceptable salt thereof, wherein H is optionally replaced by D at each occurrence.

5. The compound according to claim 1 or an optical isomer thereof, a geometric isomer thereof, a tautomer thereof, or a pharmaceutically acceptable salt thereof, wherein the compound is selected from:

5-(1-(3,5-dichloropyridin-4-yl)ethoxy)-N-(4-((3S,5R)-3,5-dimethylpiperazin-1-yl)phenyl)-1H-indazole-3-carboxamide, 5-(1-(3,5-dichloropyridin-4-yl)ethoxy)-N-(1-(2-hydroxyethyl)-1H-pyrazol-4-yl)-1H-indazole-3-carboxamide, 5-(1-(3,5-dichloropyridin-4-yl)ethoxy)-N-(4-((R)-3-hydroxypyrrolidin-1-yl)phenyl)-1H-indazole-3-carboxamide, 5-(1-(3,5-dichloropyridin-4-yl)ethoxy)-N-(6-morpholinopyridin-3-yl)-1H-indazole-3-carboxamide, N-(1-(1-cyanopropan-2-yl)-1H-pyrazol-4-yl)-5-(1-(3,5-dichloropyridin-4-yl)ethoxy)-1H-indazole-3-carboxamide, 5-((R)-1-(3,5-dichloropyridin-4-yl)ethoxy)-N-(4-((3S,5R)-3,5-dimethylpiperazin-1-yl)phenyl)-1H-indazole-3-carboxamide, (R)-5-(1-(3,5-dichloropyridin-4-yl)ethoxy)-N-(1-(2-hydroxyethyl)-1H-pyrazol-4-yl)-1H-indazole-3-carboxamide, 5-(1-(3,5-dichloropyridin-4-yl)ethoxy)-N-(6-((3S,5R)-3,5-dimethylpiperazin-1-yl) pyridin-3-yl)-1H-indazole-3-carboxamide, 5-(1-(3,5-dichloropyridin-4-yl)ethoxy)-N-(4-(4-methylpiperazin-1-yl)phenyl)-1H-indazole-3-carboxamide, 5-(1-(3,5-dichloropyridin-4-yl)ethoxy)-N-(4-(4-ethylpiperazin-1-yl)phenyl)-1H-indazole-3-carboxamide, N-(1-(2-cyanoethyl)-1H-pyrazol-4-yl)-5-(1-(3,5-dichloropyridin-4-yl)ethoxy)-1H-indazole-3-carboxamide, 5-(1-(3,5-dichloropyridin-4-yl)ethoxy)-N-(1-(3-hydroxycyclobutyl)-1H-pyrazol-4-yl)-1H-indazole-3-carboxamide, 5-(1-(3,5-dichloropyridin-4-yl)ethoxy)-N-(4-(4-hydroxypiperidin-1-yl)phenyl)-1H-indazole-3-carboxamide, 5-(1-(3,5-dichloropyridin-4-yl)ethoxy)-N-(1-(1-methylpiperidin-4-yl)-1H-pyrazol-4-yl)-1H-indazole-3-carboxamide, 5-(1-(3,5-dichloropyridin-4-yl)ethoxy)-N-(1-(2-(1-hydroxycyclopropyl)ethyl)-1H-pyrazol-4-yl)-1H-indazole-3-carboxamide, 5-(1-(3,5-dichloropyridin-4-yl)ethoxy)-N-(5-((3S,5R)-3,5-dimethylpiperazin-1-yl) pyridin-2-yl)-1H-indazole-3-carboxamide, 5-(1-(3, 5-dichloropyridin-4-yl)ethoxy)-N-(4-((3S, 5R)-3,5-dimethylpiperazin-1-yl)-3-fluorophenyl)-1H-indazole-3-carboxamide, 5-(1-(3,5-dichloropyridin-4-yl)ethoxy)-N-(4-(1-ethylpiperidin-4-yl)phenyl)-1H-indazole-3-carboxamide, 5-(1-(3, 5-dichloropyridin-4-yl)ethoxy)-N-(1-(2-morpholinoethyl)-1H-pyrazol-4-yl)-1H-indazole-3-carboxamide, 5-(1-(3, 5-dichloropyridin-4-yl)ethoxy)-N-(1-ethyl-1H-pyrazol-4-yl)-1H-indazole-3-carboxamide, 5-(1-(3,5-dichloropyridin-4-yl)ethoxy)-N-(1-(1-methylazetidin-3-yl)-1H-pyrazol-4-yl)-1H-indazole-3-carboxamide, 5-(1-(3,5-dichloropyridin-4-yl)ethoxy)-N-(1-(((1-methylpiperidin-4-yl)methyl)-1H-pyrazol-4-yl)-1H-indazole-3-carboxamide, 5-(1-(3,5-dichloropyridin-4-yl)ethoxy)-N-(1-(2-oxo-2-(pyrrolidin-1-yl)ethyl)-1H-pyrazol-4-yl)-1H-indazole-3-carboxamide, 5-(1-(3,5-dichloropyridin-4-yl)ethoxy)-N-(1-(2-(dimethylamino)-2-oxoethyl)-1H-pyrazol-4-yl)-1H-indazole-3-carboxamide, 5-(1-(3,5-dichloropyridin-4-yl)ethoxy)-N-(1-(2-(pyrrolidin-1-yl)ethyl)-1H-pyrazol-4-yl)-1H-indazole-3-carboxamide, 5-(1-(3,5-dichloropyridin-4-yl)ethoxy)-N-(1-isopropyl-1H-pyrazol-4-yl)-1H-indazole-3-carboxamide, N-(1-cyclobutyl-1H-pyrazol-4-yl)-5-(1-(3,5-dichloropyridin-4-yl)ethoxy)-1H-indazole-3-carboxamide, 5-(1-(3,5-dichloropyridin-4-yl)ethoxy)-N-(1-(2,2,2-trifluoroethyl)-1H-pyrazol-4-yl)-1H-indazole-3-carboxamide, 5-(1-(3,5-dichloropyridin-4-yl)ethoxy)-N-(1-(3-hydroxypropyl)-1H-pyrazol-4-yl)-1H-indazole-3-carboxamide, 5-(1-(3,5-dichloropyridin-4-yl)ethoxy)-N-(4-(morpholinomethyl)phenyl)-1H-indazole-3-carboxamide, (R)-5-(1-(3,5-dichloropyridin-4-yl)ethoxy)-N-(1-(1-ethylazetidin-3-yl)-1H-pyrazol-4-yl)-1H-indazole-3-carboxamide, 5-((R)-1-(3,5-dichloropyridin-4-yl)ethoxy)-N-(1-((S)-2-hydroxypropyl)-1H-pyrazol-4-yl)-1H-indazole-3-carboxamide, 5-((R)-1-(3,5-dichloropyridin-4-yl)ethoxy)-N-(1-((R)-2-hydroxypropyl)-1H-pyrazol-4-yl)-1H-indazole-3-carboxamide, (R)-5-(1-(3,5-dichloropyridin-4-yl)ethoxy)-N-(1-ethyl-1H-pyrazol-4-yl)-1H-indazole-3-carboxamide, (R)-5-(1-(3,5-dichloropyridin-4-yl)ethoxy)-N-(1-(3-hydroxycyclobutyl)-1H-pyrazol-4-yl)-1H-indazole-3-carboxamide, (R)-5-(1-(3,5-dichloropyridin-4-yl)ethoxy)-N-(1-(2-(dimethylamino)ethyl)-1H-pyrazol-4-yl)-1H-indazole-3-carboxamide, (R)-5-(1-(3,5-dichloropyridin-4-yl)ethoxy)-N-(1-(2-morpholinoethyl)-1H-pyrazol-4-yl)-1H-indazole-3-carboxamide, (R)-5-(1-(3,5-dichloropyridin-4-yl)ethoxy)-N-(1-(2-hydroxy-2-methylpropyl)-1H-pyrazol-4-yl)-1H-indazole-3-carboxamide, (R)-5-(1-(3,5-dichloropyridin-4-yl)ethoxy)-N-(1-((1-ethylazetidin-3-yl)methyl)-1H-pyrazol-4-yl)-1H-indazole-3-carboxamide, (R)-5-(1-(3,5-dichloropyridin-4-yl)ethoxy)-N-(1-((1-ethylpiperidin-4-yl)methyl)-1H-pyrazol-4-yl)-1H-indazole-3-carboxamide, 5-((R)-1-(3,5-dichloropyridin-4-yl)ethoxy)-N-(1-((1-methylpyrrolidin-3-yl)methyl)-1H-pyrazol-4-yl)-1H-indazole-3-carboxamide, 5-((R)-1-(3,5-dichloropyridin-4-yl)ethoxy)-N-(1-((1-methylpyrrolidin-2-yl)methyl)-1H-pyrazol-4-yl)-1H-indazole-3-carboxamide, 5-((R)-1-(3,5-dichloropyridin-4-yl)ethoxy)-N-(1-(1-methylpyrrolidin-3-yl)-1H-pyrazol-4-yl)-1H-indazole-3-carboxamide, 5-((R)-1-(3,5-dichloropyridin-4-yl)ethoxy)-N-(1-((1-methylpiperidin-3-yl)methyl)-1H-pyrazol-4-yl)-1H-indazole-3-carboxamide, 5-((R)-1-(3,5-dichloropyridin-4-yl)ethoxy)-N-(1-((1-methylpiperidin-2-yl)methyl)-1H-pyrazol-4-yl)-1H-indazole-3-carboxamide, 5-(1-(3,5-dichloropyridin-4-yl) propoxy)-N-(1-methyl-1H-pyrazol-4-yl)-1H-indazole-3-carboxamide, (R)-5-(1-(3,5-dichloropyridin-4-yl)ethoxy)-N-(1-(tetrahydro-2H-pyran-4-yl)-1H-pyrazol-4-yl)-1H-indazole-3-carboxamide, (R)-5-(1-(3,5-dichloropyridin-4-yl)ethoxy)-N-(1-(4-hydroxycyclohexyl)-1H-pyrazol-4-yl)-1H-indazole-3-carboxamide, (R)-5-(1-(3,5-dichloropyridin-4-yl)ethoxy)-N-(1-(pyridin-3-ylmethyl)-1H-pyrazol-4-yl)-1H-indazole-3-carboxamide, (R)-5-(1-(3,5-dichloropyridin-4-yl)ethoxy)-N-(1-(pyridin-4-ylmethyl)-1H-pyrazol-4-yl)-1H-indazole-3-carboxamide, and (R)-5-(1-(3,5-dichloropyridin-4-yl)ethoxy)-N-(1-((1-methylazetidin-3-yl)methyl)-1H-pyrazol-4-yl)-1H-indazole-3-carboxamide.

6. A pharmaceutical composition comprising the compound according to claim 1, or an optical isomer thereof, a geometric isomer thereof, a tautomer thereof, or a pharmaceutically acceptable salt thereof, and one or more pharmaceutically acceptable carriers, adjuvants, or excipients.

* * * * *